United States Patent
Dong et al.

(10) Patent No.: US 10,604,796 B2
(45) Date of Patent: Mar. 31, 2020

(54) COMPOSITIONS, METHODS, AND KITS FOR AMPLIFYING NUCLEIC ACIDS

(71) Applicant: APPLIED BIOSYSTEMS, LLC, Carlsbad, CA (US)

(72) Inventors: Shoulian Dong, Mountain View, CA (US); Junko F. Stevens, Menlo Park, CA (US); Danny H. Lee, Union City, CA (US)

(73) Assignee: Applied Biosystems, LLC, Carlsbad, CA (US)

(*) Notice: Subject to any disclaimer, the term of this patent is extended or adjusted under 35 U.S.C. 154(b) by 461 days.

(21) Appl. No.: 14/876,711

(22) Filed: Oct. 6, 2015

(65) Prior Publication Data

US 2016/0024566 A1    Jan. 28, 2016

Related U.S. Application Data

(60) Continuation of application No. 13/902,742, filed on May 24, 2013, now abandoned, which is a continuation of application No. 12/633,759, filed on Dec. 8, 2009, now Pat. No. 8,470,531, which is a division of application No. 11/537,409, filed on Sep. 29, 2006, now abandoned.

(60) Provisional application No. 60/723,383, filed on Oct. 3, 2005.

(51) Int. Cl.
*C12Q 1/6844* (2018.01)
*C12N 15/115* (2010.01)
*G01N 21/64* (2006.01)

(52) U.S. Cl.
CPC .......... *C12Q 1/6846* (2013.01); *C12N 15/115* (2013.01); *G01N 21/6486* (2013.01); *C12N 2310/16* (2013.01)

(58) Field of Classification Search
CPC ............ C12Q 2527/127; C12Q 1/6846; C12Q 1/6848; C12Q 2527/107; C12Q 2549/125; C12N 15/115; C12N 2310/16; C12P 19/34; G01N 21/6486
See application file for complete search history.

(56) References Cited

U.S. PATENT DOCUMENTS

| | | | |
|---|---|---|---|
| 5,587,287 A | 12/1996 | Scalice et al. | |
| 5,693,502 A | 12/1997 | Gold et al. | |
| 5,763,173 A | 6/1998 | Gold et al. | |
| 5,874,557 A | 2/1999 | Gold et al. | |
| 6,020,130 A | 2/2000 | Gold et al. | |
| 6,183,967 B1 | 2/2001 | Jayasena et al. | |
| 6,579,680 B2* | 6/2003 | Frutos | C07H 21/00 435/287.2 |
| 6,830,902 B1 | 12/2004 | Astatke et al. | |
| 7,820,808 B2 | 10/2010 | Moser et al. | |
| 8,043,816 B2 | 10/2011 | Astatke et al. | |
| 8,313,932 B2 | 11/2012 | Moser et al. | |
| 2004/0259116 A1* | 12/2004 | Beckman | C12Q 1/6848 435/6.12 |
| 2005/0053942 A1 | 3/2005 | Kauppinen et al. | |
| 2006/0110748 A1* | 5/2006 | Sorge | C12Q 1/6844 435/6.1 |
| 2007/0212704 A1 | 9/2007 | Dong et al. | |
| 2011/0160289 A1 | 6/2011 | Astatke et al. | |

FOREIGN PATENT DOCUMENTS

| | | |
|---|---|---|
| WO | 1996/041010 A1 | 12/1996 |
| WO | 2001/002559 A1 | 1/2001 |
| WO | 2002/006827 A1 | 1/2002 |
| WO | 2004/090153 A2 | 10/2004 |
| WO | 2007/041201 A3 | 4/2007 |

OTHER PUBLICATIONS

AAT Bioquest Product Technical Information Sheet, pp. 1-3 (Year: 2014).*
Armitage, B. et al., Hairpin-Forming Nucleic acid Oligomers, Biochemistry, vol. 37, pp. 9417-9425 (Year: 1998).*
Shaharabany, M. et al., The DNA-dependent and RNA-dependent DNA polymerase activities of the reverse transcriptases of human immunodeficiency viruses type 1 and 2, AIDS Res. Hum. Retroviruses, vol. 7, pp. 883-888; Abstract (Year: 1991).*
Bebenek, K. et al., Functions of DNA polymerases, Adv. Prot. Chemistry, vol. 69, pp. 137-165 (Year: 2004).*
Knittel, T. et al., PCR with Degenerate Primers Containing Deoxyinosine Fails with Pfu DNA Polymerase, PCR Meth. Appl., vol. 2, pp. 346-347 (Year: 1993).*
Gening, L.V. et al., RNA aptamers selected against DNA polymerase beta inhibit the polymerase activities of DNA polymerases beta and kappa, Nucl. Acids Res., vol. 34, pp. 2579-2586 (Year: 2006).*
EP12151072.1; European Search Report dated May 3, 2012.
PCT/US06/37829 International Search Report and Written Opinion dated Sep. 28, 2007.

(Continued)

*Primary Examiner* — Teresa E Strzelecka

(57) ABSTRACT

The present teachings are directed to compositions, methods, and kits for amplifying target nucleic acids while reducing non-specific fluorescence and undesired amplification products, sometimes referred to as secondary amplification products or spurious side-products. The enzyme inhibitors disclosed herein comprise a nucleotide sequence and at least one quencher. Complexes comprising an enzyme inhibitor associated with an enzyme, wherein at least one enzymatic activity of the enzyme is inhibited, are also provided. Methods for amplifying a target nucleic acid while reducing undesired amplification products are disclosed, as are methods for reducing non-specific fluorescence. Kits for expediting the performance of certain disclosed methods are also provided.

11 Claims, 12 Drawing Sheets

Figure 1A:
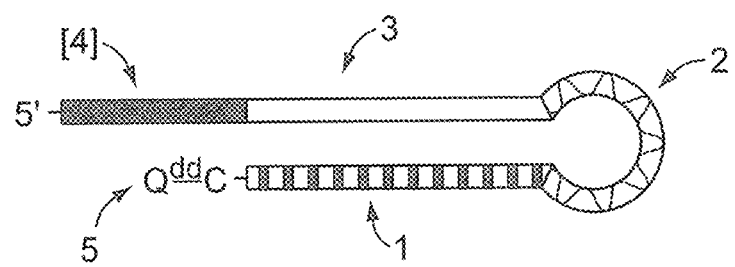
Figure 1B:
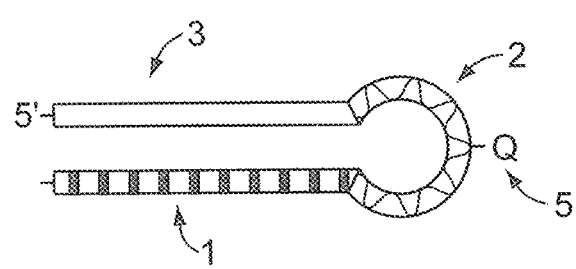
Figure 1C:
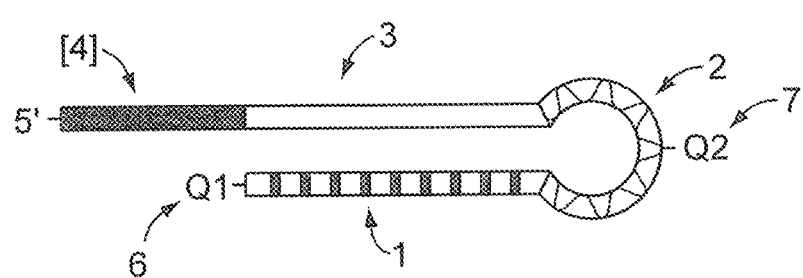
Figure 1D:
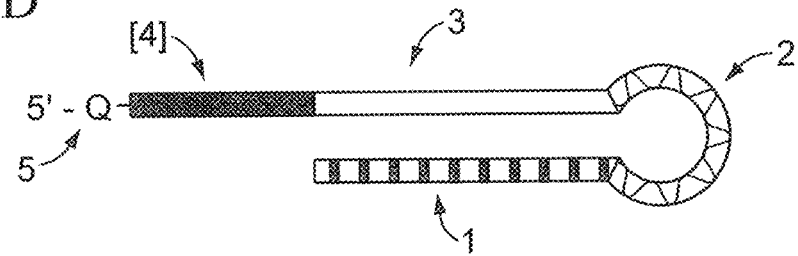
Figure 1E:
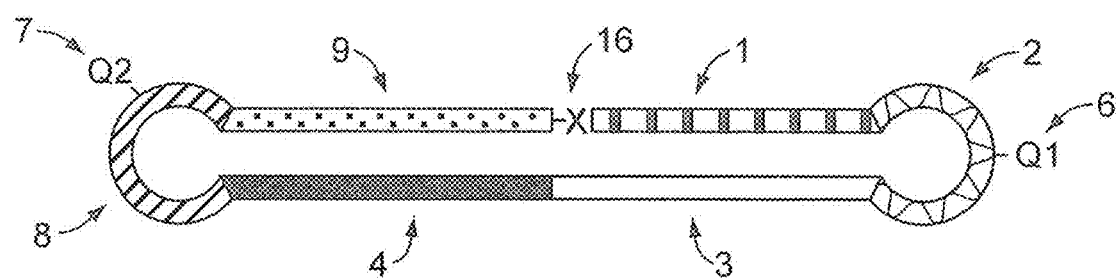
Figure 1F:
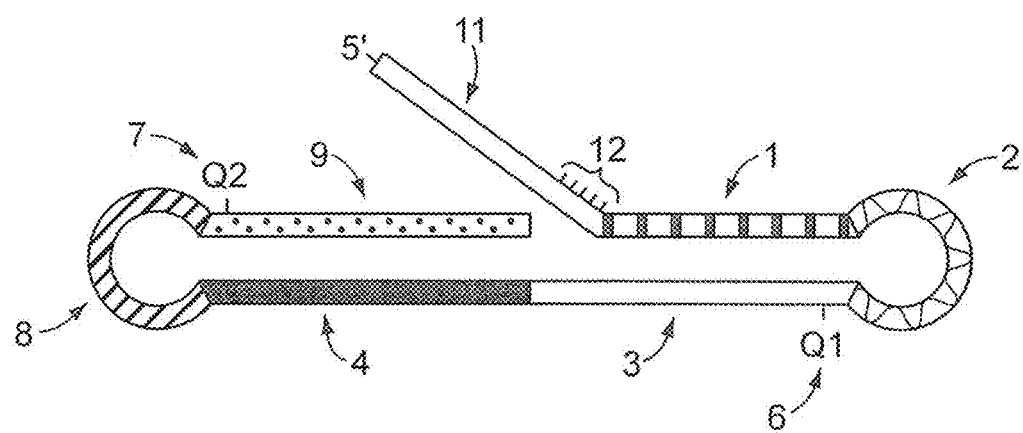
Figure 2A:
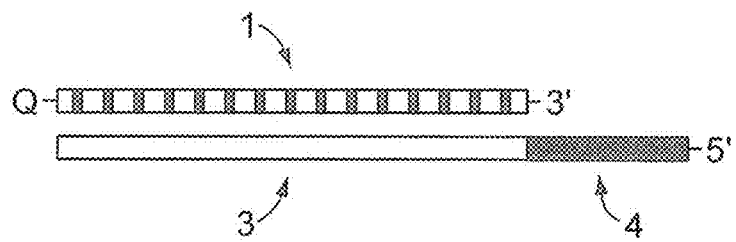
Figure 2B:
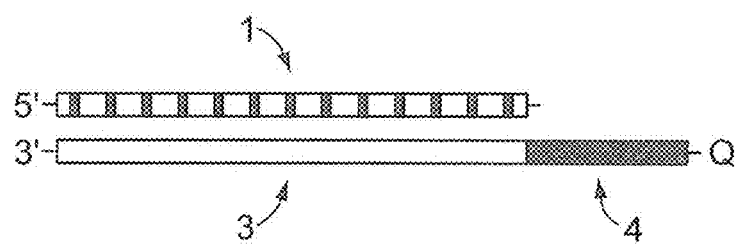
Figure 2C:
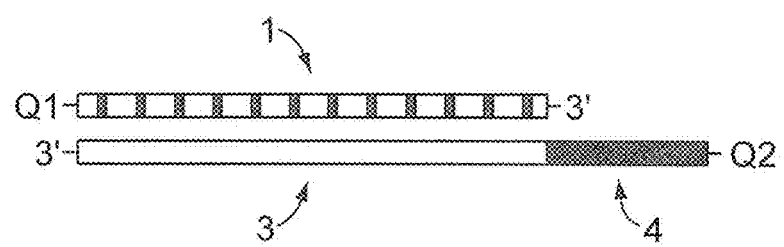
Figure 2D:
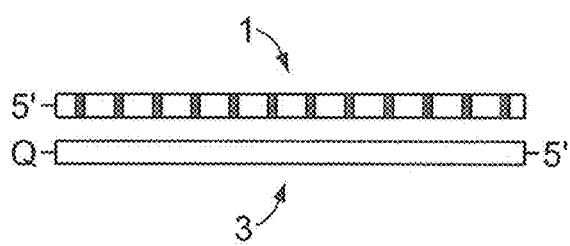
Figure 2E:
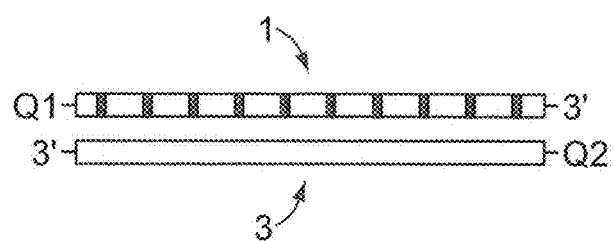

Specification includes a Sequence Listing.

(56) References Cited

OTHER PUBLICATIONS

EP06815660.3; Extended European Search Report dated Oct. 22, 2009.
Beker, et al. "A Quantitative Method of Determining Initial Amounts of DNA by Polymerase Chain Reaction Cycle Titration Using Digital Imaging and a Novel DNA Stain", *Anal. Biochem.*, vol. 237, 1996; pp. 204-207.
Bellecave, et al. "Selection of DNA Aptamers That Bind the RNA-Dependent RNA Polymerase of Hepatitis C Virus and Inhibit Viral RNA Synthesis In Vitro," *Oligonucleotides*, vol. 13, Mary Ann Lieberg, Inc. 2003; pp. 455-463.
Dang, et al. "Oligonucleotide Inhibitors of Taq DNA Polymerase Facilitate Detection of Low Copy Number Targets by PCR," *Journal of Molecular Biology*, vol. 264, Academic Press Ltd. 1996; pp. 268-278.
Hannoush, et al. "Selective Inhibition of HIV-1 Reverse Transcriptase (HIV-1 RT) RNase H by Small RNA Hairpins and Dumbbells," *Chem. Bio. Chem.*, vol. 5, Whiley-VCH Verlag GmbH & Co. KGaA, Weinheim 2004; pp. 527-533.
Heinlein, T., et al., "Photoinduced Electron Transfer between Fluorescent Dyes and Guanosine Residues in DNA-Hairpins", *J. Phys. Chem. B.*, vol. 107, pp. 7957-7964.
Jayasena, Sumedha D. "Aptamers: An Emerging Class of Molecules That Rival Antibodies in Diagnostics", *Clinical Chemistry*, vol. 45, No. 9, 1999; pp. 1628-1650.
Knemeyer, J. P. et al. "Probes for Detection of Specific DNA Sequences at the Single-Molecule Level", *Anal. Chem.*, vol. 72, American Chemical Society 2000; pp. 3717-3724.
Kulbachinskiy, et al. "Aptamers to *Escherichia coli* Core RNA Polymerase that Sense its Interaction with Rifampicin, σ-subnit and GreB," *European Journal of Biochemistry*, vol. 271, 2004; pp. 4921-4931.
Kutyavin, Igor V. et al. "3'-Minor groove binder-DNA probes increase sequence specificity at PCR extension temperatures", *Nucleic Acids Research*, vol. 28, No. 2, 2000; pp. 655-661.
Langhorst, B. et al. "Polbase: a repository of biochemical, genetic and structural information about DNA polymerases," *Nucleic Acid Research*, vol. 40, Database issue, Oct. 12, 2011; pp. D381-D387.
Lin, et al. "Inhibition of Multiple Thermostable DNA Polymerases by a Heterodimeric Aptamer", *Journal of Molecular Biology*, vol. 271, No. 1, Academic Press Ltd., Aug. 1997; pp. 100-111.
NCBI Protein Database Search for "helicase" downloaded Dec. 3, 2012; 2 pages.
New England BioLabs, Inc. "T7 RNA Polymerase", at URL http://www.neb.com/nebecomm/products/productm0251.asp, Downloaded May 25, 2012.
Nishikawa, Fumiko, et al. "Inhibition of HCV NS3 Protease by RNA Aptamers in Cells", *Nuc. Acids Research*, vol. 31, No. 7, pp. 1935-1943.
Pelletier, Huguette, et al., "Structures of Ternary Complexes of Rat DNA Polymerase beta, a DNA Template-Primer, and ddCTP", *Science*, vol. 264, pp. 1891-1903.
Stratagene Catalog, "Stragagene Cloning Systems: Tools and Technology for Life Sciences", *Gene Characterization Kits*, 1988.
Thomas, et al. "Selective Targeting and Inhibition of Yeast RNA Polymerase II by RNA Aptamers", *The Journal of Biological Chemistry*, vol. 272, No. 44, The American Society for Biochemistry and Molecular Biology, Inc., USA, Oct. 31, 1997; pp. 27980-27986.
Unruh, J. R. et al. "Orientational dynamics and dye-DNA interactions in a dye-labeled DNA aptamer", *Biophysical Journal*, vol. 88, No. 5, May 2005; pp. 3455-3465.
Yakimovich, O. Y. et al. "Influence of DNA aptamer structure on the specificity of binding to Taq DNA polymerase", Biochemistry (Moscow), vol. 68, No. 2, Feb. 2003; pp. 228-235.

\* cited by examiner

SEQUENCE LISTING

<160> NUMBER OF SEQ ID NOS: 7

<210> SEQ ID NO 1
<211> LENGTH: 51
<212> TYPE: DNA
<213> ORGANISM: Artificial Sequence
<220> FEATURE:
<223> OTHER INFORMATION: synthetic construct

<400> SEQUENCE: 1
tctgggataa ttatggtaaa tatatgtttt catatattta ttataattat c     51

<210> SEQ ID NO 2
<211> LENGTH: 49
<212> TYPE: DNA
<213> ORGANISM: Artificial Sequence
<220> FEATURE:
<223> OTHER INFORMATION: synthetic construct

<400> SEQUENCE: 2
ttctgggata attatggtaa atatattta tatatttatt ataattatc          49

```
<210> SEQ ID NO 3
<211> LENGTH: 47
<212> TYPE: DNA
<213> ORGANISM: Artificial Sequence
<220> FEATURE:
<223> OTHER INFORMATION: synthetic construct

<400> SEQUENCE: 3
tctgggataa ttatggtaaa tatgttttca tatttattat aattatc          47

<210> SEQ ID NO 4
<211> LENGTH: 45
<212> TYPE: DNA
<213> ORGANISM: Artificial Sequence
<220> FEATURE:
<223> OTHER INFORMATION: synthetic construct

<400> SEQUENCE: 4
tgtaaaacga cggccagttc tcatattctc tcatcctcct gtccc            45

<210> SEQ ID NO 5
<211> LENGTH: 38
<212> TYPE: DNA
<213> ORGANISM: Artificial Sequence
<220> FEATURE:
<223> OTHER INFORMATION: synthetic construct

<400> SEQUENCE: 5
caggaaacag ctatgaccaa gcggctttag gcccacct                    38

<210> SEQ ID NO 6
<211> LENGTH: 19
<212> TYPE: DNA
<213> ORGANISM: Artificial Sequence
<220> FEATURE:
<223> OTHER INFORMATION: synthetic construct

<400> SEQUENCE: 6
tgggagtcct ggaagcagc                                         19

<210> SEQ ID NO 7
<211> LENGTH: 21
<212> TYPE: DNA
<213> ORGANISM: Artificial Sequence
<220> FEATURE:
<223> OTHER INFORMATION: synthetic construct

<400> SEQUENCE: 7
tggcttctgg tcaacaagtg c                                      21
```

COMPOSITIONS, METHODS, AND KITS FOR AMPLIFYING NUCLEIC ACIDS

CROSS REFERENCE TO RELATED APPLICATIONS

This application is a continuation application of U.S. patent application Ser. No. 13/902,742, filed May 24, 2015, which is a continuation application of U.S. patent application Ser. No. 12/633,759, filed Dec. 8, 2009, now U.S. Pat. No. 8,470,531 granted Jun. 25, 2013 which claims a priority benefit under 35 U.S.C. § 119(e) from U.S. patent application Ser. No. 11/537,409, filed Sep. 29, 2006 (now Abandoned) and U.S. Provisional Patent Application No. 60/723,383, filed Oct. 3, 2005, the contents of which is incorporated herein by reference.

FIELD

The present teachings generally relate to compositions, methods, and kits for amplifying nucleic acids while reducing non-specific fluorescence and undesired amplification products.

INTRODUCTION

While the polymerase chain reaction (PCR) and related techniques are highly useful for a variety of applications, the amplification of non-target nucleic acids due to undesired side-reactions can present a significant problem. Such side reactions can occur as a result of mis-priming of non-target nucleic acids and/or primer oligomerization, sometimes referred to as primer dimer formation, and the subsequent amplification of these priming artifacts. This is especially true in applications in which PCR is carried out using a mixture of nucleic acids with significant background nucleic acids while the target nucleic acid is present in low copy number (see, e.g., Chou et al., Nucl. Acids Res. 20:1717-1723 (1992). The generation of non-specifically amplified products has been attributed at least in part to DNA polymerase activity at ambient temperature that extends non-specifically annealed primers. (see, e.g., id.; Li et al., Proc. Natl. Acad. Sci. 87:4580 (1990). Accordingly, inhibition of DNA polymerase activity at ambient temperature is beneficial in controlling the generation of secondary amplicons.

Several techniques have been described which reportedly decrease the formation of undesired secondary amplification products. According to certain "manual hot start" techniques, a component critical to DNA polymerase activity (e.g., divalent ions and/or the DNA polymerase itself) is not added to the reaction mixture until the temperature of the mixture is high enough to prevent non-specific primer annealing (see, e.g., Chou et al., Nucl. Acids Res. 20:1717-1723 (1992); and D'Aquila et al., Nucl. Acids Res. 19:3749 (1991)). Less labor-intensive techniques employ the physical separation or reversible inactivation of at least one component of the amplification reaction. For example, the magnesium or the DNA polymerase can be sequestered in a wax bead, which melts as the reaction temperature increases, releasing the sequestered component only at the elevated temperature. According to other techniques, the DNA polymerase is reversibly inactivated or modified, for example by a reversible chemical modification of the DNA polymerase or the binding of an antibody (see, e.g., Birch et al., U.S. Pat. No. 5,677,152). At elevated reaction temperatures, the chemical modification is reversed or the antibody molecule is denatured, releasing a functional DNA polymerase. However, some of these techniques appear to be leaky, in that some DNA polymerase activity is detectable at lower reaction temperatures, or they require extended exposure of the reaction mixture at high temperatures to fully activate the DNA polymerase.

Certain currently used nucleic acid amplification techniques include a step for detecting and/or quantifying amplification products that comprise a nucleic acid dye, for example but not limited to, SYBR® Green I (Molecular Probes, Eugene, Oreg.), including certain real-time and/or end-point detection techniques (see, e.g., Ririe et al., Analyt. Biochem. 245:154-60 (1997). Typically the nucleic acid dye associates with double-stranded segments of the amplification products and/or primer-template duplexes and emit a detectable fluorescent signal at a wavelength that is characteristic of the particular nucleic acid dye. Certain amplification methods comprise a detection step for evaluating the purity of the amplification product(s) that comprises a nucleic acid dye, for example but not limited to, post-PCR dissociation curve analysis, also known as melting curve analysis. Since the melting curve of an amplicon is dependent on, among other things, its length and sequence, amplicons can generally be distinguished by their melting curves (see, e.g., Zhang et al., Hepatology 36:723-28 (2002)). A dissociation or melting curve can be obtained during certain amplification reactions by monitoring the nucleic acid dye fluorescence as the reaction temperatures pass through the melting temperature of the amplicon(s). The dissociation of a double-stranded amplicon is observed as a sudden decrease in fluorescence at the emission wavelength characteristic of the nucleic acid dye. According to certain dissociation curve analysis techniques, an amplification product is classified as "pure" when the melting curve shows a single, consistent melting temperature, sometimes graphically displayed as a peak on a plot of the negative derivative of fluorescent intensity versus temperature (−dF/dt vs. T). For example, the appearance of multiple peaks in such a dissociation curve from a single-plex amplification typically indicates the presence of undesired side reaction products. When such nucleic acid dye-based amplification product detection techniques are employed, it is often desirable to: 1) at least decrease and preferably eliminate the formation of undesired side-reaction products and 2) at least decrease and preferably eliminate fluorescence peaks resulting from the denaturing of double-stranded segments of other nucleic acids, i.e., non-amplification products.

Certain other amplification techniques may also yield undesired amplification products due to, among other things, non-specific annealing of primers, ligation probes, cleavage probes, promoter-primers, and so forth, and subsequent enzyme activity at sub-optimal temperatures. For example, while reaction components are being combined, often at room temperature, or while the reaction composition is being heated to a desired reaction temperature. At least some of these techniques can benefit from a reduction in background fluorescence.

SUMMARY

The present teachings are directed to compositions, methods, and kits for amplifying target nucleic acids while reducing non-specific fluorescence and undesired amplification products, sometimes referred to in the art as secondary amplicons or spurious side-products.

Enzyme inhibitors comprising a nucleotide sequence and a quencher are disclosed. The disclosed inhibitors are designed to inhibit at least one enzymatic activity of an enzyme. In certain embodiments, the nucleotide sequence of the enzyme inhibitor comprises an aptamer. In some embodiments, an enzyme inhibitor comprises an aptamer that is capable of forming at least one double-stranded segment (see, e.g., Yakimovich et al., Biochem. (Mosc.) 68(2):228-35 (2003); Nickens et al., RNA 9:1029-33 (2003); Nishikawa et al., Oligonucleotides 14:114-29 (2004); and Umehara et al., J. Biochem. 137:339-74 (2005)). In some embodiments, an enzyme inhibitor comprises a multiplicity of different quenchers. In certain embodiments, the enzyme inhibitor can assume a conformation comprising at least one double-stranded segment at a first temperature, but is single-stranded or substantially single-stranded when heated to a second temperature. According to certain embodiments, an enzyme inhibitor comprising at least one double-stranded segment can form a complex with at least one of: a DNA polymerase, including without limitation a reverse transcriptase; an RNA polymerase; a cleaving enzyme, including without limitation, a structure-specific nuclease; a helicase; and a ligase. In certain embodiments, an enzyme inhibitor is an ineffective substrate for the corresponding enzyme because the inhibitor comprises a blocking group, a nucleotide analog, an uncleavable internucleotide linkage, or combinations thereof.

DNA polymerase inhibitors comprising a nucleotide sequence and a quencher are disclosed. Some DNA polymerase inhibitors comprise two or more quenchers that can be the same quencher or different quenchers. In certain embodiments, a DNA polymerase inhibitor further comprises a minor groove binder that, in some embodiments, comprises a quencher. In some embodiments, the 3'-end of a nucleotide sequence of a DNA polymerase inhibitor is not extendible by a DNA polymerase, typically due to the presence of a blocking group or non-extendible nucleotide. In some embodiments, the nucleotide sequence of a DNA polymerase inhibitor comprises an aptamer capable of forming at least one double-stranded segment (see, e.g., Yakimovich et al., Biochem. (Mosc.) 68(2):228-35 (2003)).

Complexes comprising an enzyme and an enzyme inhibitor are provided. Certain complexes comprise: a DNA polymerase and a DNA polymerase inhibitor; a ligase and a ligase inhibitor; an RNA polymerase and an RNA polymerase inhibitor; a cleaving enzyme and a cleaving enzyme inhibitor; or a helicase and a helicase inhibitor. Certain complexes further comprise a deoxyribonucleotide, a ribonucleotide, a nucleotide analog, an accessory protein, for example but not limited to a single-stranded binding protein (SSB) or a proliferating cell nuclear antigen (PCNA), or combinations thereof. Typically the enzyme-enzyme inhibitor complex can form at a first temperature, and while associated with the inhibitor in the complex, at least one catalytic activity of the enzyme is inhibited. When the complex is heated to a second temperature, the complex dissociates, releasing the enzyme.

In certain embodiments, an enzyme-enzyme inhibitor complex comprises a DNA polymerase and a DNA polymerase inhibitor. In certain embodiments, a DNA polymerase-DNA polymerase inhibitor complex further comprises a nucleotide triphosphate (NTP) and/or a nucleotide analog. Certain complex embodiments comprise a DNA polymerase inhibitor in a stem-loop conformation associated with a DNA polymerase, and optionally, a NTP and/or a nucleotide analog. Certain complex embodiments comprise a DNA polymerase associated with a DNA polymerase inhibitor comprising at least two oligonucleotides that are annealed to form a duplex comprising at least one double-stranded segment, and optionally, a NTP and/or a nucleotide analog. Typically, the DNA synthesis activity of the DNA polymerase is inhibited when it is complexed with a DNA polymerase inhibitor of the current teachings, and optionally, a NTP and/or a nucleotide analog.

Methods for reducing non-specific fluorescence comprising the enzyme inhibitors of the present teachings are disclosed. According to certain methods, an enzyme is contacted with an enzyme inhibitor under conditions suitable for an enzyme-enzyme inhibitor complex to form. At least one enzymatic activity of the enzyme is inhibited while the enzyme is in the complex. When the enzyme-enzyme inhibitor complex is heated to a suitable second temperature, the complex dissociates, releasing the enzyme.

Some methods for reducing non-specific fluorescence comprise a DNA polymerase inhibitor of the present teachings. According to certain such methods, a reaction composition is formed at a first temperature comprising: a DNA polymerase, a DNA polymerase inhibitor comprising a nucleotide sequence and a quencher, a NTP and/or a nucleotide analog, a target nucleic acid, a primer, and a nucleic acid dye. In certain embodiments, the primer comprises a primer pair. At the first temperature, the DNA polymerase inhibitor comprises at least one double-stranded segment and can form a complex with the DNA polymerase. The quencher of the DNA polymerase inhibitor can absorb at least some of the fluorescent signal of the nucleic acid dye associated with the double-stranded segment of the DNA polymerase inhibitor. The reaction composition is heated to a second reaction temperature that is typically near, at, or above the melting temperature of the DNA polymerase inhibitor, causing at least some of the DNA polymerase inhibitor-DNA polymerase complexes to dissociate. The reaction composition is subjected to at least one cycle of amplification and a multiplicity of amplicons is generated. The double-stranded amplicons can be detected, either in "real time" or after the amplification reaction is completed, due to the fluorescence of the nucleic acid dye associated with the amplicons, while the fluorescence of the nucleic acid dye associated with the double-stranded segments of the DNA polymerase inhibitors is at least reduced by the quencher.

Methods for amplifying a target nucleic acid using the enzyme inhibitors of the present teachings are also disclosed. According to certain such methods, a reaction composition is formed at a first temperature comprising: a DNA polymerase, a DNA polymerase inhibitor comprising a nucleotide sequence and a quencher, a NTP, a target nucleic acid, a primer, and a nucleic acid dye. In certain embodiments, the primer comprises a primer pair. At the first temperature, the DNA polymerase inhibitor comprises at least one double-stranded segment and can form a complex with the DNA polymerase. The quencher of the DNA polymerase inhibitor can absorb at least some of the fluorescence emitted by the nucleic acid dye associated with the double-stranded segment of the DNA polymerase inhibitor. The reaction composition is heated to a second reaction temperature that is typically near, at, or above the melting temperature of the DNA polymerase inhibitor, causing at least some of the DNA polymerase inhibitor-DNA polymerase complexes to dissociate. The reaction composition is subjected to at least one cycle of amplification and a multiplicity of amplicons is generated. In certain embodiments, the amount of amplicon that is generated is increased due to the presence of the DNA polymerase inhibitor in the reaction composition.

According to certain methods, a reaction composition comprises a target nucleic acid, an enzyme, an enzyme inhibitor, a nucleic acid dye, and at least one of: a NTP, a nucleotide analog, a primer, a ligation probe pair, a cleavage probe pair, a promoter-primer, a cofactor, for example but not limited to a substance comprising NAD+, and an accessory protein, including without limitation a PCNA and/or an SSB.

According to certain methods, a ligase is contacted with a ligase inhibitor and under suitable conditions, a ligase-ligase inhibitor complex is formed. According to certain methods, a cleaving enzyme is contacted with a cleaving enzyme inhibitor and under suitable conditions, a cleaving enzyme-cleaving enzyme inhibitor complex is formed. According to certain methods, a helicase is contacted with a helicase inhibitor and under suitable conditions, a helicase-helicase inhibitor complex is formed. According to some methods, an RNA polymerase is contacted with an RNA polymerase inhibitor and under suitable conditions, an RNA polymerase-RNA polymerase inhibitor complex is formed.

Kits for performing certain of the instant methods are also disclosed. In some embodiments, kits comprise an enzyme inhibitor comprising a nucleotide sequence and a quencher. In certain embodiments, kits comprise two or more different enzyme inhibitors. In some embodiments, an enzyme inhibitor can form a complex with an RNA polymerase, a helicase, a cleaving enzyme, or a ligase. Certain kit embodiments further comprise a cleavage probe set, a ligation probe set, a primer, a promoter-primer, or combinations thereof.

Certain kit embodiments include at least one DNA polymerase inhibitor comprising a nucleotide sequence and a quencher. In some embodiments, a kit comprises two or more DNA polymerase inhibitors. In certain embodiments, a DNA polymerase inhibitor comprises a minor groove binder. Certain kit embodiments further comprise at least one of: a primer, a primer pair, a nucleic acid dye, a DNA polymerase, and a reporter probe. In some embodiments, a kit comprises a DNA-dependent DNA polymerase and a reverse transcriptase.

These and other features of the present teachings are set forth herein.

DRAWINGS

The skilled artisan will understand that the drawings, described below, are for illustration purposes only. These figures are not intended to limit the scope of the present teachings in any way.

FIGS. 1A through 1F: schematically depicts illustrative embodiments of certain exemplary enzyme inhibitors comprising a single oligonucleotide.

FIGS. 2A through 2E: schematically depicts illustrative embodiments of certain exemplary enzyme inhibitors comprising a multiplicity of oligonucleotides.

Figure 3:
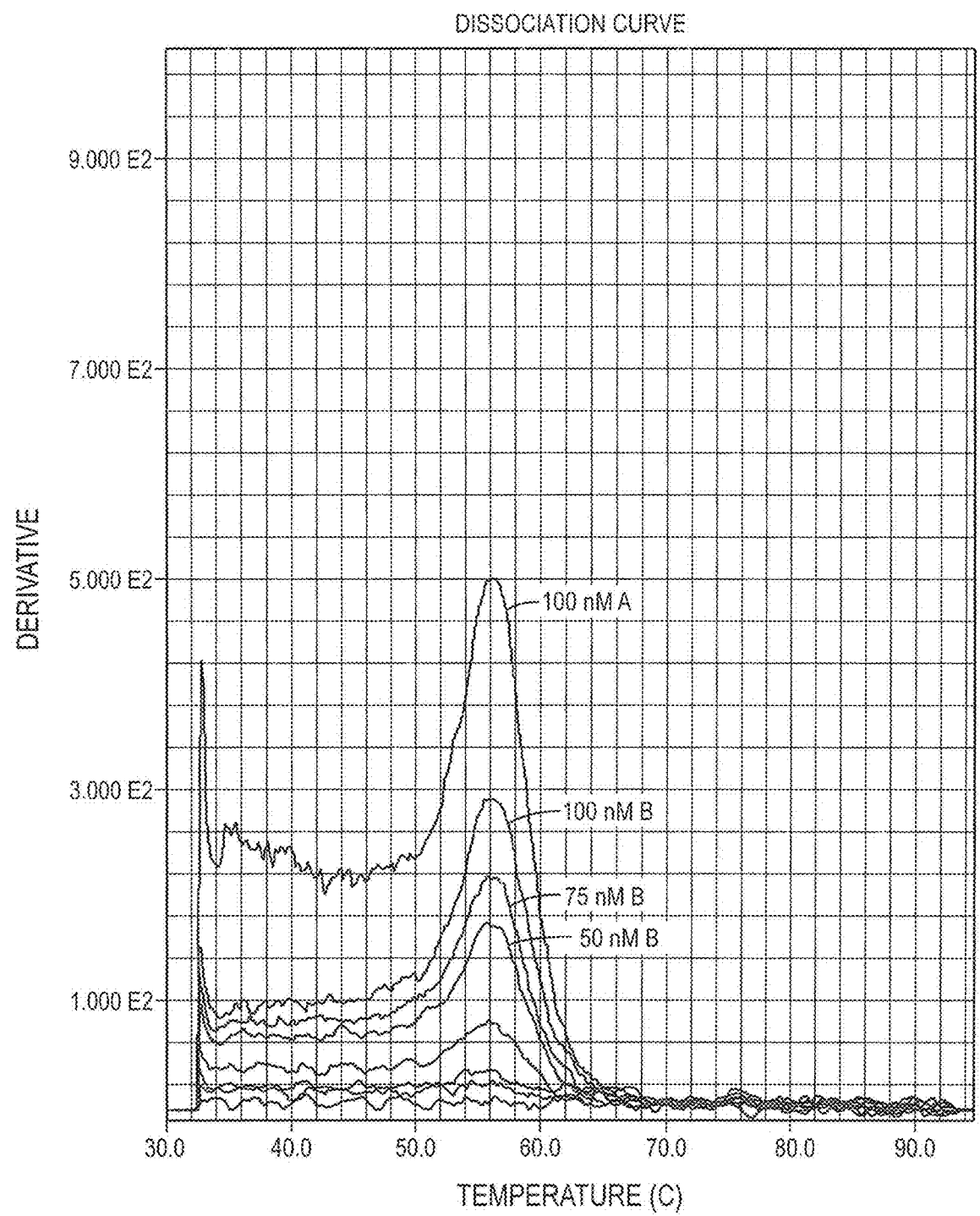

FIG. 3: depicts dissociation curves obtained using certain exemplary DNA polymerase inhibitors, plotted as the negative derivative of fluorescence (−dF/dt) versus temperature in ° C.

Figure 4:
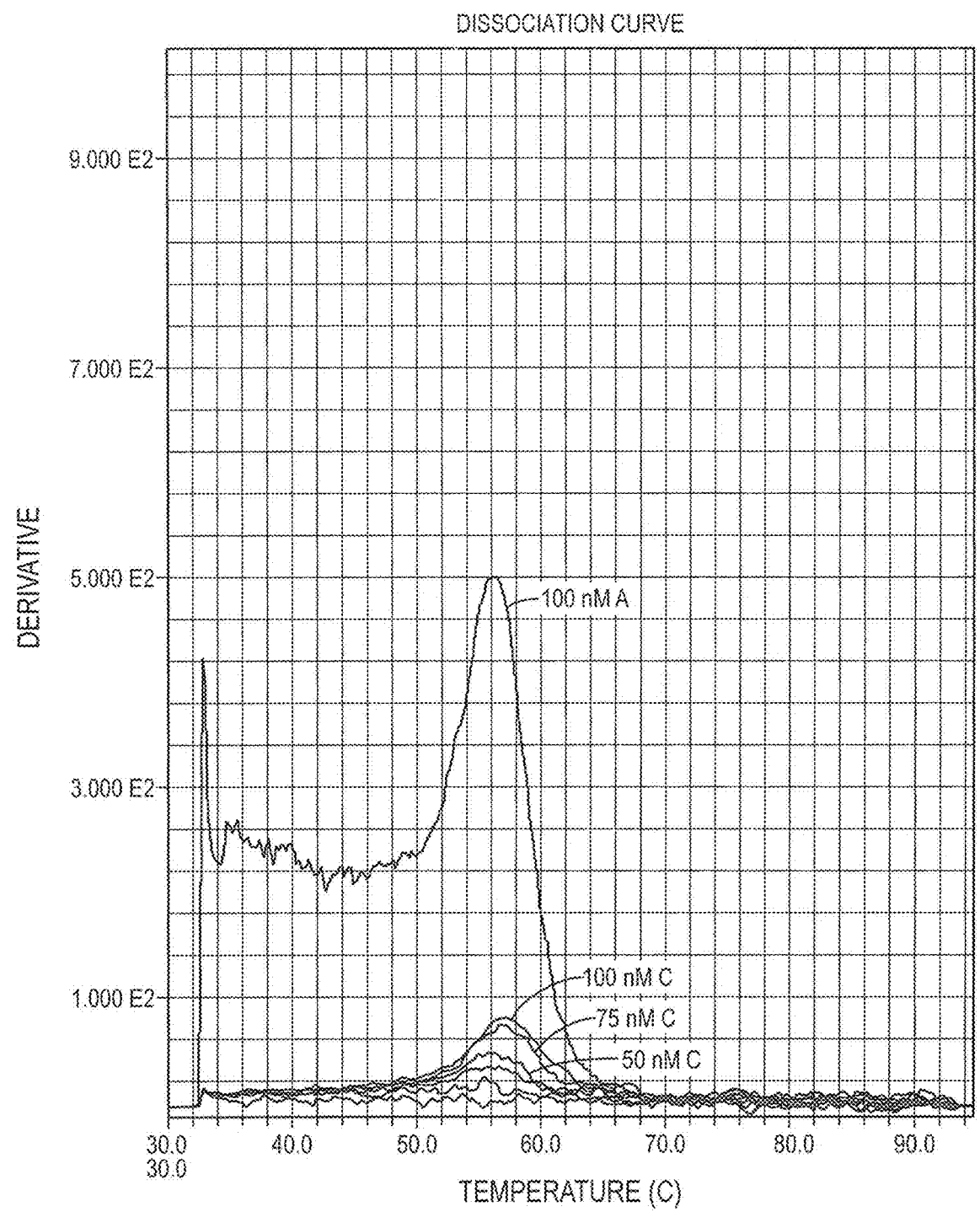

FIG. 4: depicts dissociation curves obtained using certain exemplary DNA polymerase inhibitors, plotted as the negative derivative of fluorescence versus temperature in ° C.

Figure 5:
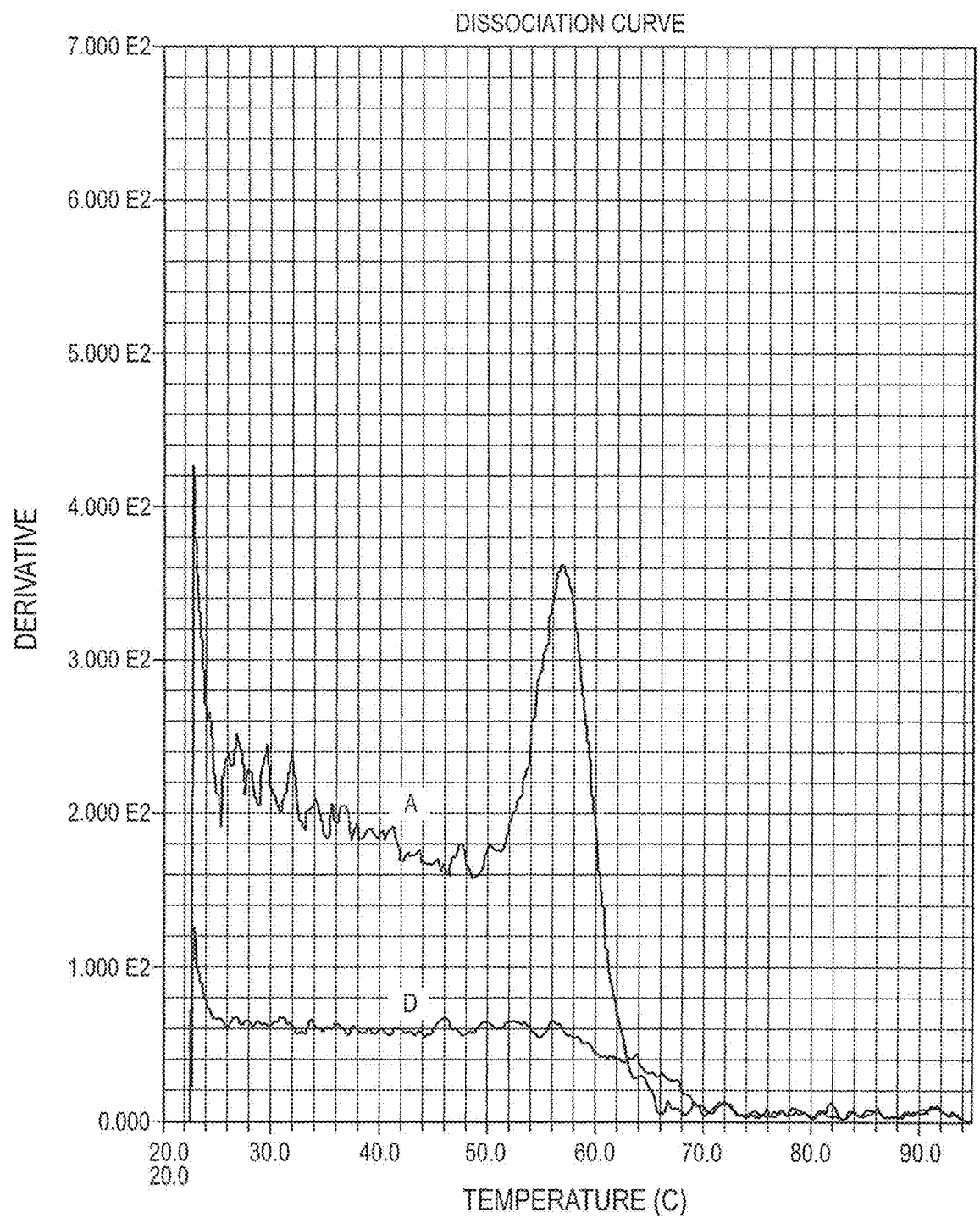

FIG. 5: depicts dissociation curves obtained using certain exemplary DNA polymerase inhibitors, plotted as the negative derivative of fluorescence versus temperature in ° C.

Figure 6:
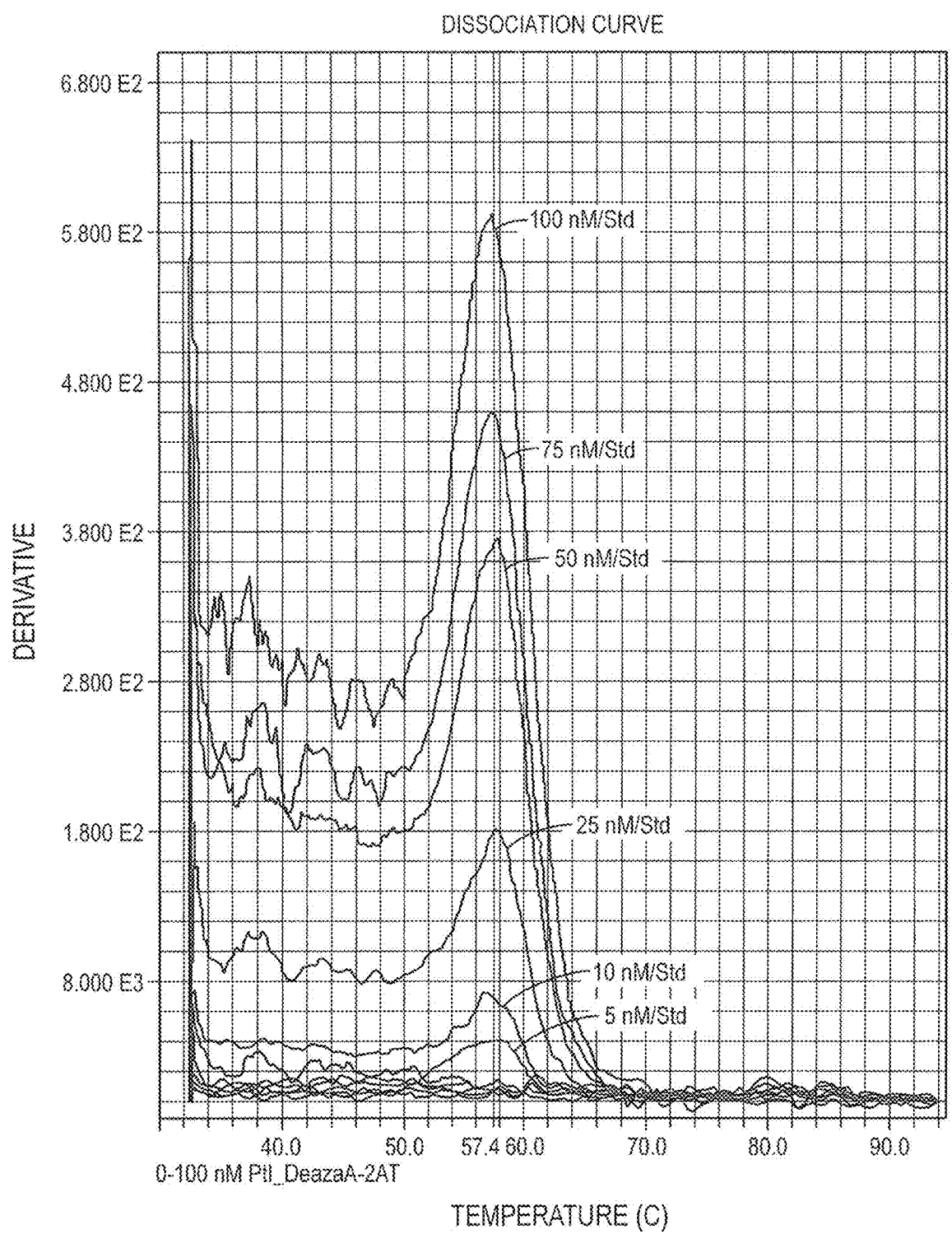

FIG. 6: depicts dissociation curves obtained using certain exemplary DNA polymerase inhibitors, plotted as the negative derivative of fluorescence versus temperature in ° C.

Figure 7:
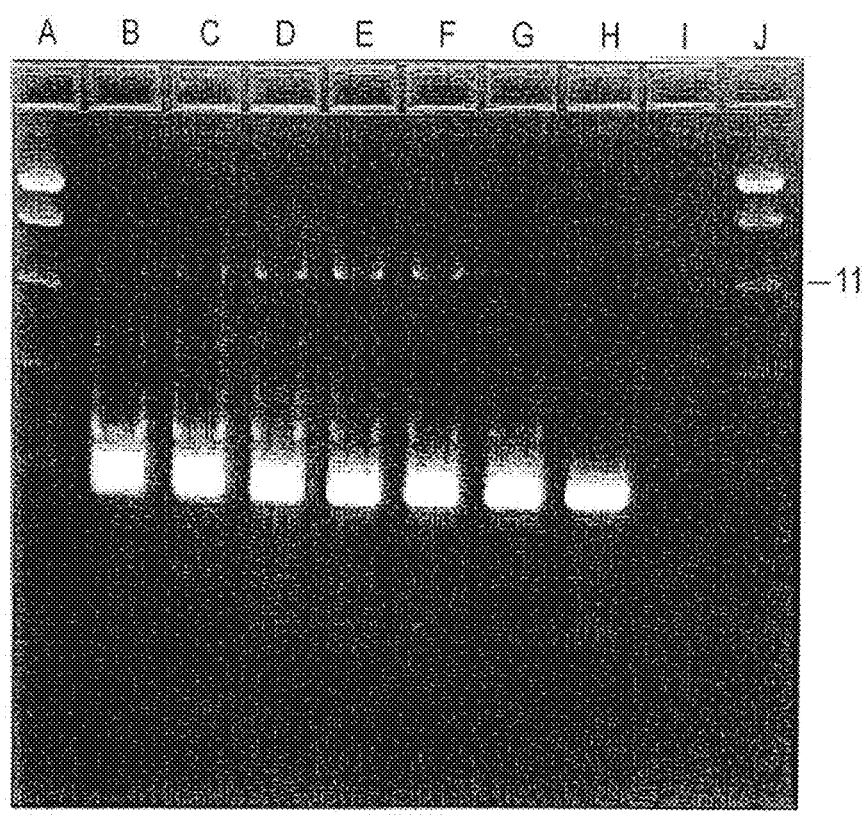

FIG. 7: depicts a photograph of agarose gel. Aliquots of a series of thermocycled reaction compositions comprising amplicons generated in varying concentrations of an exemplary enzyme inhibitor were electrophoresed in separate lanes of a non-denaturing agarose gel and visualized with ethidium bromide, as described in Example 2. Lanes A and J: size ladder comprising 1200 base pair, 800 base pair, 400 base pair, 200 base pair, and 100 base pair size standards; lanes B-G: aliquots of the thermocycled reaction compositions comprising 5, 10, 25, 50, 75 or 100 nM DNA polymerase inhibitor E, respectively; lane H: no template control reaction composition comprising 50 nM DNA polymerase inhibitor E; lane I: blank.

Figure 8:
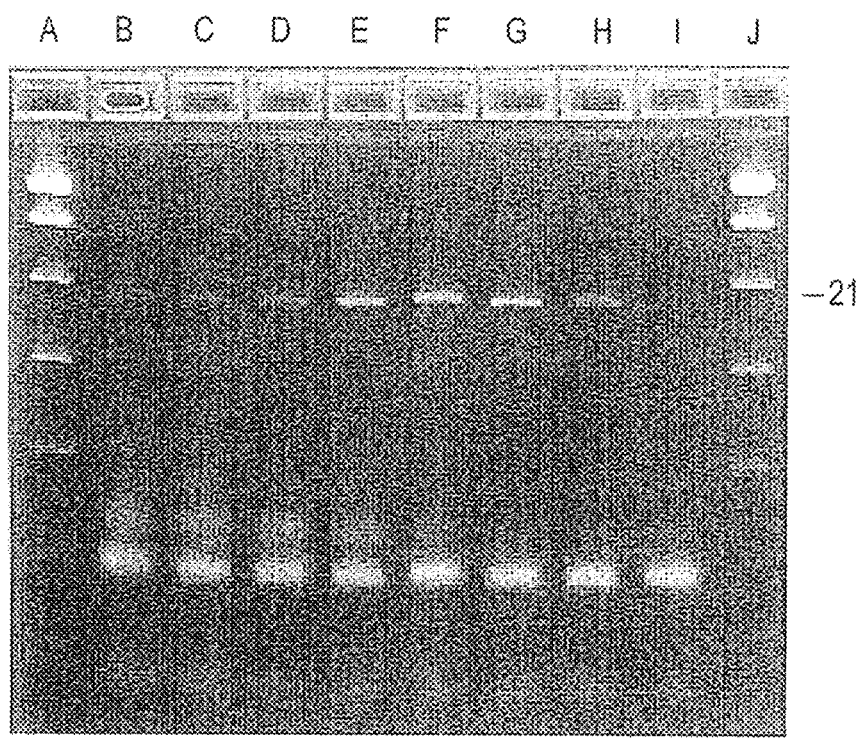

FIG. 8: depicts a photograph of an agarose gel. Aliquots of a series of thermocycled reaction compositions comprising amplicons generated in varying concentrations of an exemplary DNA polymerase inhibitor were electrophoresed in separate lanes of a non-denaturing agarose gel and visualized with ethidium bromide, as described in Example 3. Lanes A and J: size ladder comprising 1200 base pair, 800 base pair, 400 base pair, 200 base pair, and 100 base pair size standards; lanes B-H: aliquots of thermocycled reaction compositions comprising 0, 5, 10, 25, 50, 75, or 100 nM DNA polymerase inhibitor E, respectively; lane I: no template control reaction composition comprising 50 nM DNA polymerase inhibitor E.

Figure 9:
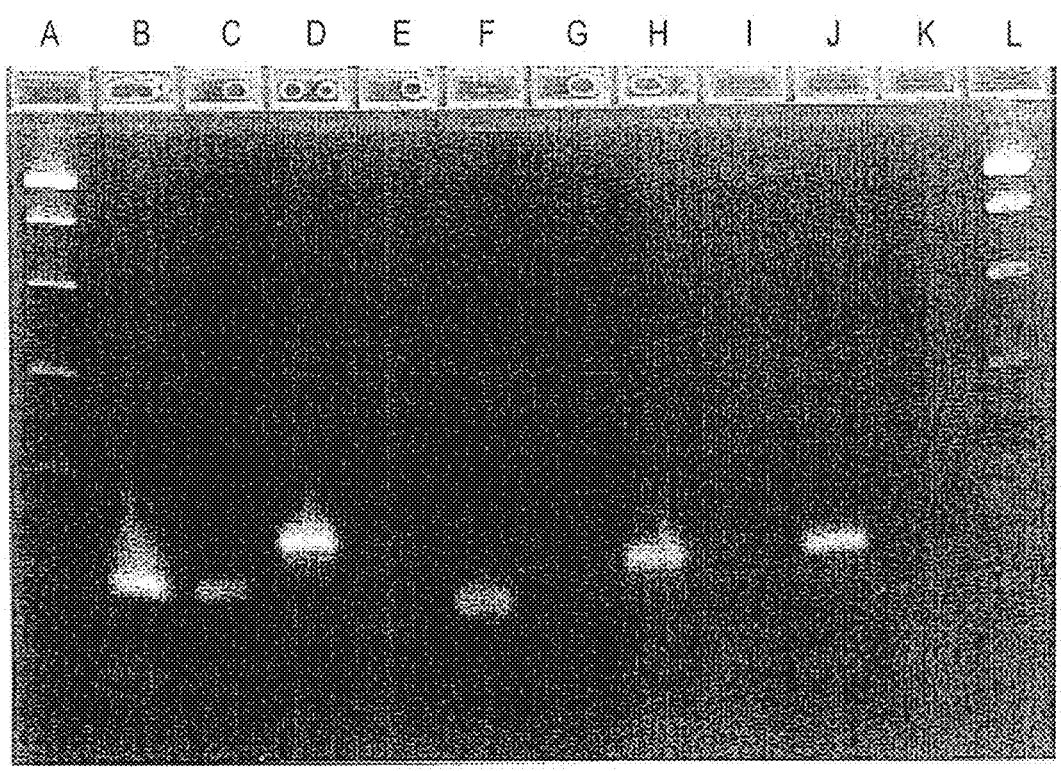

FIG. 9: depicts a photograph of a non-denaturing agarose gel, showing a decrease in secondary amplicons due to the presence of an exemplary DNA polymerase inhibitor, as described in Example 4.

Figure 10A:
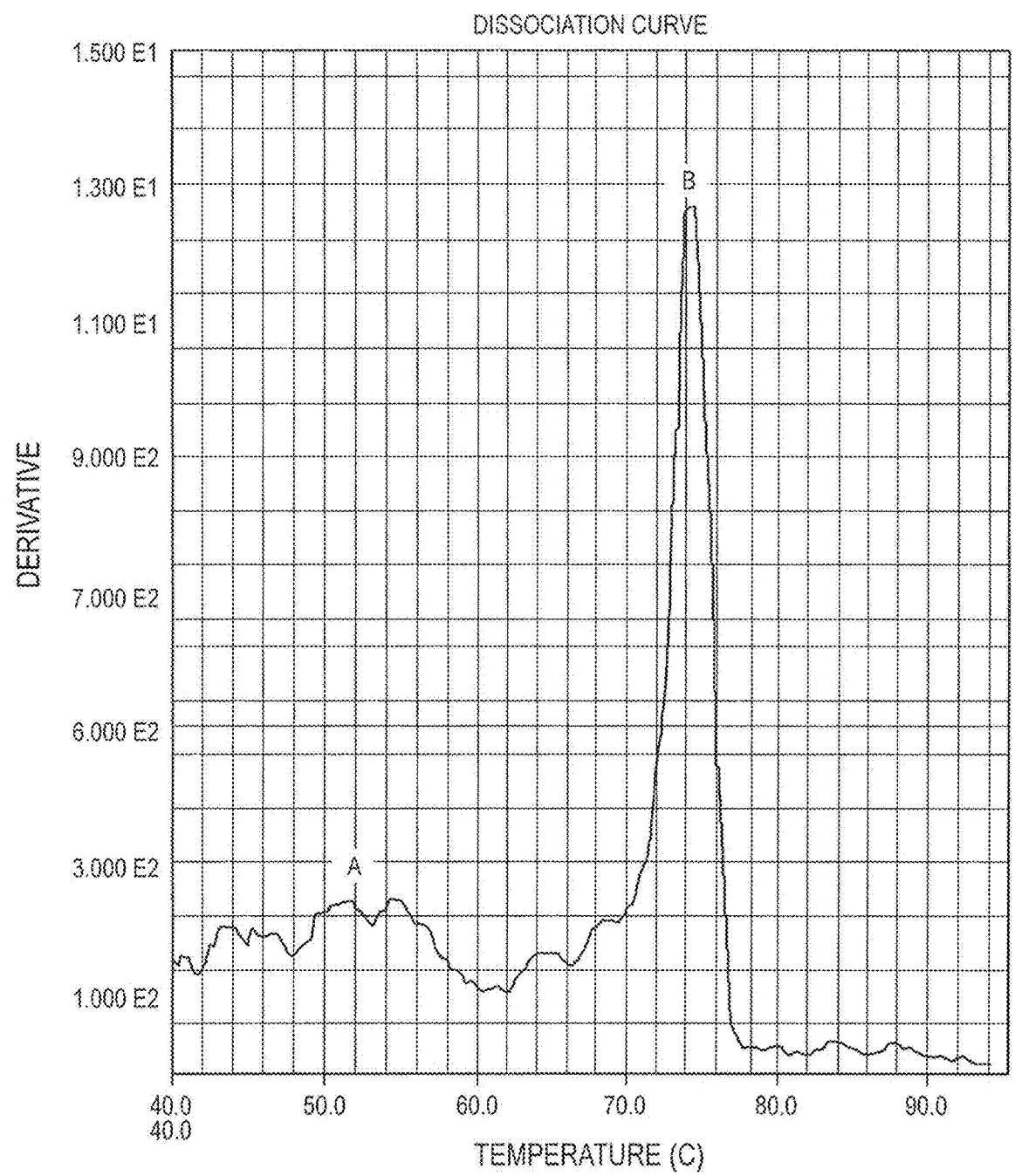
Figure 10B:
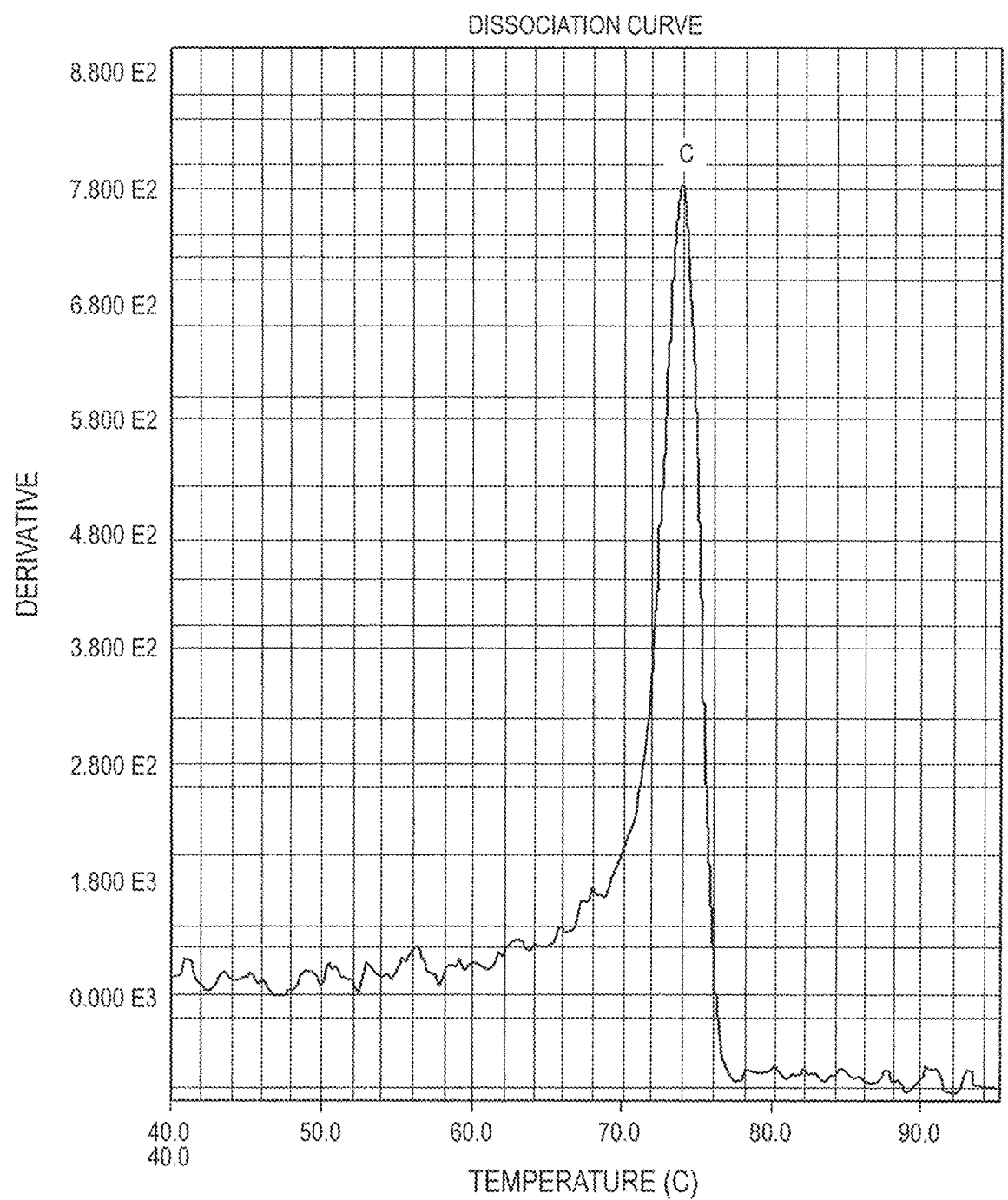

FIGS. 10A and 10B: depicts exemplary dissociation curves generated according to an exemplary method of the current teachings, as described in Example 5.

DESCRIPTION OF EXEMPLARY EMBODIMENTS

It is to be understood that both the foregoing general description and the following detailed description are exemplary and explanatory only and are not intended to limit the scope of the current teachings. As used in this specification, the word "a" or "an" means at least one, unless specifically stated otherwise. In this specification, the use of the singular includes the plural unless specifically stated otherwise. For example but not as a limitation, "a target nucleic acid" means that more than one target nucleic acid can be present; for example, one or more copies of a particular target nucleic acid species, as well as two or more different species of target nucleic acid. Also, the use of "comprise", "comprises", "comprising", "contain", "contains", "containing", "include", "includes", and "including" are not intended to be limiting. The term "and/or" means that the terms before and after can be taken together or separately. For illustration purposes, but not as a limitation, "X and/or Y" can mean "X" or "Y" or "X and Y".

The section headings used herein are for organizational purposes only and are not to be construed as limiting the described subject matter in any way. All literature cited in this specification, including but not limited to, patents, patent applications, articles, books, and treatises are expressly incorporated by reference in their entirety for any purpose. In the event that any of the incorporated literature contradicts any term defined in this specification, this specification controls. While the present teachings are described in conjunction with various embodiments, it is not intended that the present teachings be limited to such embodiments. On the contrary, the present teachings encompass various alternatives, modifications, and equivalents, as will be appreciated by those of skill in the art.

U.S. patent application Ser. No. 10/762,222, entitled "Competitive Kinetic Nucleic Acid DNA polymerase Inhibitors", by John W. Brandis, filed Jan. 11, 2004, is hereby expressly incorporated by reference in its entirety for any purpose.

SOME DEFINITIONS

The term "absorb at least some of" when used in reference to the fluorescent signal emitted from a nucleic acid dye refers to the reduction of detectable fluorescence due to the presence of one or more quenchers of an enzyme inhibitor. To absorb at least some of the fluorescence emitted by the nucleic acid dye associated with double-stranded segments of an enzyme inhibitor means that there is a measurable decrease in detectable fluorescence at the emission wavelength that is characteristic of the nucleic acid dye relative to the detectable fluorescence in a reaction composition comprising the same components except that the enzyme inhibitor does not comprise the quencher. In some embodiments, a measurable decrease in detectable fluorescence means a 30%, a 40%, a 50%, a 60%, a 70%, an 80%, a 90%, a 95%, a 97%, a 98%, a 99%, or a greater than a 99% relative decrease in fluorescence. In certain embodiments wherein the at least one quencher comprises a fluorescent quencher, there can be a measurable decrease in the detectable fluorescence at the wavelength that is characteristic of the nucleic acid dye and a measurable increase in the detectable fluorescence at the characteristic emission wavelength of at least one fluorescent quencher of the enzyme inhibitor.

The terms "amplicon" and "amplification product" as used herein generally refers to the product of an amplification reaction. An amplicon can be double-stranded or single-stranded, and can include the separated component strands obtained by denaturing a double-stranded amplification product. In some embodiments, an amplicon comprises a ligation product (for example but not limited to a ligated probe), the complement of at least part of a ligation product, or both. In certain embodiments, the amplicon of one amplification cycle can serve as a template in a subsequent amplification cycle.

The terms "annealing" and "hybridizing", including without limitation variations of the root words hybridize and anneal, are used interchangeably and mean the nucleotide base-pairing interaction of one nucleic acid with another nucleic acid that results in the formation of a duplex, triplex, or other higher-ordered structure. In some embodiments of the present teachings, annealing or hybridization refers to the interaction between at least some of the nucleotides in at least two regions of the same enzyme inhibitor to form a hairpin or stem-loop structure, sometimes referred to as self-annealing. The primary interaction is typically nucleotide base specific, e.g., A:T, A:U, and G:C, by Watson-Crick and Hoogsteen-type hydrogen bonding. In certain embodiments, base-stacking and hydrophobic interactions may also contribute to duplex stability. Conditions under which primers and probes anneal to complementary sequences are well known in the art, e.g., as described in Nucleic Acid Hybridization, A Practical Approach, Hames and Higgins, eds., IRL Press, Washington, D.C. (1985) and Wetmur and Davidson, Mol. Biol. 31:349, 1968. In general, whether such annealing takes place is influenced by, among other things, the length of the complementary portions of the corresponding first and third regions and/or fourth and sixth regions of certain enzyme inhibitors, the complementary portions of the primers and their corresponding binding sites in the target flanking sequences and/or amplicons, the complementary portions of the cleavage probes or the ligation probes and the corresponding binding portions of the target nucleic acid or amplicon, or the corresponding complementary portions or a reporter probe and its binding site; the pH; the temperature; the presence of mono- and divalent cations; the proportion of G and C nucleotides in the hybridizing region; the viscosity of the medium; and the presence of denaturants. Such variables influence the time required for hybridization. In certain enzyme inhibitor embodiments, the presence of certain nucleotide analogs or minor groove binders in the inhibitor, probes, and/or primers can also influence hybridization conditions. Thus, the preferred annealing conditions will depend upon the particular application. Such conditions, however, can be routinely determined by persons of ordinary skill in the art, without undue experimentation. Preferably, annealing conditions are selected to allow the primers and/or probes to selectively hybridize with a complementary sequence in the corresponding target flanking sequence or amplicon, but not hybridize to any significant degree to different target nucleic acids or non-target sequences in the reaction composition at the second reaction temperature.

The term "selectively hybridize" and variations thereof means that, under appropriate stringency conditions, a given sequence (for example but not limited to a primer) anneals with a second sequence comprising a complementary string of nucleotides (for example but not limited to a target flanking sequence or a primer-binding site of an amplicon), but does not anneal to undesired sequences, such as non-target nucleic acids, probes, or other primers. Typically, as the reaction temperature increases toward the melting temperature of a particular double-stranded sequence, the relative amount of selective hybridization generally increases and mis-priming generally decreases. In this specification, a statement that one sequence hybridizes or selectively hybridizes with another sequence encompasses situations where the entirety of both of the sequences hybridize or selectively hybridize to one another, and situations where only a portion of one or both of the sequences hybridizes or selectively hybridizes to the entire other sequence or to a portion of the other sequence.

As used herein, the term "stringency" is used to define the temperature and solvent composition existing during hybridization and the subsequent processing steps at which a hybrid comprised of two complementary nucleotide sequences will form. Stringency also defines the amount of homology, the conditions necessary, and the stability of hybrids formed between two nucleotide sequences. As the stringency conditions increase, selective hybridization is favored and non-specific cross-hybridization is disfavored. Increased stringency conditions typically correspond to higher incubation temperatures, lower salt concentrations, and/or higher pH, relative to lower stringency conditions at which mis-priming, including without limitation, the mis-annealing of ligation probes and/or cleavage probes, is more likely to occur. Those in the art understand that appropriate stringency conditions to enable the selective hybridization of a primer or primer pair, a ligation probe pair, and/or a cleavage probe pair to a corresponding target flanking sequence and/or amplicon can be routinely determined using well known techniques and without undue experimentation (see, e.g., PCR: The Basics from background to bench, McPherson and Moller, Bios Scientific Publishers (2000; hereinafter "McPherson")).

In this specification, a statement that one nucleic acid sequence is the same as or substantially the same as another nucleotide sequence encompasses situations where both of the nucleotide sequences are completely the same as or substantially the same as the other sequence, and situations where only a portion of one of the sequences is the same as or substantially the same as a portion of the entire other sequence. Likewise, a statement that one nucleic acid sequence is complementary to or substantially complementary to another nucleotide sequence encompasses situations where both of the nucleotide sequences are completely complementary or substantially complementary to one another, and situations where only a portion of one of the sequences is complementary to or substantially complementary to a portion of the entire other sequence.

The term "aptamer" as used herein refers to a DNA or RNA oligonucleotide that: 1) is typically identified originally using an in vitro selection process, for example but not limited to the "systematic evolution of ligands by exponential enrichment" (SELEX) process or a variation thereof, and 2) recognizes and binds to a binding partner, for example but not limited to an enzyme, in a highly specific, conformation-dependent manner.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, ACB, CBA, BCA, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the terms "complementary" and "complementarity" are used in reference to at least two nucleic acids that are related by the base-pairing rules. For example but without limitation, the sequence "A-C-T" is complementary to the sequence "T-G-A." Complementarity may be partial, in which case only some of the nucleotides are matched according to the base-pairing rules. Or, there may be complete or total complementarity between the nucleic acids. The degree of complementarity between nucleic acid strands has a significant effect on the efficiency and strength of hybridization between the nucleic acid strands. Complementarity need not be total for a stable duplex to form, i.e., stable duplexes may contain mismatched base pairs or unmatched bases. Those in the art can determine duplex stability empirically considering a number of variables including without limitation, the length of the nucleic acid, base composition and sequence of the nucleic acid, ionic strength, and incidence of mismatched base pairs. The stability of a nucleic acid duplex is typically measured by its melting temperature.

As used herein, the terms "complex" and "enzyme inhibitor-enzyme complex" refer to the association between an enzyme inhibitor of the present teachings and the corresponding enzyme. In some embodiments, an enzyme inhibitor-enzyme complex comprises a DNA polymerase, an RNA polymerase, a ligase, a cleaving enzyme, or a helicase. The terms inhibit, inhibits, and variations thereof, when used in reference to an enzyme, are relative terms and refer to a measurable decrease in enzymatic activity compared to the activity of the enzyme under the same amplifying conditions but in the absence of the enzyme inhibitor. In certain embodiments, the enzymatic activity of the enzyme is decreased by about 40%, about 50%, about 60%, about 70%, about 80%, about 85%, about 90%, about 95%, about 96%, about 97%, about 98%, about 99%, or greater than 99%, when complexed with the enzyme inhibitor, as determined by the quantity of desired amplicon generated in parallel amplification reactions in the presence and the absence of the enzyme inhibitor. In certain embodiments, optimal inhibition is obtained when the complex further comprises an accessory protein, a NTP, a nucleotide analog, a substance comprising NAD+, or combinations thereof.

The term "corresponding" as used herein refers to at least one specific relationship between the elements to which the term relates. For illustration purposes but not as a limitation, at least one forward primer of a particular primer pair corresponds to at least one reverse primer of the same primer pair; at least one primer is designed to anneal with the flanking region of the corresponding target nucleic acid and/or the primer-binding portion of at least one corresponding amplicon; a first probe of a ligation probe set anneals to a target nucleic acid and/or an amplicon upstream of, and typically adjacent to, the ligation site and the corresponding second ligation probe anneals to the target nucleic acid and/or an amplicon downstream of, and typically adjacent to, the ligation site; in certain enzyme inhibitor embodiments, a first oligonucleotide anneals with the corresponding second oligonucleotide to form a duplex comprising at least one double-stranded segment; and so forth.

The terms "denaturing" and "denaturation" as used herein refer to any process in which a double-stranded polynucleotide, including without limitation, a gDNA fragment comprising at least one target nucleic acid, a double-stranded amplicon, or a polynucleotide comprising at least one double-stranded segment, for example but not limited to an enzyme inhibitor at a first temperature, is converted to two single-stranded polynucleotides or to a single-stranded or substantially single-stranded polynucleotide, as appropriate. Denaturing a double-stranded polynucleotide or a double-stranded segment of an enzyme inhibitor includes without limitation, a variety of thermal and chemical techniques which render a double-stranded nucleic acid or a double-stranded segment of an enzyme inhibitor single-stranded or substantially single-stranded, for example but not limited to, releasing the two individual single-stranded components of a double-stranded polynucleotide or a duplex comprising two oligonucleotides. Those in the art will appreciate that the denaturing technique employed is generally not limiting unless it substantially interferes with a subsequent annealing or enzymatic step of an amplification reaction or, in certain methods, the detection of a fluorescent signal.

The term "double-stranded," as used herein refers to one or two nucleic acid strands that have hybridized along at least a portion of their lengths. Thus, in certain contexts, "double-stranded" can refer to a portion of a single oligonucleotide that can fold so that at least one segment of the first region of the oligonucleotide hybridizes to at least one segment of the third region of the same oligonucleotide, at least one segment of the fourth region of the oligonucleotide hybridizes with at least one segment of the sixth region of the oligonucleotide, or both, thereby forming one or more double-stranded segments and one or more single-stranded portions. Hence, a single nucleic acid strand can form hairpin or stem-loop conformations that have double-stranded and single-stranded segments (see, e.g., FIG. 1). Similarly, two complementary oligonucleotides can hybridize with each other to form a duplex (see, e.g., FIG. 2). Hence, "double-stranded" does not mean that a nucleic acid must be entirely double-stranded. Instead, a double-stranded nucleic acid can have one or more single-stranded segment and one or more double-stranded segment.

The term "first temperature" refers to the temperature, often a range of temperatures, at which an enzyme-enzyme inhibitor complex can form. The term "second temperature" refers to the temperature, often a range of temperatures, at which an enzyme-enzyme inhibitor complex dissociates or does not form. As those in the art will appreciate, the second temperature is typically at or near the Tm of the enzyme inhibitor, while the first temperature is typically below the Tm of the enzyme inhibitor to allow the enzyme inhibitor to assume a conformation comprising at least one double-stranded segment. An exemplary first temperature can be ambient or "room temperature".

As used herein, the term "Tm" is used in reference to melting temperature. The melting temperature is the temperature at which a population of double-stranded nucleic acid molecules becomes half dissociated into single strands.

A "microfluidics device" is a reaction vessel comprising at least one microchannel, generally including an internal dimension of one millimeter or less. Microfluidics devices typically employ very small reaction volumes, often on the order of one or a few microliters (μL), nanoliters, or picoliters. Those in the art will appreciate that the size, shape, and composition of a microfluidics device is generally not a limitation of the current teachings. Rather, any suitable microfluidics devices can be employed in performing one or more steps of the disclosed methods. Descriptions of exemplary microfluidics devices and uses thereof can be found in, among other places, Fiorini and Chiu, BioTechniques 38:429-46 (2005); Kelly and Woolley, Analyt. Chem. 77(5): 96A-102A (2005); Cheuk-Wai Kan et al., Electrophoresis 25:3564-88 (2004); and Yeun et al., Genome Res. 11:405-12 (2001).

The term "minor groove binder" as used herein refers to a small molecule that fits into the minor groove of double-stranded DNA, sometimes in a sequence specific manner. Generally, minor groove binders are long, flat molecules that can adopt a crescent-like shape and thus, fit snugly into the minor groove of a double helix, often displacing water. Minor groove binding molecules typically comprise several aromatic rings connected by bonds with torsional freedom, for example but not limited to, furan, benzene, or pyrrole rings.

"Mis-priming" or "mis-primed," as used herein, refer to the hybridization of a primer or a probe to a non-target nucleic acid. As is known in the art, primers (excluding random primers) are generally designed to hybridize to a selected sequence that flanks a target nucleic acid or to a primer-binding site of an amplicon and to direct DNA synthesis or primer extension starting at that site. Mis-priming can occur when a primer or a probe hybridizes to a non-target nucleic acid, oftentimes at low or decreased stringency conditions, and then serves as the initiation point for primer extension from that non-target site, giving rise to synthesis of certain undesired secondary amplification products. Ligation probe pairs and cleavage probe pairs can also mis-anneal to a non-target nucleic acid, oftentimes at low or decreased stringency conditions, which can also result in the formation of undesired amplification products.

The term "non-extendable nucleotide" as used herein refers to a nucleotide to which substantially no other nucleotide can be added by a polymerase. In some embodiments, the non-extendable nucleotides are nucleotide analogs that do not have optimal functional groups for formation of a phosphodiester linkage with another nucleotide. In certain embodiments, the non-extendable nucleotides are chain-terminating nucleotides that allow essentially no primer extension, for example dideoxynucleotides (ddNs), such as ddA, ddC, ddG, ddI, ddT, and ddU. In some embodiments, a polymerase can link other nucleotides to the non-extendable nucleotide, but at slow rate.

The terms "non-specific" or "background" when used in reference to fluorescence refer to the detectable signal emitted from nucleic acid dye molecules associated with double-stranded nucleic acids other than desired amplicons. Desired amplicons comprise the amplification products of target nucleic acids, including in some embodiments, internal standard or control sequences that may be included in certain reaction compositions of the current teachings for, among other things, normalization and/or quantitation purposes. Thus, the fluorescent signal resulting from the association of nucleic acid dye molecules with spurious, secondary amplicons, often the result of mispriming, misligation, and/or primer dimer formation, is one source of non-specific fluorescence. Those in the art will appreciate that when the enzyme inhibitors of the present teachings comprise at least one double-stranded segment at a first temperature to which nucleic acid dye molecules can associate, the inhibitor's quencher moiety can absorb at least some of the detectable fluorescent signal from the associated nucleic acid dye, a second source of background, thereby reducing the non-specific fluorescence of the reaction composition.

The term "nucleotide base", sometimes referred to as a nitrogenous base or a nitrogen heterocyclic base, refers to a substituted or unsubstituted aromatic ring or rings that can serve as a component of a nucleotide. In certain embodiments, the aromatic ring or rings contain a nitrogen atom. In certain embodiments, the nucleotide base is capable of forming Watson-Crick or Hoogsteen-type hydrogen bonds with a complementary nucleotide base. Exemplary nucleotide bases and analogs thereof include, the naturally-occurring nucleotide bases adenine, guanine, cytosine, 5 methylcytosine, uracil, and thymine, and analogs of the naturally occurring nucleotide bases, including, 7-deazaadenine, 7-deazaguanine, 7-deaza-8-azaguanine, 7-deaza-8-azaadenine, N6-Δ2-isopentenyladenine (6iA), N6-Δ2-isopentenyl-2-methylthioadenine (2ms6iA), N2-dimethylguanine (dmG), 7-methylguanine (7mG), inosine, nebularine, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, pyrazolo[3,4-D]pyrimidines (see, e.g., U.S. Pat. Nos. 6,143,877 and 6,127,121 and PCT Published Application WO 01/38584), ethenoadenine, indoles such as nitroindole and 4-methylindole, and pyrroles such as nitropyrrole. Non-limiting examples of nucleotide bases can be found, e.g., in Fasman, Practical Handbook of Biochemistry and Molecular Biology, pp. 385-394, CRC Press, Boca Raton, Fla. (1989) and the references cited therein.

The term "nucleotide" as used herein refers to a phosphate ester of a nucleoside, e.g., a triphosphate ester, wherein the most common site of esterification is the hydroxyl group attached to the C-5 position of the pentose. The term "nucleotide" is also used to generally refer to a set of compounds including both nucleosides and nucleotides, unless otherwise apparent from the context. The term "nucleoside", as used herein, refers to a compound comprising a nucleotide base linked to the C-1' carbon of a sugar, such as ribose, arabinose, xylose, and pyranose, and sugar analogs thereof. The sugar may be substituted or unsubstituted. Substituted ribose sugars include, but are not limited to, those riboses in which one or more of the carbon atoms, for example the 2'-carbon atom, is substituted with one or more of the same or different, —R, —OR, —NR$_2$ azide, cyanide or halogen groups, where each R is independently H, C$_1$-C$_6$ alkyl, C$_2$-C$_7$ acyl, or C$_5$-C$_{14}$ aryl. Exemplary riboses include, but are not limited to, 2'-(C$_1$-C$_6$)alkoxyribose, 2'-(C$_5$-C$_{14}$)aryloxyribose, 2',3'-didehydroribose, 2'-deoxy-3'-haloribose, 2'-deoxy-3'-fluororibose, 2'-deoxy-3'-chlororibose, 2'-deoxy-3'-aminoribose, 2'-deoxy-3'-(C$_1$-C$_6$) alkylribose, 2'-deoxy-3'-(C$_1$-C$_6$)alkoxyribose and 2'-deoxy-3'-(C$_5$-C$_{14}$)aryloxyribose, ribose, 2'-deoxyribose, 2',3'-dideoxyribose, 2'-haloribose, 2'-fluororibose, 2'-chlororibose, and 2'-alkylribose, e.g., 2'-O-methyl, 4'-α-anomeric nucleotides, 1'-α-anomeric nucleotides, 2'-4'- and 3'-4'-linked and other "locked" or "LNA", bicyclic sugar modifications (see, e.g., PCT Published Application Nos. WO 98/22489, WO 98/39352, and WO 99/14226; and Braasch and Corey, Chem. Biol. 8:1-7, 2001; and U.S. Pat. No. 6,268,490). "LNA" or "locked nucleic acid" is a nucleotide analog that is conformationally locked such that the ribose ring is constrained by a methylene linkage between, for example but not limited to, the 2'-oxygen and the 3'- or 4'-carbon or a 3'-4' LNA with a 2'-5' backbone (see, e.g., Imanishi and Obika, U.S. Pat. No. 6,268,490; and Wengel and Nielsen, U.S. Pat. No. 6,670,461). The conformation restriction imposed by the linkage often increases binding affinity for complementary sequences and increases the thermal stability of such duplexes. Exemplary LNA sugar analogs within a polynucleotide include the structures:

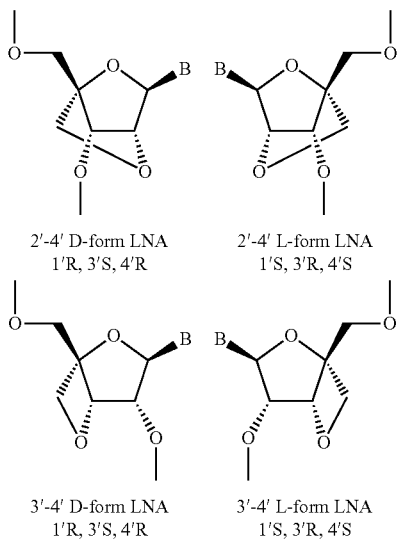

where B is any nucleotide base.

The 2'- or 3'-position of ribose can be modified to include hydrogen, hydroxy, methoxy, ethoxy, allyloxy, isopropoxy, butoxy, isobutoxy, methoxyethyl, alkoxy, phenoxy, azido, cyano, amido, imido, amino, alkylamino, fluoro, chloro and bromo. Nucleotides include the natural D optical isomer, as well as the L optical isomer forms (see, e.g., Garbesi et al., Nucl. Acids Res. 21:4159-65 (1993); Fujimori et al., J. Amer. Chem. Soc. 112:7436-38 (1990); Urata et al., Nucl. Acids Symposium Ser. No. 29:69-70 (1993)). When the nucleotide base is a purine, e.g., A or G, the ribose sugar is attached to the N$^9$-position of the nucleotide base. When the nucleotide base is a pyrimidine, e.g. C, T, or U, the pentose sugar is attached to the N$^1$-position of the nucleotide base, except for pseudouridines, in which the pentose sugar is attached to the C5 position of the uracil nucleotide base (see, e.g., Kornberg and Baker, DNA Replication, 2$^{nd}$ Ed. (1992), Freeman, San Francisco, Calif.).

One or more of the pentose carbons of a nucleotide may be substituted with a phosphate ester having the formula:

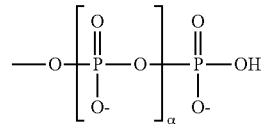

where α is an integer from 0 to 4. In certain embodiments, a is 2 and the phosphate ester is attached to the 3'- or 5'-carbon of the pentose. In certain embodiments, the nucleotides are those in which the nucleotide base is a purine, a 7-deazapurine, a pyrimidine, or an analog thereof. The term "nucleotide 5'-triphosphate" refers to a nucleotide with a triphosphate ester group at the 5' position, and is sometimes denoted as "rNTP", or "dNTP" and "ddNTP" to particularly point out the structural features of the ribose sugar, or generically as "NTP". The triphosphate ester group may include sulfur substitutions for the various oxygens, e.g., α-thio-nucleotide 5'-triphosphates. Reviews of nucleotide chemistry can be found in, among other places, Miller, Bioconjugate Chem. 1:187-91 (1990); Shabarova, Z. and Bogdanov, A. Advanced Organic Chemistry of Nucleic Acids, VCH, New York (1994); and Nucleic Acids in Chemistry and Biology, 2d ed., Blackburn and Gait, eds., Oxford University Press (1996; hereinafter "Blackburn and Gait").

The term "nucleotide analogs" refers to synthetic analogs having modified nucleotide base portions, modified pentose portions, and/or modified phosphate portions, and, in the case of polynucleotides, modified internucleotide linkages, as generally described herein and elsewhere (e.g., Scheit, Nucleotide Analogs, John Wiley, New York, 1980; Englisch, Angew. Chem. Int. Ed. Engl. 30:613-29, 1991; Agarwal, Protocols for Polynucleotides and Analogs, Humana Press, 1994; and S. Verma and F. Eckstein, Ann. Rev. Biochem. 67:99-134, 1998). Generally, modified phosphate portions comprise analogs of phosphate wherein the phosphorous atom is in the +5 oxidation state and one or more of the oxygen atoms is replaced with a non-oxygen moiety, for example but not limited to, sulfur. Some non-limiting examples of phosphate analogs include phosphorothioate, phosphorodithioate, phosphoroselenoate, phosphorodiselenoate, phosphoroanilothioate, phosphoranilidate, phosphoramidate, boronophosphates, including associated counterions, e.g., H$^+$, NH$_4^+$, Na$^+$, if such counterions are present. Non-limiting examples of modified nucleotide base portions include 5-methylcytosine (5mC); C-5-propynyl analogs, including but not limited to, C-5 propynyl-C and C-5 propynyl-U; 2,6-diaminopurine, also known as 2-amino adenine or 2-amino-dA; hypoxanthine, pseudouridine, 2-thiopyrimidine, isocytosine (isoC), 5-methyl isoC, and isoguanine (isoG; see, e.g., U.S. Pat. No. 5,432,272). Non-limiting examples of modified pentose portions include LNA analogs including without limitation Bz-A-LNA, 5-Me-Bz-C-LNA, dmf-G-LNA, and T-LNA (see, e.g., The Glen Report, 16(2):5 (2003); Koshkin et al., Tetrahedron 54:3607-30 (1998)), and 2'- or 3'-modifications where the 2'- or 3'-position is hydrogen, hydroxy, alkoxy (e.g., methoxy, ethoxy, allyloxy, isopropoxy, butoxy, isobutoxy and phenoxy), azido, amino, alkylamino, fluoro, chloro, or bromo. Modified internucleotide linkages include phosphate analogs, analogs having achiral and uncharged intersubunit linkages (e.g., Sterchak, E. P. et al., Organic Chem. 52:4202 (1987)), and uncharged morpholino-based polymers having achiral intersubunit linkages (see, e.g., U.S. Pat. No. 5,034,506). Some non-limiting examples of internucleotide linkage analogs include morpholidate, acetal, and polyamide-linked heterocycles. In one class of nucleotide analogs, known as peptide nucleic acids, including without limitation pseudocomplementary peptide nucleic acids (collectively "PNA"), a conventional sugar and internucleotide linkage has been replaced with a 2-aminoethylglycine amide backbone polymer (see, e.g., Nielsen et al., Science, 254:1497-1500 (1991); Egholm et al., J. Am. Chem. Soc., 114: 1895-1897 (1992); Demidov et al., Proc. Natl. Acad. Sci. 99:5953-58 (2002); Peptide Nucleic Acids: Protocols and Applications, Nielsen, ed., Horizon Bioscience (2004)). A wide range of nucleotide analogs for use in enzymatic incorporation or chemical synthesis are available as triphosphates, phosphoramidates, or CPG derivatives from, among other sources, Glen Research, Sterling, Md.; Link Technologies, Lanarkshire, Scotland, UK; and TriLink BioTechnologies, San Diego, Calif. Descriptions of oligonucleotide synthesis and certain nucleotide analogs, can be found in, among other places, S. Verma and F. Eckstein, Ann. Rev. Biochem. 67:99-134 (1999); Goodchild, Bioconj. Chem. 1:165-87 (1990); Current Protocols in Nucleic Acid Chemistry, Beaucage et al., eds., John Wiley & Sons, New York, N.Y., including updates through August 2005 (hereinafter "Beaucage et al."); and Blackburn and Gait.

As used herein, the term "primer-binding site" refers to a region of a polynucleotide sequence, typically a target nucleic acid and/or an amplicon that can serve directly, or by virtue of its complement, as the template upon which a primer can anneal for any suitable primer extension reaction known in the art, for example but not limited to, PCR. It will be appreciated by those of skill in the art that when two primer-binding sites are present on a single polynucleotide, the orientation of the two primer-binding sites is generally different. For example, one primer of a primer pair is complementary to and can hybridize with to the first primer-binding site, while the corresponding primer of the primer pair is designed to hybridize with the complement of the second primer-binding site. Stated another way, in some embodiments the first primer-binding site can be in a sense orientation, and the second primer-binding site can be in an antisense orientation. A primer-binding site of an amplicon may, but need not comprise the same sequence as or at least some of the sequence of the target flanking sequence or its complement.

Those in the art understand that as a target nucleic acid and/or an amplification product is amplified by certain amplification means, the complement of the primer-binding site is synthesized in the complementary amplicon or the complementary strand of the amplicon. Thus, it is to be understood that the complement of a primer-binding site is expressly included within the intended meaning of the term primer-binding site, as used herein.

As used herein, the term "probe-binding site" refers to a region of a polynucleotide sequence, typically a target nucleic acid and/or an amplicon that can serve directly, or by virtue of its complement, as the template upon which probe can anneal. It will be appreciated by those of skill in the art that the probe-binding site for a ligation probe pair comprise an upstream probe-binding site and a downstream probe binding site and that these two sites are typically adjacent to each other. In certain embodiments, the upstream ligation probe-binding site and the downstream probe-binding site are not adjacent to each other and an amplifying step can comprises a gap-filling reaction. It will also be appreciated by those of skill in the art that the probe-binding site for a cleavage probe pair comprises an upstream probe-binding site that is adjacent to, and may but need not overlap at least part of the downstream cleavage probe-binding site.

Those in the art understand that as a target nucleic acid and/or an amplification product is amplified by certain amplification means, the complement of the probe-binding site is synthesized in the complementary amplicon or the complementary strand of the amplicon. Thus, it is to be understood that the complement of a probe-binding site is expressly included within the intended meaning of the term probe-binding site, as used herein.

As used herein, the terms "polynucleotide", "oligonucleotide", and "nucleic acid" are used interchangeably and refer to single-stranded and double-stranded polymers of nucleotide monomers, including without limitation 2'-deoxyribonucleotides (DNA) and ribonucleotides (RNA) linked by internucleotide phosphodiester bond linkages, or internucleotide analogs, and associated counter ions, e.g., $H^+$, $NH_4^+$, trialkylammonium, $Mg^{2+}$, $Na^+$, and the like. A polynucleotide may be composed entirely of deoxyribonucleotides, entirely of ribonucleotides, or chimeric mixtures thereof and can include nucleotide analogs. The nucleotide monomer units may comprise any of the nucleotides described herein, including, but not limited to, nucleotides and/or nucleotide analogs. Polynucleotides typically range in size from a few monomeric units, e.g. 5-40 when they are sometimes referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, "T" denotes thymidine, and "U" denotes deoxyuridine, unless otherwise noted.

The term "quencher" as used herein refers to a moiety that absorbs at least some of the intensity of a fluorescent emission. Quenchers can be categorized as fluorescent quenchers and dark quenchers (sometimes also referred to as non-fluorescent quenchers). A fluorescent quencher is a moiety, typically a fluorophore, that can absorb the fluorescent signal emitted from a source of fluorescence at a first wavelength, for example but not limited to, a nucleic acid dye associated with a double-stranded segment of nucleic acid, and after absorbing enough fluorescent energy, the fluorescent quencher can emit fluorescence at a second wavelength that is characteristic of the quencher, a process termed "fluorescent resonance energy transfer" or FRET. For example but not as a limitation, the FAM fluorophore associated with a TAMRA fluorescent quencher can be illuminated at 492 nm, the excitation peak for FAM, and emit fluorescence at 580 nm, the emission peak for TAMRA. A dark quencher, appropriately paired with a source of fluorescence, absorbs the fluorescent energy from the source, but does not itself fluoresce. Rather, the dark quencher dissipates the absorbed energy, typically as heat. In certain embodiments, a dark quencher comprises a chromophore that acts as an energy transfer acceptor from a fluorescent source, such as a nucleic acid dye associated with a double-stranded segment of an enzyme inhibitor of the present teachings, but does not emit a detectable fluorescent signal of its own. Non-limiting examples of dark or non-fluorescent quenchers include DABCYL (4-(4'-dimethylaminophenylazo) sulfonic acid); Black Hole Quenchers series quenchers, for example but not limited to BHQ-1, BHQ-2, and BHQ-3; Iowa Black; QSY series quenchers, for example but not limited to QSY-7; AbsoluteQuencher; Eclipse non-fluorescent quencher; nanocrystals for example but not limited to quantum dots; metals such as gold nanoparticles; and the like.

As used herein, the term "reaction vessel" generally refers to any container, chamber, device, or assembly, in which a reaction can occur in accordance with the present teachings. In some embodiments, a reaction vessel can be a microtube, for example but not limited to a 0.2 mL or a 0.5 mL reaction tube such as a MicroAmp® Optical tube (Applied Biosystems) or a micro-centrifuge tube, or other containers of the sort in common practice in molecular biology laboratories. In some embodiments, a reaction vessel comprises a well of a multi-well plate, a spot on a glass slide, or a channel or chamber of a microfluidics device, including without limitation an Applied Biosystems TaqMan Low Density Array. For example but not as a limitation, a plurality of reaction vessels can reside on the same support. In some embodiments, lab-on-a-chip like devices, available for example from Caliper and Fluidgm, can serve as reaction vessels in the disclosed methods. It will be recognized that a variety of reaction vessels are commercially available or can be designed for use in the context of the present teachings.

The term "reporter group" is used in a broad sense herein and refers to any identifiable tag, label, or moiety.

The term "small RNA molecule" is used in a broad sense herein and refers to any nucleic acid sequence comprising ribonucleotides that are non-coding and typically have a length of: 150 nucleotides or less, 100 nucleotides or less, 75 nucleotides or less, 30 nucleotides or less, between 19 and 27 nucleotides, and between 21 and 23 nucleotides. A small RNA molecule can be single-stranded, double-stranded, or can comprise at least one single-stranded region and at least one double-stranded region, including without limitation, stem-loop or hairpin structures. Non-limiting examples of small RNA molecules include untranslated functional RNA, non-coding RNA (ncRNA), small non-messenger RNA (snmRNA), small interfering RNA (siRNA), tRNA, tiny non-coding RNA (tncRNA), small modulatory RNA (smRNA), snoRNA, stRNA, snRNA, microRNA (miRNA) including without limitation miRNA precursors such as primary miRNA (pri-miRNA) and precursor miRNA (pre-miRNA), and small interfering RNA (siRNA) (see, e.g., Eddy, Nature Reviews Genetics 2:919-29 (2001); Storz, Science 296: 1260-63 (2002); Buckingham, Horizon Symposia: Understanding the RNAissance:1-3 (2003)). In certain embodiments, a target nucleic acid comprises a small RNA molecule. Those enzyme inhibitors of the current teachings that comprise ribonucleotides and/or ribonucleotide analogs are expressly excluded from the intended scope of the term small RNA molecule as used in this specification.

The term "thermostable" when used in reference to an enzyme, indicates that the enzyme is functional or active (i.e., can perform catalysis) at an elevated temperature, for example but not limited to, at about 55° C. or higher. Thermostable enzymes that may be suitable for use in the current teachings are commercially available from various vendors, including without limitation, Applied Biosystems (Foster City, Calif.), Promega (Madison, Wis.), Stratagene (LaJolla, Calif.), and New England BioLabs (Beverly, Mass.). Those in the art will understand that thermostable enzymes can be isolated from a variety of thermophilic and/or hyperthermophilic organisms, for example but not limited to, certain species of eubacteria and archaea, including without limitation, certain viruses that infect such organisms and that such thermostable enzymes may be suitable for use in the disclosed complexes, methods, and kits.

The terms "universal base" or "universal nucleotide" are generally used interchangeably herein and refer to a nucleotide analog that can substitute for more than one species of naturally-occurring nucleotide in a polynucleotide, including without limitation, an enzyme inhibitor. Universal bases typically contain an aromatic ring moiety that may or may not contain nitrogen atoms and generally use aromatic ring stacking to stabilize a duplex. In certain embodiments, a universal base may be covalently attached to the C-1' carbon of a pentose sugar to make a universal nucleotide. In certain embodiments, a universal base does not hydrogen bond specifically with another nucleotide base. In certain embodiments, a nucleotide base may interact with adjacent nucleotide bases on the same nucleic acid strand by hydrophobic stacking. Non-limiting examples of universal nucleotides and universal bases include deoxy-7-azaindole triphosphate (d7AITP), deoxyisocarbostyril triphosphate (dICSTP), deoxypropynylisocarbostyril triphosphate (dPICSTP), deoxymethyl-7-azaindole triphosphate (dM7AITP), deoxylmPy triphosphate (dim PyTP), deoxyPP triphosphate (dPPTP), deoxypropynyl-7-azaindole triphosphate (dP7AITP), 3-methyl isocarbostyril (MICS), 5-methyl isocarbyl (5MICS), imidazole-4-carboxamide, 3-nitropyrrole, 5-nitroindole, hypoxanthine, inosine, deoxyinosine, 5-fluorodeoxyuridine, 4-nitrobenzimidizole, and certain PNA-bases, including without limitation certain pseudocomplementary PNA (pcPNA) bases. Descriptions of universal bases can be found in, among other places, Loakes, Nucl. Acids Res. 29:2437-47 (2001); Berger et al., Nucl. Acids Res. 28:2911-14 (2000); Loakes et al., J. Mol. Biol. 270: 426-35 (1997); Verma and Eckstein, Ann. Rev. Biochem. 67:99-134 (1998); Published PCT Application No. US02/ 33619, and Patron and Pervin, U.S. Pat. No. 6,433,134.

When two different oligonucleotides anneal to different regions of the same linear complementary nucleic acid, and the 3'-end of one oligonucleotide faces or opposes the 5'-end of the other oligonucleotide, the former may be referred to as the "upstream" oligonucleotide and the latter the "downstream" oligonucleotide.

Certain Exemplary Components

The term "cleaving enzyme" refers to any polypeptide that can, when combined with a nucleic acid cleavage structure (sometimes referred to as an overlap flap structure or an invasive cleavage reaction substrate) and under appropriate conditions, cleave the non-annealed flap portion of the downstream cleavage probe to generate a structure comprising a ligatable nick. Non-limiting examples of cleaving enzymes include structure-specific nucleases, for example but not limited to, certain DNA polymerases from bacteria and bacteriophages, including isolated 5'exonuclease domains thereof; Cleavase® enzymes (Third Wave Technologies, Inc., Madison, Wis.); eukaryotic flap endonucleases; and archaeal flap endonucleases (see, e.g., Lyamichev et al., Science 260:778-83 (1993); Li et al., J. Biol. Chem. 270:22109-12 (1995); Wu et al., Nucl. Acids Res. 24:2036-43 (1996); Hosfield et al., J. Biol. Chem. 273: 27154-61 (1998); Kaiser et al., J. Biol. Chem. 274:21387-94 (1999); Allawi et al., J. Mol. Biol. 328:537-54 (2003); and U.S. Pat. Nos. 5,614,402 and 6,706,471).

A nucleic acid cleavage structure typically comprises a template strand (generally a target nucleic acid, a single-stranded amplicon, or a separated strand of a double-stranded amplicon) hybridized with a cleavage probe pair comprising two overlapping probes that hybridize with the template strand to form a "flap". The first or upstream cleavage probe comprises a sequence that is complementary with a first portion of the template strand and overlaps the 5'-end of the template-complementary sequence of the second or downstream cleavage probe, which comprises (1) a sequence that is complementary with a second portion of the template strand that is adjacent to the first portion of the template strand and (2) a 5'-region comprising at least one nucleotide that may or may not be complementary with the template strand, but when hybridized with the template strand, is displaced by the 3'-end of the upstream cleavage probe (see, e.g., Lyamichev et al., Nat. Biotechnol. 17:292-96 (1999), particularly FIG. 1; Neville et al., BioTechniques 32:S34-43 (2002), particularly FIG. 2 A; Allawi et al., J. Mol. Biol. 328:537-54 (2003), particularly FIG. 2; and Brow et al., U.S. Pat. No. 6,706,471, for example at FIGS. 32 and 65). Certain cleaving enzyme inhibitors of the present teachings are designed to assume a conformation at a first temperature that resembles or mimics a nucleic acid cleavage structure. Certain disclosed cleaving enzyme inhibitors can form a nucleic acid cleavage structure at a first temperature, but at least one oligonucleotide comprises at least one nucleotide analog and/or at least one internucleotide linkage that can not be cleaved or is slowly cleaved by the cleaving enzyme (an "uncleavable internucleotide linkage"). Non-limiting examples of uncleavable internucleotide linkages include phosphorothioates, including without limitation phosphorodithioates; methyl phosphonates; phosphoramidates; and boranophosphates.

A "ligase" is a polypeptide that, under appropriate conditions, catalyzes phosphodiester bond formation between the 3'-OH and the 5'-phosphate of adjacently hybridized probes, including without limitation, a first and second ligation probe of a ligation probe set or a first cleavage probe and the hybridized fragment of a second cleavage probe that has been cleaved by a cleaving enzyme. Temperature sensitive ligases, include but are not limited to, bacteriophage T4 ligase and *E. coli* ligase. Non-limiting examples of thermostable ligases include Afu ligase, Taq ligase, Tfl ligase, Mth ligase, Tth ligase, Tth HB8 ligase, Tsc ligase, *Thermus* species AK16D ligase, Ape ligase, $Lig_m$ ligase, Aae ligase, Rm ligase, and Pfu ligase (see, e.g., Housby et al., Nucl. Acids Res. 28:e10, 2000; Tong et al., Nucl. Acids Res. 28:1447-54, 2000; Nakatani et al., Eur. J. Biochem. 269: 650-56, 2002; and Sriskanda et al., Nucl. Acids Res. 11:2221-28, 2000). The skilled artisan will appreciate that any number of mesophilic, thermostable, and/or hyperthermophilic ligases, including DNA ligases and RNA ligases, can be obtained from mesophilic, thermophilic, or hyperthermophilic organisms, for example, certain species of eubacteria and archaea, and including certain viruses that infect such mesophilic, thermophilic, or hyperthermophilic organisms; and that such ligases may be suitable in the disclosed complexes, methods and kits.

The term "nucleic acid dye" as used herein refers to a fluorescent molecule that is specific for a double-stranded polynucleotide or that at least shows a substantially greater fluorescent enhancement when associated with double-stranded polynucleotide acid than with a single-stranded polynucleotide. Typically nucleic acid dye molecules associate with double-stranded segments of polynucleotides by intercalating between the base pairs of the double-stranded segment, by binding in the major or minor grooves of the double-stranded segment, or both. Non-limiting examples of nucleic acid dyes include ethidium bromide, DAPI, Hoechst derivatives including without limitation Hoechst 33258 and Hoechst 33342, intercalators comprising a lanthanide chelate (for example but not limited to a nalthalene diimide derivative carrying two fluorescent tetradentate β-diketone-Eu3+ chelates (NDI-$(BHHCT-Eu^{3+})_2$), see, e.g., Nojima et al., Nucl. Acids Res. Supplemnent No. 1, 105-06 (2001)), ethidium bromide, and certain unsymmetrical cyanine dyes such as SYBR Green®, PicoGreen®, and BOXTO.

The nucleic acid sequences of certain disclosed enzyme inhibitors comprise an aptamer. Aptamers bind target molecules in a highly specific, conformation-dependent manner, typically with very high affinity, although those in the art will understand that aptamers with lower binding affinity can be selected if desired. Aptamers have been shown to distinguish between targets based on very small structural differences such as the presence or absence of a methyl or hydroxyl group and certain aptamers can distinguish between D- and L-enantiomers. Aptamers have been obtained that bind small molecular targets, including drugs, metal ions, and organic dyes, peptides, biotin, and proteins, including but not limited to streptavidin, VEGF, viral proteins, and various enzymes, including without limitation DNA-dependent DNA polymerase, RNA-dependent DNA polymerase, RNA-dependent RNA polymerase, helicase, and protease (see, e.g., Lin and Jayasena, J. Mol. Biol. 271:100-11 (1997); Thomas et al., J. Biol. Chem. 272: 27980-86 (1997); Kulbachinskiy et al., Eur. J. Biochem. 271:4921-31 (2004); Hannoush et al., Chembiochem. 5:527-33 (2004); Bellecave et al., Oligonucleotides 13:455-63 (2003); and Nishikawa et al., Nucl. Acids Res. 31:1935-43 (2003)). Aptamers have been shown to retain functional activity after biotinylation, fluorescein labeling, and when attached to glass surfaces and microspheres.

Aptamers, including speigelmers, are identified by an in vitro selection process, for example but not limited to the process known as systematic evolution of ligands by exponential amplification (SELEX). In the SELEX process very large combinatorial libraries of oligonucleotides, for example $10^{14}$ to $10^{15}$ individual sequences, often as large as 60-100 nucleotides long, are routinely screened by an iterative process of in vitro selection and amplification. Most targets are affinity enriched within 8-15 cycles and the process has been automated allowing for faster aptamer isolation. The skilled artisan will understand that aptamers can be obtained following conventional procedures and without undue experimentation. Descriptions of aptamers and their selection can be found in, among other places, L. Gold, J. Biol. Chem., 270(23):13581-84 (1995); L. Gold et al., Ann. Rev. Biochem. 64:763-97 (1995); Wilson and Szostak, Ann. Rev. Biochem. 68:611-47 (1999); Cox et al., Nucl. Acids Res. 30:e108 (2002); Hermann and Patel, Science 287:820-25 (2000); Vuyisich and Beal, Chem. & Biol. 9:907-13 (2002); S. Jayasena, Clin. Chem., 45:1628-50 (1999); Cox and Ellington, Bioorg. Med. Chem. 9:2525-31 (2001); Eulberg et al., Nucl. Acids Res. 33:e5 (2005); and Jayasena and Gold, U.S. Pat. No. 6,183,967.

The term "DNA polymerase" is used in a broad sense herein and refers to any polypeptide that can catalyze the 5'-3'extension of a hybridized primer by the addition of deoxyribonucleotides and/or certain nucleotide analogs in a template-dependent manner. For example but not limited to, the sequential addition of deoxyribonucleotides to the 3'-end of a primer that is annealed to a nucleic acid template during a primer extension reaction. Non-limiting examples of DNA polymerases include RNA-dependent DNA polymerases, including without limitation reverse transcriptases, and DNA-dependent DNA polymerases. It is to be appreciated that certain DNA polymerases (for example but not limited to certain eubacterial Type A DNA polymerases and Taq DNA polymerase) may further comprise a structure-specific nuclease activity and that when an amplification reaction comprises an invasive cleavage reaction, for example but not limited to, FEN-LCR or PCR-FEN (see, e.g., Bi et al., U.S. Pat. No. 6,511,810; and Neville et al., BioTechniques 32:S34-43 (2002)), wherein the cleaving enzyme comprises a DNA polymerase, such polymerase is referred to herein as a cleaving enzyme in the invasive cleavage context and the corresponding enzymatic activity comprises structure-specific oligonucleotide cleavage. In certain embodiments, a DNA polymerase provides both a polymerization activity and a structure-specific cleaving activity. The term "RNA polymerase" refers to a DNA-dependent RNA polymerase or an RNA-dependent polymerase (sometimes referred to as an RNA replicase), and includes any polypeptide that can catalyze the 5'-3' addition of ribonucleotides in a template-dependent manner. In certain embodiments, an RNA polymerase binds to a promoter sequence and catalyzes transcription. Non-limiting examples of RNA polymerases include the RNA polymerases from the bacteriophages T3, T7, SP6, f2, MS2, and Qβ.

The term "primer" refers to a polynucleotide, generally an oligonucleotide comprising a "target" binding portion that is typically about 12 to about 35 nucleotides long, that is designed to selectively hybridize with a target nucleic acid flanking sequence or to a corresponding primer-binding site of an amplification product under appropriate stringency conditions; and serve as the initiation point for the synthesis of a nucleotide sequence that is complementary to the corresponding polynucleotide template from its 3'-end.

The terms "forward" and "reverse" when used in reference to the primers of a primer pair indicate the relative orientation of the primers on a polynucleotide sequence. For illustration purposes but not as a limitation, consider a single-stranded polynucleotide drawn in a horizontal, left to right orientation with its 5'-end on the left. The "reverse" primer is designed to anneal with the downstream primer-binding site at or near the "3'-end" of this illustrative polynucleotide in a 5' to 3' orientation, right to left. The corresponding "forward primer is designed to anneal with the complement of the upstream primer-binding site at or near the "5'-end" of the polynucleotide in a 5' to 3' "forward" orientation, left to right. Thus, the reverse primer comprises a sequence that is complementary to the reverse or downstream primer-binding site of the polynucleotide and the forward primer comprises a sequence that is the same as or substantially the same as the forward or upstream primer-binding site. It is to be understood that the terms "3-end" and "5'-end" as used in this paragraph are illustrative only and do not necessarily refer literally to the respective ends of the polynucleotide. Rather, the only limitation is that the reverse primer of this exemplary primer pair anneals with a reverse primer-binding site that is downstream of the forward primer-binding site that comprises the same sequence or substantially the same sequence as the "target" binding portion of the corresponding forward primer. As will be recognized by those of skill in the art, these terms are not intended to be limiting, but rather to provide illustrative orientation in a given embodiment.

A "primer pair" of the current teachings comprises a forward primer and a corresponding reverse primer. The forward primer comprises a first target-specific portion that comprises a sequence that is the same as or substantially the same as the nucleotide sequence of the first or upstream target flanking sequence, and that is designed to selectively hybridize with the complement of the upstream target flanking sequence that is present in, among other places, the reverse amplification product. The reverse primer of the primer pair comprises a second target-specific portion that comprises a sequence that is complementary to or substantially complementary to, and that is designed to selectively hybridize with, the second or downstream target region flanking sequence that is present in among other places, the forward amplification product. In certain embodiments, a forward primer, a reverse primer, or a forward primer and a reverse primer of a primer pair further comprises a reporter-probe binding site, a universal primer-binding site, and/or a reporter group, for example but not limited to a fluorescent reporter group. In some embodiments, a sequencing primer comprises a fluorescent reporter group. In certain embodiments, a forward primer and the corresponding reverse primer of a primer pair have different melting temperatures to permit temperature-based asymmetric PCR.

A universal primer or primer set may be employed according to certain embodiments of the current teachings. In certain embodiments, a universal primer or a universal primer set hybridizes with and can be used to amplify two or more different target nucleic acid species and/or two or more different species of desired amplicon.

The term "probe" refers to a polynucleotide that comprises a portion that is designed to hybridize in a sequence-specific manner with a complementary probe-binding site on a particular nucleic acid sequence, for example but not limited to a target nucleic acid or an amplification product. In certain embodiments, corresponding probes of a ligation probe set are ligated together to form a ligated probe. In some embodiments, corresponding probes of a cleavage probe set anneal with a template strand to form a nucleic acid cleavage structure, which can be cleaved by an appropriate cleaving enzyme under suitable conditions to form a hybridization structure comprising the template strand, the upstream cleavage probe, and a hybridized fragment of the second cleavage probe. In certain embodiments, the annealed upstream cleavage probe and the hybridized fragment of the downstream cleavage probe are ligated together to form a ligated probe. In certain embodiments, a probe comprises a reporter group, for example but not limited to, a reporter probe. In some embodiments, a probe comprises a primer-binding iste.

The sequence-specific portions of probes and primers of the current teachings are of sufficient length to permit specific annealing to complementary sequences in target nucleic acids and desired amplicons. Detailed descriptions of primer and probe design can be found in, among other places, Dieffenbach and Dveksler, PCR Primer, A Laboratory Manual, Cold Spring Harbor Press (1995; hereinafter "PCR Primer"); R. Rapley, The Nucleic Acid Protocols Handbook (2000), Humana Press, Totowa, N.J. (hereinafter "Rapley"); Schena; and Kwok et al., Nucl. Acid Res. 18:999-1005 (1990). Primer and probe design software programs are also commercially available, including without limitation, Primer Express, Applied Biosystems, Foster City, Calif.; Primer Premier and Beacon Designer software, PREMIER Biosoft International, Palo Alto, Calif.; Primer Designer 4, Sci-Ed Software, Durham, N.C.; Primer Detective, ClonTech, Palo Alto, Calif.; Lasergene, DNASTAR, Inc., Madison, Wis.; Oligo software, National Biosciences, Inc., Plymouth, Minn.; iOligo, Caesar Software, Portsmouth, N.H.; and RTPrimerDB on the world wide web at realtimeprimerdatabase.ht.st or at medgen31.urgent.be/primerdatabase/index (see also, Pattyn et al., Nucl. Acid Res. 31:122-23 (2003)).

The skilled artisan will appreciate that the complement of the disclosed probes and primers, target nucleic acids, desired amplicons, or combinations thereof, may be employed in certain embodiments of the current teachings. For example, without limitation, a genomic DNA sample may comprise both the target nucleic acid sequence and its complement. Thus, in certain embodiments, when a genomic sample is denatured, both the target nucleic acid and its complement are present in the sample as single-stranded sequences. In certain embodiments, a primer, a ligation probe pair, a cleavage probe pair, or combinations thereof may be designed to selectively hybridize to an appropriate sequence, including without limitation, a target nucleic acid, the complement of a target nucleic acid, an amplicon, and/or the complement of an amplicon.

The term "reporter probe" refers to a sequence of nucleotides and/or nucleotide analogs, that anneals with a target nucleic acid and/or an amplicon, and when detected, including but not limited to a change in intensity or of emitted wavelength, is used to identify and/or quantify the corresponding target nucleic acid in an end-point or real-time detection technique, for example but not limited to a Q-PCR technique. Most reporter probes can be categorized based on their mode of action, for example but not limited to: nuclease probes, including without limitation TaqMan® probes (see, e.g., Livak, Genetic Analysis: Biomolecular Engineering 14:143-149 (1999); Yeung et al., BioTechniques 36:266-75 (2004)); extension probes such as scorpion primers, Lux™ primers, Amplifluors, and the like; hybridization probes such as molecular beacons, Eclipse probes, light-up probes, pairs of singly-labeled reporter probes, hybridization probe pairs, and the like; or combinations thereof. In certain embodiments, reporter probes comprise a PNA, an LNA, a universal base, or combinations thereof, and can include stem-loop and stem-less reporter probe configurations. Certain reporter probes are singly-labeled, while other reporter probes are doubly-labeled. Dual probe systems that comprise FRET between adjacently hybridized probes are within the intended scope of the term reporter probe (see, e.g., Zhang et al., Hepatology 36:723-28 (2003)).

An "unsymmetrical cyanine dye", sometimes described in the art as an asymmetric cyanine dye or an asymmetrical cyanine dye, refers to a dye molecule with the general formula $R_2N[CH=CH]_nCH=NR_2$, where n is a small number and the R groups typically comprise at least one benzazole group and at least one quinoline group or at least one pyridine group. Non-limiting examples of unsymmetrical cyanine dyes include [2-[N-(3-dimethylaminopropyl)-N-propylamino]-4-[2,3-dihydro-3-methyl-(benzo-1,3-thiazol-2-yl)-methylidene]-1-phenyl-quinolinium] (SYBR® Green), [2-[N-bis-(3-dimethylaminopropyl)-amino)-amino]-4-[2,3-dihydro-3-methyl-(benzo-1,3-thiazol-2-yl)-methylidene]-1-phenyl-quinolinium] (PicoGreen®), 4-[(3-methyl-6-(benzothiazol-2-yl)-2,3-dihydro-(benzo-1,3-thiazole)-2-methylidene)]-1-methyl-pyridinium iodide (BEBO), BOXTO, and BETO. Descriptions of unsymettrical cyanine dyes can be found in, among other places, Karlsson et al., Nucl. Acids Res. 31:6227-34 (2003); Zipper et al., Nucl. Acids Res. 32:e103 (2004); Bengtsson et al., Nucl. Acids Res. 31:e45 (2003); and Goransson et al., Asymmetric cyanine dyes, DNA-Technology 2005, Chalmers University Technology (2005; available on the world wide web at: molbiotech.Chalmers.se/research/mk/Asymmetric % cyanine % dyes.doc).

The term "target nucleic acid" or "target" refers to the nucleic acid sequence that is specifically amplified and/or detected using the compositions, methods, and kits of the present teachings (in contrast to a secondary amplification product, which is the result of a spurious side-reaction, typically due to mis-priming). In certain embodiments, a target nucleic acid serves as a template in a primer extension reaction. In some embodiments, a target nucleic acid serves as a ligation template. In some embodiments, a target nucleic acid serves as a template strand in a nucleic acid cleavage structure. In certain embodiments, the target nucleic acid comprises DNA and is present in genomic DNA (gDNA) or mitochondrial DNA (mtDNA). In certain embodiments, the target nucleic acid comprises RNA, for example but not limited to, ribosomal RNA (rRNA), messenger RNA (mRNA), transfer RNA (tRNA), or an RNA molecule such as a miRNA precursor, including without limitation, a pri-miRNA, a pre-miRNA, or a pri-miRNA and a pre-miRNA. In some embodiments, the target nucleic acid comprises a small RNA molecule, including without limitation, a miRNA, a sRNA, a stRNA, a snoRNA, or other ncRNA. The target nucleic acid need not constitute the entirety of a nucleic acid molecule. For example but not as a limitation, a large nucleic acid, for example a gDNA fragment, can comprise a multiplicity of different target nucleic acids. Typically, a target nucleic acid has at least one defined end. In many nucleic acid amplification reactions the target has two defined ends.

In certain embodiments, a target nucleic acid is located between two flanking sequences, a first target flanking sequence and a second target flanking sequence, located on either side of, but not necessarily immediately adjacent to, the target nucleic acid. In some embodiments, a polynucleotide such as a gDNA fragment comprises a plurality of different target nucleic acids. In some embodiments, a target nucleic acid is contiguous with or adjacent to one or more different target nucleic acids. In some embodiments, a given target nucleic acid can overlap one target nucleic acid on its 5'-end, another target nucleic acid on its 3'-end, or both. In other embodiments, for example but not limited to when the target comprises a small RNA molecule, the target may not comprise a flanking region and a primer is designed to anneal with a portion of the small RNA target, typically an end of the target nucleic acid (see, e.g., Chen et al., U.S. patent application Ser. No. 10/947,460.

Certain Exemplary Component Techniques

According to the instant teachings, a target nucleic acid may be obtained from any living or once living organism, including a prokaryote, an archaea, or a eukaryote, for example but not limited to: an insect, including without limitation *Drosophila*; a worm, including without limitation *C. elegans*; a plant, including without limitation *Arabidopsis*; and an animal, including without limitation a human, a mouse, a domesticated animal, or a non-human primate; and including prokaryotic cells and cells, tissues, and organs obtained from a eukaryote, for example but not limited to, clinical biopsy material, buccal swabs, cultured cells, and blood cells. Viral nucleic acid is also within the scope of the current teachings. In certain embodiments, the target nucleic acid may be present in a double-stranded or single-stranded form. The skilled artisan appreciates that gDNA includes not only full length material, but also fragments generated by any number of means, for example but not limited to, enzyme digestion, sonication, shear force, and the like, and that all such material, whether full length or fragmented, represent forms of gDNA that can serve as templates for an amplifying reaction of the current teachings.

A target nucleic acid can be either synthetic or naturally occurring. Certain target nucleic acid, including flanking sequences where appropriate, can be synthesized using oligonucleotide synthesis methods that are well-known in the art. Detailed descriptions of such techniques can be found in, among other places, Beaucage; and Blackburn and Gait. Automated DNA synthesizers useful for synthesizing target nucleic acids and other oligonucleotides, including without limitation certain enzyme inhibitors, probes, and primers are commercially available from numerous sources, including for example, the Applied Biosystems DNA Synthesizer Models 381A, 391, 392, and 394 (Applied Biosystems, Foster City, Calif.). Target nucleic acid, including flanking regions where appropriate, and other oligonucleotides can also be generated biosynthetically, using in vivo methodologies and/or in vitro methodologies that are well known in the art. Descriptions of such technologies can be found in, among other places, Sambrook et al., Molecular Cloning, A Laboratory Manual, Cold Spring Harbor Press (1989) (hereinafter "Sambrook et al."); and Ausubel et al., Current Protocols in Molecular Biology, John Wiley & Sons, Inc., including supplements through Sep. 26, 2005 (hereinafter "Ausubel et al.").

Target nucleic acids for use in the methods of the current teachings, including but not limited to, gDNA can be obtained from biological materials using any suitable sample preparation technique known in the art. Commercially available nucleic acid extraction instruments and systems include, among others, the ABI PRISM® 6100 Nucleic Acid PrepStation and the ABI PRISM® 6700 Nucleic Acid Automated Work Station. Nucleic acid sample preparation reagents and kits are also commercially available, including without limitation, NucPrep™ Chemistry, BloodPrep™ Chemistry, the ABI PRISM® TransPrep System, and PrepMan™ Ultra Sample Preparation Reagent (all from Applied Biosystems); and the miRvana RNA Isolation kit (Ambion, Austin, Tex.). Purified or partially purified nucleic acid, including without limitation, gDNA and total RNA and tissue-specific nucleic acid preparations, is commercially available from numerous commercial sources, including but not limited to Coriell Cell Repositories, Coriell Institute for Medical Research, Camden, N.J.; Serologicals Corp., Norcross, Ga.; Stratagene, La Jolla Calif.; Ambion, Austin, Tex.; and the American Type Culture Collection (ATCC), Manassas, Va.

The terms "amplifying" and "amplification" are used in a broad sense and refer to any technique known in the art in which a target nucleic acid, an amplicon, at least part of a target nucleic acid, or at least part of an amplicon, is reproduced or copied (including the synthesis of a complementary strand or the formation of a ligation probe), typically in a template-dependent manner, including a broad range of techniques for amplifying nucleic acid sequences, either linearly or exponentially. Some amplifying techniques are performed isothermally; some amplification techniques are performed using temperature cycling; some amplification techniques comprise at least one isothermal amplifying step and at least one amplifying step comprising thermocycling. Some non-limiting examples of amplification techniques include primer extension, including without limitation PCR, RT-PCR, asynchronous PCR (A-PCR), asymmetric PCR, quantitative or Q-PCR; ligase chain reaction (LCR), ligase detection reaction (LDR), including without limitation gap-filling and gap oligonucleotide versions of each (see, e.g., Cao, Chapter 1.3 in DNA Amplification: Current Techniques and Applications, Demidov and Broude, eds., Horizon Bioscience (2004; hereinafter "Demidov and Braude"); Abravaya et al., Nucl. Acids Res. 23:675-82 (1995); Lizardi et al., Nat. Genetics 19:225-32 (1998); and Segev, U.S. Pat. No. 6,004,826); rolling circle amplification (RCA), sometimes referred to as rolling circle replication (RCR); strand displacement amplification (SDA) and multiple displacement amplification (MDA); nucleic acid strand-based amplification (NASBA), sometimes referred to as transcription-mediated amplification (TMA) or self-sustained replication (3SR); SPIA™ and RiboSPIA™ amplification (see, e.g., Kurn, U.S. Pat. No. 6,251,639 and U.S. Patent Application Publication No. US 2003/0017591A1); and helicase-dependent amplification (HDA; see, e.g., Vincent et al., EMBO Reports 5:795-800 (2004)), and including without limitation multiplex versions and/or combinations thereof, for example but not limited to, OLA/PCR, PCR/LDR, PCR/LCR, also known as combined chain reaction (CCR). Descriptions of certain amplification techniques can be found in, among other places, Molecular Cloning, A Laboratory Manual, Sambrook and Russell, eds., Cold Spring Harbor Press, 3d ed. (2001; hereinafter "Sambrook and Russell"); Sambrook et al.; Ausubel et al.; PCR Primer; McPherson; Rapley; Lizardi et al., Nat. Genetics 19:225-32 (1998); Wiedmann et al., S51-64, in PCR Methods and Applications, Cold Spring Harbor Laboratory Press (1994); Cao, Trends in Biotechnol. 22:38-44 (2004); and Wenz and Schroth, U.S. Patent Application Publication No. US 2003/0190646A1.

In certain embodiments, amplification techniques comprise at least one cycle of amplification, for example, but not limited to, the steps of: denaturing a double-stranded nucleic acid to separate the component strands; hybridizing a primer to a target flanking sequence or a primer-binding site of an amplicon (or complements of either, as appropriate); and synthesizing a strand of nucleotides in a template-dependent manner using a DNA polymerase. In certain embodiments, a cycle of amplification comprises the steps of: denaturing a double-stranded nucleic acid to separate the component strands; hybridizing a first ligation probe and a corresponding second ligation probe to (1) the target nucleic acid or the complement of the target nucleic acid or (2) an amplicon; and ligating the adjacently hybridized probes with a ligase to form a ligated probe (an exemplary amplicon). In certain embodiments, a cycle of amplification comprises the steps of: denaturing a double-stranded nucleic acid to separate the component strands; hybridizing an upstream cleavage probe and a corresponding downstream cleavage probe to (1) the target nucleic acid or the complement of the target nucleic acid or (2) an amplicon, to form a nucleic acid cleavage structure; cleaving the cleavage structure to release the flap and form a hybridization structure comprising the upstream cleavage probe annealed adjacent to the hybridized fragment of the downstream cleavage probe; and optionally ligating the adjacently hybridized probes with a ligase to form a ligated probe. The cycle may or may not be repeated. In certain embodiments, a cycle of amplification comprises a multiplicity of amplification cycles, for example but not limited to 20 cycles, 25 cycles, 30 cycles, 35 cycles, 40 cycles, 45 cycles or more than 45 cycles of amplification.

In some embodiments, amplifying comprises thermocycling using an instrument, for example but not limited to, a GeneAmp® PCR System 9700, 9600, 2700, or 2400 thermocycler (all from Applied Biosystems). In certain embodiments, single-stranded amplicons are generated in an amplification reaction, for example but not limited to asymmetric PCR or A-PCR.

Devices have been developed that can perform a thermal cycling reaction and detection with reaction compositions containing a nucleic acid dye, emit a light beam of a specified wavelength, read the intensity of the fluorescent signal emitted from the nucleic acid dye molecules associated with double-stranded nucleic acids, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.) and the ABI GeneAmp® 5700 Sequence Detection System (Applied Biosystems, Foster City, Calif.).

In certain embodiments, these functions may be performed by separate devices. For example but not as a limitation, if one employs a Q-beta replicase reaction for amplification, the reaction may not take place in a thermal cycler, but in a reaction vessel in an instrument that could include a light beam emitted at a specific wavelength, detection of the fluorescent signal, and calculation and display of the amount of amplification product on a monitor or other read-out device.

In certain embodiments, combined thermal cycling and fluorescence detecting devices can be used for precise quantification of target nucleic acid sequences in samples. In certain embodiments, fluorescent signals can be detected and displayed during and/or after one or more thermal cycles, thus permitting monitoring of amplification products as the reactions occur in "real time." In certain embodiments, one can use the amount of amplification product and number of amplification cycles to calculate how much of the target nucleic acid sequence was in the sample prior to amplification.

In some embodiments, one ligation probe set is provided for a target nucleic acid and the target is amplified linearly, for example but not limited to LDR. In certain embodiments, two ligation probe sets are provided for a target nucleic acid and the target is amplified exponentially, for example but not limited to LCR. In some embodiments, a first cleavage probe and a corresponding second cleavage probe anneal with the target nucleic acid to form a nucleic acid cleavage structure comprising a overlapping or flap sequence that forms a suitable substrate for a cleaving enzyme. In certain embodiments, after cleavage, the first cleavage probe and the hybridized fragment of the second cleavage probe can be ligated to form a ligated probe. In some embodiments, a ligated probe comprises a primer-binding site and can serve as the template for a primer extension reaction, for example but not limited to PCR.

Primer extension according to the present teachings is an amplification process comprising elongating a primer that is annealed to a template in the 5' to 3' direction using a DNA polymerase. According to certain embodiments, with appropriate buffers, salts, pH, temperature, and appropriate NTPs (which may, but need not, comprise a nucleotide analog), a DNA polymerase incorporates nucleotides complementary to the template strand starting at the 3'-end of an annealed primer, to generate a complementary strand. In certain embodiments, the DNA polymerase used for primer extension lacks or substantially lacks 5'-exonuclease activity, 3'-exonuclease activity, or both. In some embodiments, primer extension comprises reverse transcription and the DNA polymerase comprises a reverse transcriptase or a DNA-dependent DNA polymerase that under certain conditions comprises reverse transcriptase activity, for example but not limited to, *Thermus thermophilus* (Tth) DNA polymerase, recombinant Tth DNA polymerase (rTth pol), GeneAmp AccuRT RNA PCR Enzyme, or *Thermus* species Z05 (TZ05) DNA polymerase (see, e.g., Smith et al., in PCR Primer, at pages 211-219). In certain embodiments, primer extension comprises a reverse transcriptase and a DNA-dependent DNA polymerase. In certain such embodiments, the reaction composition may comprise one DNA polymerase inhibitor or at least two different DNA polymerase inhibitors, for example but not limited to a first DNA polymerase that can form a complex with the reverse transcriptase and a second DNA polymerase inhibitor that can form a complex with the DNA-dependent DNA polymerase. Descriptions of certain primer extension reactions can be found in, among other places, Sambrook et al., Sambrook and Russell, Ausubel et al. and Chen et al., U.S. patent application Ser. No. 10/947,460.

In some embodiments of the current teachings, amplification comprises a two-step reaction including without limitation a pre-amplification step wherein a limited number of cycles of amplification occur (for example but not limited to 2, 3, 4, or 5 cycles of amplification), then the resulting amplicon is generally diluted and portions of the diluted amplicon are subjected to additional cycles of amplification in a subsequent amplification step (see, e.g., Marmaro and Gordes, U.S. Pat. No. 6,605,451; and Andersen and Ruff, U.S. Patent Application Publication No. US 2004/0175733). In some embodiments, a pre-amplification step, a subsequent amplification step, or both, comprise a DNA polymerase inhibitor.

In certain embodiments, an amplification reaction comprises multiplex amplification, in which a multiplicity of different target nucleic acids and/or a multiplicity of different amplification product species are simultaneously amplified using a multiplicity of different primer sets, a multiplicity of different ligation probe sets, a multiplicity of different cleavage probe sets, or combinations thereof (see, e.g., Henegariu et al., BioTechniques 23:504-11, 1997; Belgrader et al., Development of a Multiplex Ligation Detection Reaction DNA Typing Assay, Sixth International Symposium on Human Identification (1995); and Rapley, particularly in Chapter 79). Certain embodiments of the disclosed methods comprise a multiplex amplification reaction and a single-plex amplification reaction, including a multiplicity of single-plex or lower-plexy reactions (for example but not limited to a two-plex, a three-plex, a four-plex, a five-plex, or a six-plex reaction) performed in parallel.

In certain embodiments, an amplifying reaction comprises asymmetric PCR. According to certain embodiments, asymmetric PCR comprises a reaction composition comprising (i) at least one primer pair in which there is an excess of one primer, relative to the corresponding primer of the primer pair, for example but not limited to a five-fold, a ten-fold, or a twenty-fold excess; (ii) at least one primer pair that comprises only a forward primer or only a reverse primer; (iii) at least one primer pair that, during given amplification conditions, comprises a primer that results in amplification of one strand and a corresponding primer that is disabled; or (iv) at least one primer pair that meets the description of both (i) and (iii) above. Consequently, when the target nucleic acid and/or amplicon is amplified, an excess of one strand of the subsequent amplification product (relative to its complement) is generated. Descriptions of asymmetric PCR, can be found in, among other places, McPherson, particularly in Chapter 5; and Rapley, particularly in Chapter 64.

In certain embodiments, one may use at least one primer pair wherein the Tm of one of the primers is higher than the Tm of the other primer, sometimes referred to as A-PCR (see, e.g., Chen et al., U.S. Patent Application Publication No. US 2003/0207266A1). In certain embodiments, the Tm of the forward primer is at least 4-15° C. different from the Tm of the corresponding reverse primer. In certain embodiments, the Tm of the forward primer is at least 8-15° C. different from the Tm of the corresponding reverse primer. In certain embodiments, the Tm of the forward primer is at least 10-15° C. different from the Tm of the corresponding reverse primer. In certain embodiments, the Tm of the forward primer is at least 10-12° C. different from the Tm of the corresponding reverse primer. In certain embodiments, in at least one primer pair, the Tm of a forward primer differs from the Tm of the corresponding reverse primer by at least about 4° C., by at least about 8° C., by at least about 10° C., or by at least about 12° C.

In certain embodiments of A-PCR, in addition to the difference in Tm of the primers in a primer pair, there is also an excess of one primer relative to the other primer in the primer pair. In certain embodiments, there is a five- to twenty-fold excess of one primer relative to the other primer in the primer pair. In certain embodiments of A-PCR, the primer concentration is at least 50 nM.

According to certain A-PCR embodiments, one may use conventional PCR in the first cycles of amplification such that both primers anneal and both strands of a double-stranded amplicon or target nucleic acid are amplified. By raising the temperature in subsequent cycles of the same amplification reaction, however, one may disable the primer with the lower Tm such that only one strand is amplified. Thus, the subsequent cycles of A-PCR in which the primer with the lower Tm is disabled result in asymmetric amplification. Consequently, when the target nucleic acid or an amplification product is amplified, an excess of one strand of the subsequent amplification product (relative to its complement) is generated.

According to certain A-PCR embodiments, the level of amplification can be controlled by changing the number of cycles during the first phase of conventional PCR cycling. In such embodiments, by changing the number of initial conventional cycles, one may vary the amount of the double-stranded amplification products that are subjected to the subsequent cycles of PCR at the higher temperature in which the primer with the lower Tm is disabled.

Certain methods of optimizing amplification reactions are known to those skilled in the art. For example, it is known that PCR may be optimized by altering times and temperatures for annealing, polymerization, and denaturing, as well as changing the buffers, salts, and other reagents in the reaction composition. Optimization may also be affected by the design of the probes and/or primers used. For example, the length of the probes and/or primers, as well as the G-C:A-T ratio may alter the efficiency of annealing, thus altering the amplification reaction. Descriptions of amplification optimization can be found in, among other places, James G. Wetmur, "Nucleic Acid Hybrids, Formation and Structure," in Molecular Biology and Biotechnology, pp. 605-8, (Robert A. Meyers ed., 1995); McPherson, particularly in Chapter 4; Rapley; and Protocols & Applications Guide, rev. 9/04, Promega.

Certain reaction compositions further comprise dUTP and uracil-N-glycosylase (UNG; e.g., AmpErase®, Applied Biosystems) or uracil-DNA glycosylase (UDG; New England BioLabs, Beverly, Mass.). Discussion of the use of dUTP and UNG in amplification reactions may be found, for example, in Kwok et al., Nature, 339:237-238, 1989; McPherson; Longo et al., Gene, 93:125-128, 1990; and Gelfand et al., U.S. Pat. No. 5,418,149.

In certain method embodiments, amplification comprises a helicase, including without limitation, *E. coli* UvrD helicase, DnaB helicase, or bacteriophage T7 gene 4 protein; a DNA polymerase, including without limitation DNA polymerase III or the Klenow fragment of DNA polymerase I; a helicase accessory protein, including without limitation, MutL protein; a single-stranded binding protein (SSB), including without limitation, *E. coli* SSB, T7 gene 2.5 SSB, T4 gene 32 protein, and/orRB49 gene 32 protein; or combinations thereof. In certain embodiments, an enzyme inhibitor comprising a nucleotide sequence and a quencher is designed to inhibit the enzymatic activity of a helicase when the enzyme inhibitor and the helicase are associated with each other in a complex at a first temperature, but not at a second temperature, at which the enzyme inhibitor and the helicase have dissociated. In certain embodiments, the nucleotide sequence of a helicase inhibitor comprises an aptamer. In some embodiments, the nucleotide sequence of a helicase inhibitor can form a double-stranded segment at the first temperature, but typically not at the second temperature.

In some embodiments, amplification comprises ligase-mediated amplification techniques, for example but not limited to, LDR, LCR, FEN-LCR, gap oligonucleotide and gap-filling versions of ligation mediated-amplification procedures, padlock versions of ligase-mediated amplification, and ligation approaches coupled with PCR and/or other amplification approaches and including multiplex versions thereof (see, e.g., Demidov and Broude, particularly Chapter 1.3; Lizardi et al., Nat. Genetics 19:225-32 (1998); Bi et al., U.S. Pat. No. 6,511,810; and Wenz and Schroth, U.S. Patent Application Publication No. US 2003/0190646A1). According to certain methods comprising ligase-mediated amplification, a ligase and a ligase inhibitor that comprises a nucleotide sequence and a quencher associate at a first temperate to form a ligase-ligase inhibiter complex. When associated with the ligase inhibitor, the enzymatic activity of the ligase is inhibited, which decreases at least some of the misligation that could occur in the absence of the ligase inhibitor, thus decreasing certain secondary amplicons and reducing background fluorescence. When the reaction composition comprising the ligase-ligase inhibitor complex is heated to a second temperature, the ligase inhibitor dissociates from the ligase and adjacently hybridized probes can be efficiently ligated. In certain embodiments, the 5'-end downstream ligation probe and the 3'-end of the corresponding upstream ligation probe are not immediately adjacent when they hybridize to the target nucleic acid or its complement, and a gap-filling step is employed to extend the 3'-end of the upstream probe into juxtaposition with the 5'-end of the downstream probe. In other embodiments, there is a gap between the 5'-end of the downstream probe and the 3'-end of the upstream probe such that a "gap oligonucleotide" can hybridize in the gap between the opposing ends of the ligation probes. In certain such embodiments, the 5'-end downstream probe can be ligated to the 3'-end of the gap oligonucleotide and the 3'-end of the upstream probe can be ligated to the 5'-end of the gap oligonucleotide.

In certain embodiments, the nucleotide sequence of the ligase inhibitor comprises an aptamer. In some embodiments, the nucleotide sequence of a ligase inhibitor can form a double-stranded segment at the first temperature, but typically not at the second temperature.

According to certain gap-filling LCR or gap-filling LDR amplification techniques, a complex comprising a DNA polymerase and a DNA polymerase inhibitor can form at a first temperature, inhibiting the DNA polymerase activity. In certain embodiments, a ligase and a ligase inhibitor form a complex at a first temperature to inhibit ligation of mis-annealed ligation probes, sometimes referred to as misligation.

Those in the art will appreciate that the disclosed enzyme inhibitors, complexes, methods, and kits can be applied in a variety of different contexts in which an enzyme-mediated amplification reaction is performed that may be subject to mis-annealing of primers and/or probes and the subsequent formation of undesired secondary amplicons. Any enzyme-mediated amplification technique that can benefit from the use of an enzyme inhibitor comprising a quencher to at least decrease background fluorescence is within the intended scope of the current teachings.

An amplified or sequenced target nucleic acid can be detected by any suitable technique known in the art that comprises measuring, quantitating, and/or observing directly or indirectly, a quenchable emission, including without limitation, fluorescence, chemiluminescence, bioluminescence, phosphorescence, and so forth, for example but not limited to, laser-induced fluorescence and electrochemiluminescence. According to some embodiments of the disclosed methods, detecting can comprise any suitable real-time or end-point detection technique. Some non-limiting examples of suitable detection techniques include melting curve analysis, Q-PCR or other real-time technique comprising a nucleic acid dye, and in some embodiments, at least one reporter probe; and electrophoresis techniques, including without limitation gel electrophoresis. Those in the art will appreciate that various quencher moieties are available that collectively cover a broad range of detectable emissions and that by pairing a quencher with an appropriate absorption spectra with an emission source, at least some of the emission from that source can be reduced.

In some embodiments, the methods of the current teachings comprise Q-PCR. The term "quantitative PCR", or "Q-PCR", also known as real-time PCR, refers to a variety of methods used to quantify PCR amplification products, either specifically, non-specifically, or both (see, e.g., Raeymakers, Mol. Biotechnol. 15:115-22 (2000); Joyce, Quantitative RT-PCR, in Methods in Mol Biol., vol. 193, O'Connell, ed., Humana Press; Pierson et al., Nucl. Acids Res. 31(14):e73 (2003)). Such methods typically are categorized as kinetics-based systems, that generally determine or compare the amplification factor, such as determining the threshold cycle ($C_t$), or as co-amplification methods, that generally compare the amount of product generated from simultaneous amplification of target and standard templates. Q-PCR techniques typically comprise reporter probes, a nucleic acid dye, or both. For example but not limited to TaqMan® probes (Applied Biosystems), i-probes, molecular beacons, Eclipse probes, scorpion primers, Lux™ primers, FRET primers, ethidium bromide, and unsymmetrical cyanine dyes, for example but not limited to, SYBR® Green I (Molecular Probes), YO-PRO-1, Hoechst 33258, BOXTO (TATAA Biocenter, Goteborg, Sweden) and PicoGreen® (Molecular Probes).

In some embodiments, the methods of the current teachings are performed before or in conjunction with a sequencing reaction. The term "sequencing" is used in a broad sense herein and refers to any technique known in the art that allows the order of at least some consecutive nucleotides in at least part of a polynucleotide, for example but not limited to a target nucleic acid or an amplicon, to be identified. Some non-limiting examples of sequencing techniques include Sanger's dideoxy terminator method and the chemical cleavage method of Maxam and Gilbert, including variations of those methods; sequencing by hybridization; sequencing by synthesis; and restriction mapping. Some sequencing methods comprise electrophoreses, including capillary electrophoresis and gel electrophoresis; sequencing by hybridization including microarray hybridization; mass spectrometry; and single molecule detection. In some embodiments, sequencing comprises direct sequencing, duplex sequencing, cycle sequencing, single base extension sequencing (SBE), solid-phase sequencing, or combinations thereof. In some embodiments, sequencing comprises detecting the sequencing product using an instrument, for example but not limited to an ABI PRISM® 377 DNA Sequencer, an ABI PRISM® 310, 3100, 3100-Avant, 3730, or 3730xl Genetic Analyzer, an ABI PRISM® 3700 DNA Analyzer (all from Applied Biosystems), or a mass spectrometer. In some embodiments, sequencing comprises incorporating a dNTP, including a dATP, a dCTP, a dGTP, a dTTP, a dUTP, a dITP, or combinations thereof and including dideoxyribonucleotide analogs of dNTPs, into an amplification product.

Those in the art will appreciate that the sequencing method employed is not typically a limitation of the present methods. Rather any sequencing technique that provides the order of at least some consecutive nucleotides of at least part of the corresponding amplicon or target nucleic acid can typically be used with the current methods. In some embodiments, unincorporated primers and/or dNTPs are removed prior to a sequencing step by enzymatic degradation, including without limitation exonuclease 1 and shrimp alkaline phosphatase digestion, for example but not limited to the ExoSAP-IT® reagent (USB Corp., Cleveland, Ohio). In some embodiments, unincorporated primers, dNTPs, and/or ddNTPs are removed by gel or column purification, sedimentation, filtration, beads, magnetic separation, or hybridization-based pull out, as appropriate (see, e.g., ABI PRISM® Duplex™ 384 Well F/R Sequence Capture Kit, Applied Biosystems P/N 4308082). In certain embodiments, a reaction composition comprising an amplification product, or at least part of such a reaction composition, is subjected to a sequencing reaction without an intervening purification step (see, e.g., Baskin et al., U.S. Patent Application Publication No. US 2002/0137047 A1). Descriptions of sequencing techniques can be found in, among other places, McPherson, particularly in Chapter 5; Sambrook and Russell; Ausubel et al.; Siuzdak, The Expanding Role of Mass Spectrometry in Biotechnology, MCC Press, 2003, particularly in Chapter 7; and Rapley, particularly in Part VI.

In some embodiments, the disclosed methods and kits comprise a microfluidics device, "lab on a chip", or micro-total analytical system (pTAS). In some embodiments, sample preparation is performed using a microfluidics device. In some embodiments, an amplification reaction is performed using a microfluidics device. In some embodiments, a sequencing or real-time PCR reaction is performed using a microfluidic device. In some embodiments, the nucleotide sequence of at least a part of an amplification product is obtained using a microfluidics device. Descriptions of exemplary microfluidic devices can be found in, among other places, Published PCT Application Nos. WO/0185341 and WO 04/011666; Kartalov and Quake, Nucl. Acids Res. 32:2873-79, 2004; and Fiorini and Chiu, BioTechniques 38:429-46, 2005.

Certain Exemplary Embodiments

The present teachings provide compositions, methods, and kits for amplifying a target nucleic acid and for decreasing background fluorescence, typically in a reaction composition comprising at least one enzyme and at least one enzyme inhibitor that includes at least one nucleotide sequence and at least one quencher.

The instant enzyme inhibitors comprise a nucleotide sequence and a quencher. The nucleotide sequence of such enzyme inhibitors are designed to decrease the formation of undesired amplification products, particularly due to mispriming events at non-target sequences, mis-annealing of ligation and/or cleavage probes, and primer dimer formation, by inhibiting enzyme activity at a first temperature, but not at a second temperature. The decreased level of secondary amplicon formation reduces at least one component of non-specific fluorescence in the reaction composition. The disclosed enzyme inhibitors are also designed to be self-quenching under appropriate conditions. The quencher moiety of the disclosed inhibitors are designed to absorb at least some of the fluorescent signal generated by the association of nucleic acid dye molecules with double-stranded segment(s) of the enzyme inhibitor at the first temperature range, either when the enzyme inhibitor is free in solution or complexed with an enzyme. Thus, the quencher of the enzyme inhibitor reduces at least some of this second source of background fluorescence, further decreasing the non-specific fluorescence in the reaction composition.

Certain Exemplary Enzyme Inhibitors

According to the current teachings, enzyme inhibitors comprising a nucleotide sequence and a quencher are designed to inhibit at least one enzymatic activity of an enzyme while the enzyme inhibitor is associated with the enzyme in an enzyme inhibitor-enzyme complex. The nucleotide sequence of the enzyme inhibitors are designed so that they can form a structure comprising at least one double-stranded segment and the quencher(s) are selected to be able to absorb at least some of the fluorescence emitted from a nucleic acid dye when associated with the double-stranded segment of the enzyme inhibitor. The enzyme-enzyme inhibitor complexes can form and/or remain associated at a first temperature, for example but not limited to, room temperature (typically about 22° C.-28° C.) and temperatures below, at, or slightly above the desired template extension temperature. When a reaction composition comprising an enzyme-enzyme inhibitor complex is heated to a second temperature, the enzyme is released as the complex dissociates. The disclosed RNA polymerase inhibitors are designed to inhibit the polymerization activity of an RNA polymerase when the inhibitor and the RNA polymerase are associated in a complex. The disclosed ligase inhibitors are designed to inhibit the formation of a phosphodiester between two adjacently hybridized nucleotide strands on a template when the ligase inhibitor and the ligase are associated in a complex, including the ligation of mis-annealed ligation probes. The disclosed helicase inhibitors are designed to inhibit the helicase's ability to catalyze the unwinding of double-stranded nucleic acids when the helicase inhibitor and the helicase are associated in a complex. Certain disclosed cleaving enzyme inhibitors are designed to inhibit the 5'-nuclease activity of the cleaving enzyme when the cleaving enzyme inhibitor and the cleaving enzyme are associated in a complex. In certain embodiments, the nucleotide sequence of a ligase inhibitor, an RNA polymerase inhibitor, a helicase inhibitor, and/or a cleaving enzyme inhibitor comprises an aptamer. The inhibitory ability of the enzyme inhibitors of the current teachings are typically not significantly dependent on the exact sequence of the inhibitor. Rather, the overall structure of the enzyme inhibitor and its melting temperature are the major determinants of whether an enzyme inhibitor will inhibit the intended enzymatic activity of the corresponding enzyme. In certain embodiments, an enzyme inhibitor is designed to assume a conformation at a first temperature that mimics the substrate of the corresponding enzyme, allowing the enzyme to associate with the inhibitor to form a complex in which the enzymatic activity of the enzyme is inhibited. At a second temperature, the conformation of the enzyme inhibitor can change so that it no longer mimics the substrate and the enzyme is released from the complex. Thus, the disclosed inhibitors typically exhibit significantly less, if any, inhibitory effect when they are substantially single-stranded and/or not in a complex with the enzyme. In some embodiments, the nucleotide sequence of an enzyme inhibitor comprises a deoxyribonucleotide, a ribonucleotide, a nucleotide analog, a non-nucleotide linker, or combinations thereof.

The disclosed ligase inhibitors do not significantly interfere with the annealing of ligation probes or cleavage probes to corresponding sequences on a target nucleic acid or a desired amplicon, for example but not limited to a ligated probe. The disclosed helicase inhibitors do not significantly interfere with the hybridization of primers to corresponding target flanking sequences or amplicons. The disclosed cleaving enzyme inhibitors do not significantly interfere with the annealing or cleavage probes or ligation probes to corresponding sequences on a target nucleic acid or desired amplicon or the hybridization of primers with corresponding target flanking sequences and/or amplicons.

The disclosed DNA polymerase inhibitors are designed to inhibit the polymerization activity of a DNA polymerase when the inhibitor is associated with the DNA polymerase, and optionally a NTP and/or a nucleotide analog, in a DNA polymerase inhibitor-DNA polymerase complex at a first temperature, for example but not limited to, temperatures approximately the same as or below the Tm of the primer. The inhibitory ability of the DNA polymerase inhibitor of the current teachings is generally not significantly dependent on the exact sequence of the inhibitor. Rather, the overall structure of the DNA polymerase inhibitor and its melting temperature are the major determinants of whether a DNA polymerase inhibitor will inhibit the enzymatic activity of the DNA polymerase, i.e., polymerization. Typically, the disclosed DNA polymerase inhibitors will interfere with the polymerization activity of the DNA polymerase when they comprise a double-stranded segment and are associated with the DNA polymerase, and optionally a NTP and/or a nucleotide analog, in a complex. The disclosed DNA polymerase inhibitors, however, exhibit substantially less, if any, inhibitory effect when they are single-stranded and not in a complex with the DNA polymerase. In certain embodiments, the Tm of the DNA polymerase inhibitors is selected to be approximately the same as or lower than the temperature used for primer extension of the annealed primers employed in the selected polymerization or primer extension reaction, but not always. In some embodiments, the melting temperatures of the DNA polymerase inhibitors are somewhat above the primer extension temperature, for example but not limited to reaction compositions wherein the DNA polymerase inhibitors are used at low concentrations.

Typically, a DNA polymerase inhibitor of the current teachings comprises at least one double-stranded segment at or below the first temperature, but is single-stranded or substantially single-stranded at or above the second temperature. Thus at a first temperature, the enzymatic activity of the DNA polymerase in a complex is inhibited, while at the second temperature, the DNA polymerase is active and amplification reactions can occur.

Exemplary first temperatures include 22° C., 23° C., 24° C., 25° C., 26° C., 27° C., 28° C., 29° C., 30° C., about 22° C. to about 40° C., about 25° C. to about 35° C., and about 22° C. to about 28° C., and expressly including all intervening temperatures in the specified first temperature ranges. Exemplary second temperatures include: 42° C., 43° C., 44° C., 45° C., 46° C., 47° C., 48° C., 49° C., 50° C., 51°

C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., about 48° C. to about 73° C., about 53° C. to about 67° C., about 63° C. to about 67° C., and about 64° C. to about 66° C., and expressly including all intervening temperatures in the specified second temperature ranges. Those in the art will understand that the appropriate first and second temperatures for a given amplification reaction will depend, at least in part, on the enzyme, the Tm of the enzyme inhibitor, and/or the Tm of the primer(s) and/or probes, but that appropriate temperatures can be routinely determined, without undue experimentation, using methods known in the art and informed by the current teachings.

In certain embodiments, the nucleotide sequence of a DNA polymerase inhibitor of the present teachings comprises a single oligonucleotide. In some embodiments, such DNA polymerase inhibitors comprise a first region, a second region, a third region, and optionally, a fourth region; and the first region is complementary to the third region. Under appropriate conditions, including at a first temperature, the first region and the third region of such DNA polymerase inhibitors can anneal and form at least one double-stranded segment so that the DNA polymerase inhibitor assumes a stem-loop or hairpin conformation. In certain embodiments, only a subset of nucleotides in the first region are complementary with the corresponding subset of nucleotides in the third region. In some embodiments, the disclosed DNA polymerase inhibitors comprise a nucleotide analog that may or may not affect the Tm of the DNA polymerase inhibitor.

Some exemplary DNA polymerase inhibitors comprising one oligonucleotide are depicted schematically in FIG. 1. The illustrative DNA polymerase inhibitor shown in FIG. 1A comprises a first region (1) shown with black stripes throughout FIG. 1, a second region (2) shown with a wavy line throughout FIG. 1, a third region (3), and an optional fourth region ([4], shown in brackets to indicate that it is optional in this embodiment) shown shaded in black throughout FIG. 1. The 3'-end of this exemplary inhibitor is non-extendable due to the terminal nucleotide comprising a dideoxycytosine (shown as ddC). The first region (1) further comprises a quencher (5). The exemplary inhibitor is shown with the first region (1) annealed to the third region (3) to form a double-stranded segment, so that the inhibitor is in a stem-loop conformation with the second region (2) forming the loop and the fourth region (4) as a 5' single-stranded overhang. In certain embodiments, the single-stranded overhang of the fourth region of such a DNA polymerase inhibitor comprises at least some ribonucleotides, particularly when the inhibitor is designed to complex with certain reverse transcriptases. The exemplary DNA polymerase inhibitor depicted in FIG. 1B comprises a first region (1), a second region (2), and a third region (3), but not a fourth region. The first region (1) and third region (3) are shown annealed to form a stem and the second region (2) forming a loop structure and further comprising a quencher (5). The illustrative DNA polymerase inhibitor shown in FIG. 1C comprises a first region (1) comprising a first quencher (6), shown as Q1, a second region (2) comprising a second quencher (7), shown as Q2, a third region (3), and an optional fourth region ([4]). The exemplary DNA polymerase inhibitor shown in FIG. 1D comprises a first region (1), a second region (2), a third region (3), and an optional fourth region ([4]) that comprises a quencher (5) at the 5'-end, shown as Q.

In certain DNA polymerase inhibitor embodiments, the nucleotide sequence comprises a first region, a second region, a third region, a fourth region, a fifth region, and a sixth region; wherein the first region is complementary with the third region and the first region and the third region can form at least one double-stranded segment at a first temperature; wherein the fourth region is complementary with the sixth region and the fourth region and the sixth region can form at least one double-stranded segment at a first temperature; wherein there is at least one single-stranded region between the 3'-end of the sixth region and the 5'-end of the first region; and wherein the 3'-end of the sixth region comprises a non-extendible nucleotide.

In other DNA polymerase inhibitor embodiments, the nucleotide sequence comprises at least two different oligonucleotides, for example but not limited to, a first oligonucleotide and a second oligonucleotide. In certain embodiments wherein the DNA polymerase inhibitor comprises two oligonucleotides, the first oligonucleotide comprises a first region and the second oligonucleotide comprises a third region and optionally, a fourth region, and the first region of the first oligonucleotide is complementary to the third region of the second oligonucleotide. In certain embodiments, only a subset of nucleotides in the first region is complementary with the corresponding segment(s) of the third region. Under appropriate conditions, including at a first temperature, the first region of the first oligonucleotide and the third region of the second oligonucleotide can anneal to form a duplex comprising at least one double-stranded segment. When the DNA polymerase inhibitors of the current teachings are heated to a second temperature, for example but not limited to in a second temperature range, they assume a single-stranded or substantially single-stranded conformation, not a stem-loop or a duplex conformation.

Some illustrative enzyme inhibitors comprising two or more oligonucleotides are depicted schematically in FIG. 2. The exemplary DNA polymerase inhibitor shown in FIG. 2A comprises a first oligonucleotide comprising first region (1) shown with black stripes throughout FIG. 2, annealed to a second oligonucleotide that comprises a third region (3) and a fourth region (4) shown shaded in black throughout FIG. 2. The first oligonucleotide of this exemplary DNA polymerase inhibitor further comprises a quencher, shown as Q. The exemplary DNA polymerase inhibitor depicted in FIG. 2B comprises a first oligonucleotide comprising a first region (1), annealed to a second oligonucleotide comprising a third region (3) and a fourth region (4). In this illustrative DNA polymerase inhibitor, the quencher (Q) is shown attached to the fourth region (4). The illustrative DNA polymerase inhibitor shown in FIG. 2C comprises a first oligonucleotide comprising a first region (1) comprising a first quencher (shown as Q1) and a second oligonucleotide comprising a third region (3), and a fourth region (4) comprising a second quencher (shown as Q2). The exemplary DNA polymerase inhibitor shown in FIG. 2D comprises a first oligonucleotide comprising a first region (1) annealed to a second oligonucleotide comprising a third region (3), wherein the second oligonucleotide comprises a quencher (shown as Q). The illustrative DNA polymerase inhibitor shown in FIG. 2E comprises a first oligonucleotide comprising a first region (1) and annealed to a second oligonucleotide comprising a third region (3), wherein both the first oligonucleotide and the second oligonucleotide comprise a quencher (shown as Q1 and Q2).

In certain embodiments, the nucleotide sequence of the DNA polymerase inhibitor comprises an aptamer that binds to and inhibits the enzymatic activity of the DNA polymerase when bound by the aptamer. In some embodiments, a DNA polymerase inhibitor comprises an aptamer that comprises at least one double-stranded segment. When the aptamer is free in solution or is bound to the DNA polymerase in a complex, the quencher absorbs at least some of the fluorescent signal generated by nucleic acid dye molecules associated with the aptamer.

The disclosed DNA polymerase inhibitors do not significantly interfere with primer hybridization with corresponding target flanking sequences and/or amplicons. In addition to decreasing the fluorescent intensity of the nucleic acid dye molecules associated with the double-stranded segment of DNA polymerase inhibitors and decreasing formation of secondary amplicons, some DNA polymerase inhibitors of the current teachings increase the yield of desired amplicons relative to parallel amplification reactions not comprising the DNA polymerase inhibitors.

In some embodiments, the 3'-end of a nucleotide sequence of a DNA polymerase inhibitor is not extendible by a DNA polymerase, typically due to the presence of a non-extendible nucleotide, including without limitation a terminal nucleotide comprising a blocking group. A blocking group is a chemical moiety that can be added to a nucleotide or a nucleic acid to prevent or minimize nucleotide addition by a DNA polymerase. By adding a blocking group to the terminal 3'-OH, the nucleotide is no longer able to participate in phosphodiester bond formation catalyzed by the DNA polymerase. Some non-limiting examples of blocking groups include an alkyl group, non-nucleotide linkers, phosphorothioate, alkane-diol residues, PNA, LNA, nucleotide analogs comprising 3' amino groups in place of the 3'-hydroxyl group, nucleotide analogs comprising 5' hydroxyl groups in place of the 5' phosphate group, and nucleotide derivatives lacking a 3' OH group. An alkyl blocking group is a saturated hydrocarbon that can be straight chained, branched, cyclic, or combinations thereof. Some non-limiting examples of non-extendable nucleotides include nucleotides that have a 3'-hydroxyl group that has been modified such as by substitution with hydrogen or fluorine or by formation of an ester, amide, sulfate or glycoside. These nucleotides are generally not chain extendable. Other examples of non-extendable nucleotides that can be used include nucleotides that have modified ribose moieties. In certain embodiments, ribonucleotides may serve as non-extendable nucleotides because oligonucleotides terminating in ribonucleotides cannot be extended by certain DNA polymerases. The ribose can be modified to include 3'-deoxy derivatives including those in which the 3'-hydroxy is replaced by a functional group other than hydrogen, for example, as an azide group. In certain embodiments, a non-extendible nucleotide comprises a dideoxynucleotide (ddN), for example but not limited to, a dideoxyadenosine (ddA), a dideoxycytosine (ddC), a dideoxyguanosine (ddG), a dideoxythymidine (ddT), or a dideoxyuridine (ddU).

In some embodiments, an enzyme inhibitor comprises two quenchers, three quenchers, or more than three quenchers. In certain inhibitor embodiments, a first region comprises a quencher and/or a third region comprises a third quencher. In certain embodiments, a second region comprises a quencher. In some embodiments, a fourth region comprises a quencher. In certain embodiments, a fifth region comprises a quencher. In certain embodiments, a sixth region comprises a quencher. In some embodiments, an enzyme inhibitor comprises a quencher at the 3'-end of the nucleotide sequence, the 5'-end of the nucleotide sequence, and/or internally. In some embodiments, an enzyme inhibitor comprises a second region and in some embodiments a fifth region that forms the loop of a stem-loop conformation. In certain embodiments, a loop comprises a quencher.

The disclosed ligase inhibitors do not significantly interfere with ligation probe annealing, and in certain embodiments, cleavage probe annealing and/or primer annealing, with corresponding target nucleic acids and/or amplicons. The disclosed cleaving enzyme inhibitors do not significantly interfere with cleavage probe annealing, and in certain embodiments, ligation probe annealing and/or primer annealing, with corresponding target nucleic acids or amplicons. The disclosed helicase inhibitors do not significantly interfere with primer annealing, and in certain embodiments, cleavage probe and/or ligation probe annealing, with corresponding target nucleic acids and/or amplicons. In addition to decreasing the fluorescent intensity of the nucleic acid dye molecules associated with the double-stranded segment of enzyme inhibitors and decreasing formation of secondary amplicons, some enzyme inhibitors of the current teachings may increase the yield of desired amplicons relative to parallel amplification reactions not comprising the enzyme inhibitors.

In certain embodiments, a double-stranded segment of an enzyme inhibitor comprises an internal base pair mismatch. In certain embodiments, an enzyme inhibitor comprises a loop structure, typically stem-loop structures comprising a double-stranded segment and a single-stranded loop. In certain embodiments, an enzyme inhibitor comprises two loop structures. In some embodiments, a second region and/or a fifth region of an enzyme inhibitor can form a loop structure at a first temperature when complementary sequences of the inhibitor anneal with each other, for example but not limited to the first region annealing with the third region; and/or the fourth region annealing with the sixth region. In certain embodiments, the second region, a fifth region, or a second region and a fifth region of the nucleotide sequence comprises 2-12 nucleotides and/or nucleotide analogs, and in some embodiments, 2-6 nucleotides and/or nucleotide analogs. In some embodiments, the second and/or fifth region comprises a non-nucleotide linker. In certain embodiments, the second region, the fifth region, or the second and the fifth region of an enzyme inhibitor consists of, consists essentially of, or comprises the sequence $(T)_n$, wherein n is any number of T nucleotides between 1 and 8, for example but not limited to, TT, TTT, TTTT, or TTTTT. In other embodiments, the second region and/or the fifth region, consists of, consists essentially of, or comprises the nucleotides A, C, and/or G, including without limitation nucleotide analogs of any of these. In some embodiments, the second region and/or the fifth region comprises (1) at least one nucleotide analog, for example but not limited to a PNA and/or an LNA and/or (2) a non-nucleotide linker, for example but not limited to a non-nucleotide comprising a hydrocarbon group (—$CH_2$—), including without limitation, linkers comprising an alkane, alkene, or alkyne portion, and ethylene glycol, including without limitation polyethylene glycol (PEG). Typically the linker group is not hydrophobic. In certain embodiments, a linker is hydrophilic or at least portions of the linker have hydrophilic properties. Those in the art will appreciate that the composition of a linker in the disclosed enzyme inhibitors is generally not a limitation, provided that the linker does not interfere with the enzyme-enzyme inhibitor interaction and that the linker is sufficiently flexible to allow the enzyme inhibitor to self anneal at the first temperature.

In some embodiments, a DNA polymerase inhibitor comprises a minor groove binder on the 3'-end, the 5'-end, or both the 3'-end and the 5-end of the nucleotide sequence. In some embodiments, the minor groove binder is located internally. In certain embodiments, the minor groove binder further comprises a quencher, for example but not limited to, a MGB-NFQ (Applied Biosystems). Non-limiting examples of minor groove binders include, antibiotics such as netropsin, distamycin, berenil, pentamidine and other aromatic diamidines, Hoechst 33258, SN 6999, aureolic anti-tumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogs. Descriptions of minor groove binders can be found in, among other places, Nucleic Acids in Chemistry and Biology, 2d ed., Blackburn and Gait, particularly in section 8.3; Kumar et al., Nucl. Acids Res. 26:831-38, 1998; Kutyavin et al., Nucl. Acids Res. 28:655-61, 2000; Turner and Denny, Curr. Drug Targets 1:1-14, 2000; Kutyavin et al., Nucl. Acids Res. 25:3718-25, 1997; Lukhtanov et al., Bioconjug. Chem. 7:564-7, 1996; Lukhtanov et al., Bioconjug. Chem. 6: 418-26, 1995; U.S. Pat. No. 6,426,408; and PCT Published Application No. WO 03/078450. Those in the art understand that minor groove binders typically increase the $T_m$ of the oligonucleotide to which they are attached, allowing such oligonucleotides to effectively hybridize at higher temperatures. Minor groove binders are commercially available from, among other sources, Applied Biosystems (Foster City, Calif.) and Epoch Biosciences (Bothell, Wash.).

In some embodiments, the nucleotide sequence of an enzyme inhibitor comprises a universal base. In some embodiments, a DNA polymerase inhibitor includes a fourth region or a sixth region that comprises a universal base. In certain embodiments, the nucleotide of the fourth region that is immediately adjacent to the third region of the DNA polymerase inhibitor comprises a universal base. In certain embodiments, the nucleotide of the sixth region that is immediately adjacent to the single-stranded region between the sixth region and the first region of the DNA polymerase inhibitor comprises a universal base. In some embodiments, the universal base interacts with a NTP in a DNA polymerase inhibitor-DNA polymerase complex.

Those in the art will appreciate that the Tm of an enzyme inhibitor can be determined empirically, using well-known methods and instructed by the current teachings, and without undue experimentation; or the Tm can be estimated using algorithms. Several formulas and computer algorithms for calculating an estimated Tm, including chimeric oligomers comprising conventional nucleotides and/or nucleotide analogs, are well-known in the art. According to one such predictive formula for oligonucleotides, Tm=(4× number of G+C)+(2× number of A+T). The Tm for a particular oligonucleotide, such as an enzyme inhibitor, a probe, or a primer, can also be routinely determined using known methods, without undue experimentation. Descriptions of Tm/melting temperatures and their calculation can be found in, among other places, Rapley; Nielsen, Exiqon Technical Note LNA Feb. 7, 2002, Exiqon A/S; McPherson; Finn et al., Nucl. Acids Res. 17:3357-63, 1996.

The melting temperature of the enzyme inhibitors of the current teachings can be modulated in a variety of ways. For example, those in the art understand that the length and/or composition of the complementary sequences of the first and third regions, and in certain embodiments, the fourth and sixth regions, can be varied to increase or decrease the melting temperature of an enzyme inhibitor; in certain inhibitor embodiments, the length and/or composition of the complementary sequences of the fourth and sixth regions can be varied to increase or decrease the Tm of the enzyme inhibitor. Hence, in general, a double-stranded segment with greater numbers of hybridizing base pairs will usually melt at higher temperatures than a double-stranded segment with lesser numbers of hybridizing base pairs. However, if a long double-stranded segment is desired, one of skill in the art can introduce base pair mismatches, for example but not limited to, G:T base pairs, to modulate the melting temperature. In certain embodiments, a double-stranded segment of an enzyme inhibitor comprises one mismatched base pair, two mismatched base pairs, three mismatched base pairs, four mismatched base pairs, or more than four mismatched base pairs, wherein two or more mismatched base pairs can, but need not be, contiguous.

Therefore, the double-stranded segment of the disclosed enzyme inhibitors need not be 100% complementary. Instead, a double-stranded segment can have a number, or a certain percentage, of mismatches or wobble base pairs. For example, the double-stranded segment can have about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% base pair mismatches. In certain embodiments, the melting temperature of an enzyme inhibitor is modulated by designing a a double-stranded segment that comprises an abasic nucleotide analog, for example but not limited to an analog comprising a sugar or a sugar analog and a phosphate or a phosphate analog, but not a nucleotide base or a nucleotide base analog, which among other things, eliminates a base pair in the double-stranded region.

The melting temperature of an enzyme inhibitor comprising a second region and/or a fifth region can also be modulated by increasing or decreasing the number of nucleotides and/or nucleotide analogs in the loop. The melting temperature of an enzyme inhibitor comprising a single oligonucleotide can also be modulated by the presence or absence of one or more "GC clamp" at the junction between a region that can comprise at least one double-stranded segment at a first temperature and a region that does not comprise a double-stranded segment at the first temperature. For example but not limited to the base of a loop structure, including without limitation, in certain embodiments, the nucleotide(s) of the first region that are adjacent to the second region and that anneal with the nucleotide(s) of the third region that are adjacent to the second region (see, e.g., FIG. 1A), and/or in some embodiments, the nucleotide(s) of the fourth region that are adjacent to the fifth region and that anneal with the nucleotide(s) of the sixth region that are adjacent to the fifth region (see, e.g., FIG. 1 E). Likewise, the Tm of enzyme inhibitors comprising two or more oligonucleotides can be modulated by the presence or absence of GC clamps, particularly when they are located at one or both ends of complementary segments of the first and third regions of the enzyme inhibitors, including without limitation, the base of a loop, if appropriate; and in certain embodiments, at one of both ends of complementary segments of the fourth and sixth regions of the enzyme inhibitors. The melting temperature of an enzyme inhibitor can also be modulated by nucleotide analogs in the first and/or third regions of the nucleotide sequence, and in certain embodiments, the fourth and/or sixth regions of the nucleotide sequence, for example but not limited to deaza-dA. Some non-limiting examples of nucleotide analogs that increase the Tm include C-5 propynyl-dC or 5-methyl-2'-deoxycytidine substituted for dC; 2,6-diaminopurine 2'-deoxyriboside (2-amino-dA) substituted for dA; and C-5 propynyl-dU for dT; which increase the relative melting temperature approximately 2.8° C., 1.3° C., 3.0° C., and 1.7° C. per substitution, respectively.

When considering the length of the double-stranded segment(s), the melting temperature of the enzyme inhibitor should be considered. For example but not as a limitation, if the $T_m$ of a DNA polymerase inhibitor is too high, it may denature at a temperature above the temperature used in the amplification for primer extension, thereby causing inhibition of the desired polymerization reaction and a decreased yield of the desired amplicon. If the $T_m$ is too low, the DNA polymerase inhibitor may melt and become inactive at temperatures that permit the primers to hybridize to non-target nucleic acids and be extended. When the DNA polymerase is able to amplify such non-target nucleic acids, many undesirable products will be present in the final amplified product mixture, including primer-dimers. In certain embodiments, an enzyme inhibitor has a melting temperature that is close to, but not significantly greater than, the selected extension. ligation, and/or cleavage reaction temperature of the amplification reaction, as appropriate. In some embodiments, particularly when the enzyme inhibitors are used at low concentrations, enzyme inhibitors with melting temperatures above the primer extension temperature, the ligation temperature, or the cleavage reaction temperature, as appropriate, can be used. Typically, one of skill in the art can determine the melting temperature of an enzyme inhibitor under the conditions in which it will be used, for example, under nucleic acid polymerization conditions.

An exemplary DNA polymerase inhibitor comprises, consists of, or consists essentially of:
5'-[TCTGG] GATA(deazadA)TT(deazadA)TGGTA(deazadA) ATATGT(DABCYL-T)TT C(deazadA)TATTTATT (deazadA)TA(deazadA)TTA TC(MGB-NFQ)-3' (SEQ ID NO:3), wherein the fourth region is shown in brackets, the third region is shown underlined, the second region is shown in bold, and the first region is shown in italics, and wherein the second region comprises a first quencher (shown as DABCYL in this example) and the first region comprises a minor groove binder comprising a second quencher (shown as MGB-NFQ in this example). The first region is substantially complementary to the third region due to the two internal G:T base pair mismatches between the two regions but the DNA polymerase inhibitor is still self-annealing at a first temperature. In some embodiments of this illustrative DNA polymerase inhibitor, the terminal C nucleotide on the 3'-end of the DNA polymerase inhibitor comprises the nucleotide analog dideoxycytosine (ddC). In some embodiments, the second region comprises, consists of, or consists essentially of TT, TTT, or TTTTT. In other embodiments, the second region comprises a non-nucleotide linker. In some embodiments, the second region does not comprise a quencher. In certain embodiments, the 5'-end of the DNA polymerase inhibitor further comprises a quencher. In certain embodiments, at least one of the G nucleotides of the DNA polymerase inhibitor comprises the nucleotide analog deaza-dG. In some embodiments, the first quencher comprises: a TAMRA™ (carboxytetramethylrhodamine); a Black Hole Quencher dye, for example but not limited to BHQ-1, BHQ-2, or BHQ-3 (Biosearch Technologies, Inc.); an OREGON GREEN® dye (Molecular Probes); a ROX™ (carboxy-X-rhodamine); a DABSYL (4-dimethylamino-azobenzene-4'-sulfonyl chloride); or a TET (tetrachlorofluorescein), instead of or in addition to the DABCYL moiety. In some embodiments, the second quencher comprises a DABSYL, a DABCYL, a TAMRA, a Black Hole Quencher, a ROX, an OREGON GREEN, or a TET, instead of or in addition to the MGB-NFQ. The choice of quencher(s) is typically not a limitation of the current teachings provided that the selected quencher(s) can absorb fluorescence at the wavelength that is characteristic of the nucleic acid dye and that the quencher and/or the location of the quencher in the inhibitor does not substantially decrease the ability of the inhibitor to self-anneal and/or complex with the enzyme.

Another exemplary DNA polymerase inhibitor comprises, consists of, or consists essentially of:
5'-(TET)-[TTCTGG] GATAATTATGGTAAATATATTTATATATTTATTA TAATTATddC-3' (SEQ ID NO: 2), wherein the fourth region is shown in brackets, the third region is shown underlined, the second region is shown in bold, and the first region is shown in italics, and wherein the fourth region comprises a quencher (shown as TET in this example). The first region is complementary to the third region. The terminal C nucleotide on the 3'-end of the first region of the DNA polymerase inhibitor comprises the nucleotide analog dideoxycytosine (ddC), rendering this illustrative DNA polymerase inhibitor non-extendible. In some embodiments, the second region comprises, consists of, or consists essentially of TT, TTTT, or TTTTT. In some embodiments, the second region comprises a non-nucleotide linker. In certain embodiments, the second region does not comprise a quencher. In certain embodiments, the 5'-end of the DNA polymerase inhibitor further comprises a quencher. In certain embodiments, at least one of the G nucleotides comprises the nucleotide analog deaza-dG, at least one A nucleotide comprises the nucleotide analog deaza-dA, or at least one of the G nucleotides comprises a deaza-dG and at least one A nucleotide a deaza-dA. In some embodiments, the quencher comprises a TAMRA, a Black Hole Quencher dye, a ROX, an OREGON GREEN, a DABCYL, or a DABSYL instead of or in addition to the TET moiety.

Those in the art will appreciate that typically the length and nucleotide and/or nucleotide analog composition of the disclosed enzyme inhibitors can be varied to optimize the stability of the inhibitor, particularly the double-stranded segment(s) and to increase its ability to inhibit the enzymatic activity of the corresponding enzyme when associated in a complex. Those in the art will also appreciate that the disclosed enzyme inhibitors are typically more effective in inhibiting the formation of secondary amplification products when the dissociation rate, sometimes referred to as the "off-rate", of the enzyme-enzyme inhibitor complex at the first temperature is slow. However, in certain applications, one may be able to compensate for "faster" off-rates by using higher concentrations of the enzyme inhibitor. Those in the art will understand that an appropriate concentration of enzyme inhibitor for a particular application can be determined empirically.

The enzyme inhibitors of the current teachings are particularly useful when detecting comprises a melting curve analysis, sometimes referred to as dissociation curve analysis. To generate a melting or dissociation curve, the reaction composition is heated, typically in a step-wise or incremental fashion, and the fluorescence of the reaction mixture is detected at appropriate intervals. Initially, the non-specific fluorescence in the reaction composition is reduced during the initial heating process due to the quencher moiety in the enzyme inhibitor, which reduces the fluorescence emitted from the nucleic acid dye molecules associated with the double-stranded segment(s) of the enzyme inhibitor in the first temperature range. As the temperature increases to the second temperature, the double-stranded segment(s) of the enzyme inhibitor begin to melt, releasing the nucleic acid dye molecules that had been associated with the double-stranded segments of the enzyme inhibitor. A peak in the dissociation curve (plotted as the first derivative of the fluorescence versus temperature) would be expected to appear due to the enzyme inhibitor dissociating which could complicate the evaluation of one or more amplicons. Due to the presence of the quencher in the enzyme inhibitor, the dissociation peak associated with the melting of the inhibitor is decreased or not detected because the quencher absorbs at least some of the fluorescence emitted from the associated dye molecules, which at least diminishes the dissociation peak of the enzyme inhibitor (see, e.g., FIGS. 3-6).

In general, the DNA polymerase inhibitors of the present teachings may be used in any amplification method in which a DNA polymerase is employed. For example, the disclosed DNA polymerase inhibitors can be used in one or more of the following methods: DNA sequencing, DNA amplification, RNA amplification, reverse transcription, DNA synthesis and/or primer extension. The disclosed DNA polymerase inhibitors can be used in reaction compositions for amplifying target nucleic acids by primer extension, for example but not limited to, PCR and/or reverse transcription. The DNA polymerase inhibitors of the current teachings can also be used in certain sequencing techniques. The disclosed DNA polymerase inhibitors can be used in tests for single nucleotide polymorphisms (SNPs) by single nucleotide primer extension using terminator nucleotides. Any such procedures including variations thereof, for example but not limited to, polynucleotide or primer labeling, minisequencing and the like are contemplated for use with the DNA polymerase inhibitors disclosed herein.

In some embodiments, a ligase inhibitor comprises an oligonucleotide that can serve, at a first temperature, as a ligation substrate mimic, that is a substrate comprising a nick that can not be ligated by the ligase. In some embodiments, a ligase inhibitor comprises two adjacently hybridized nucleic acid ends, but at least one terminal nucleotide of at least one of the ends is not hybridized to the "template" strand of the inhibitor and the two ends can not be ligated together. In certain embodiments, a ligase inhibitor comprises two adjacently hybridized nucleic acid ends, but at least one end comprises a terminal nucleotide that is not ligatable by the ligase. For example, the 3' terminal nucleotide does not comprise a 3'-hydroxyl group, the 5' terminal nucleotide does not comprise a 5'-phosphate group. or both. An illustrative ligase inhibitor embodiment comprising a nick that can not be closed by a ligase is shown in FIG. 1 E. This exemplary ligase inhibitor comprises a first region (1), a second region (2), a third region (3), a fourth region (4), a fifth region (8), and a sixth region (9). The second region (2), shown as a loop structure, further comprises a first quencher (6); and the fifth region (8), also shown as a loop structure, further comprises a second quencher (7). The first region (1) is shown annealed with the third region (3) to form a first double-stranded segment; and the fourth region (4) is shown annealed with the sixth region (9) to form a second double-stranded segment, for example, as can occur at the first temperature. The 3'-end of the sixth region (9) comprises a non-ligatable end (10), for example but not limited to, a terminal nucleotide that lacks a 3'—OH group (shown as X). In certain embodiments, either the 3'-end of the sixth region and/or the 5'-end of the first region of such an illustrative ligase inhibitor is not annealed with the "template strand" (in this illustration, the fourth region (4) and/or the third region (3), respectively. In certain embodiments, the upstream end of a ligase inhibitor (shown as 9 in the illustrative ligase inhibitor depicted in FIG. 1E) comprises 8 nucleotides, 9 nucleotides, 10 nucleotides, 11 nucleotides, 12 nucleotides, 13 nucleotides, 14 nucleotides, 15 nucleotides, 16 nucleotides, 17 nucleotides, 18 nucleotides, 19 nucleotides, 20 nucleotides, or more than 20 nucleotides. It is to be appreciated that the length of the "upstream strand" of a ligase inhibitor will typically be designed to be at least as long as the footprint of the desired ligase and may be longer, In certain embodiments, a ligase inhibitor comprises two oligonucleotides that can adjacently hybridize with a template strand, but the opposed ends at the nick are not suitable for ligation together, for example but not limited to the 3'-end of the upstream strand does not comprise a 3'-OH group, the 5'-end of the downstream strand does not comprise a 5'-phosphate group, or both.

Some ligase inhibitor embodiments comprise at least three oligonucleotides, a first oligonucleotide, a second oligonucleotide, and a third oligonucleotide, wherein the first oligonucleotide comprises a first region, the second oligonucleotide comprises a third region and a fourth region, and the third oligonucleotide comprises a sixth region, wherein the first region is complementary with the third region and the fourth region is complementary with the sixth region.

Certain ligase inhibitors comprise two oligonucleotides, including a first oligonucleotide and a second oligonucleotide, wherein the first oligonucleotide comprises a first region, a second region, a third region and a fourth region and the second oligonucleotide comprises a sixth region, and wherein the first region is complementary with the third region and the fourth region is complementary with the sixth region. Under appropriate conditions, including at a first temperature, the first region and the third region can anneal and form at least one double-stranded segment and the fourth region and the sixth region can anneal to form at least one double-stranded segment. Other ligase inhibitor embodiments comprise more than two oligonucleotides that can, under appropriate conditions including at a first temperature, anneal to form hybridization structure comprising a nick or a gap between two adjacently hybridized oligonucleotide ends that can not be closed by a ligase. In certain ligase inhibitor embodiments, at least one nucleotide at or near the 3-end of the upstream oligonucleotide, the 5'-end of the downstream oligonucleotide, or both, is not complementary with the corresponding nucleotide(s) of the third oligonucleotide, to which the first and second oligonucleotides adjacently anneal. Thus at least one of the opposing ends is not efficiently annealed with the template and the ligase is unable to ligate them together.

In certain embodiments, a cleaving enzyme inhibitor comprises a flap sequence comprising at least one internucleotide linkage that is not cleavable or is slowly cleaved by the cleaving enzyme. An exemplary embodiment of such an inhibitor is shown schematically in FIG. 1 F. The illustrative inhibitor comprises a first region (1), a second region (2), a third region (3) comprising a first quencher (6), a fourth region (4), a fifth region (8), and a sixth region (9) that in this illustrative inhibitor comprises a second quencher (7). The first region (1) and the third region (3) are shown annealed to form a first double-stranded segment, the fourth region (4) and the sixth region (9) are annealed to form a second double-stranded segment, and the second region (2) and the fifth region (8) are each shown as loop structures. Upstream from the first region (1) is a flap sequence (11) that in this exemplary embodiment, comprises a multiplicity of internucleotide linkages that can not be cleaved by the cleaving enzyme (12). In this conformation, the illustrative enzyme inhibitor forms a cleavage structure mimic, that is a secondary structure that resembles a nucleic acid cleavage structure but which serves as an ineffective substrate for the cleaving enzyme. In certain embodiments, for example but not limited to, when the cleaving enzyme comprises a DNA polymerase with polymerization activity and/or when the reaction composition comprises a cleaving enzyme and a DNA polymrase, the 3'-end of the cleaving enzyme inhibitor comprises a non-extendible nucleotide, including without limitation a ddN.

In certain embodiments, the nucleotide sequence of an enzyme inhibitor comprises an aptamer that comprises at least one double-stranded segment and that binds to and inhibits the enzymatic activity of the enzyme when bound by the aptamer. When the aptamer is free in solution below the second temperature or is bound to the enzyme in a complex, the quencher absorbs at least some of the fluorescent signal generated by nucleic acid dye molecules associated with the aptamer.

Certain Exemplary Complexes

A complex according to the present teachings comprises an enzyme inhibitor associated with an enzyme such that at least one enzymatic activity of the enzyme is inhibited. In certain embodiments, a complex comprises an enzyme inhibitor associated with an amplifying enzyme, for example, any enzyme that is included in an amplification reaction. In some embodiments, a complex comprises an RNA polymerase associated with an RNA polymerase inhibitor. In some embodiments, a complex comprises a ligase inhibitor associated with a ligase. In some embodiments, a complex comprises a helicase inhibitor associated with a helicase. In certain embodiments, a complex comprises a cleaving enzyme associated with a cleaving enzyme inhibitor. Some complexes further comprise additional components, for example but not limited to, a deoxyribonucleotide (dNTP), a ribonucleotide (rNTP), a nucleotide analog, a helicase accessory protein, an SSB, or an enzyme cofactor including without limitation, ATP and nicotinamide adenine dinucleotide (NAD+), and including non-cleavable analogs thereof that can participate in the formation and/or stabilization of certain enzyme-enzyme inhibitor complexes, or combinations thereof.

In certain embodiments, an enzyme-enzyme inhibitor complex comprises a DNA polymerase associated with a DNA polymerase inhibitor. In certain embodiments, a complex comprising a DNA polymerase inhibitor and a DNA polymerase further comprises a NTP and/or a nucleotide analog that can participate in the DNA polymerase inhibitor-DNA polymerase complex. According to the present teachings, when a DNA polymerase is complexed (i.e., associated in a complex) with a DNA polymerase inhibitor and optionally a NTP and/or a nucleotide analog, the enzymatic activity of the DNA polymerase with respect to its ability to catalyze the addition of nucleotides to the 3'-end of a primer or a nascent polynucleotide strand is inhibited. Typically, the disclosed DNA polymerase inhibitors are designed to form at least one double-stranded segment and complex with a DNA polymerase at a first temperature. When the complex is heated to a second temperature, the double-stranded segment of the DNA polymerase inhibitor denatures and the complex dissociates. When released from the complex, the synthetic activity of the DNA polymerase is restored and, under appropriate conditions, certain nucleic acid sequences can be amplified.

According to certain embodiments, a complex comprises a DNA polymerase inhibitor associated with a DNA polymerase such that the enzymatic activity of the DNA polymerase is inhibited. In some embodiments, a complex comprises a DNA polymerase inhibitor in a single or double stem-loop conformation associated with a DNA polymerase. In some embodiments, a complex comprises a DNA polymerase associated with a DNA polymerase inhibitor comprising at least two oligonucleotides that are annealed to form at least one double-stranded segment.

Typically, the first and third regions of a DNA polymerase inhibitor anneal to form a double-stranded segment at the first temperature and the DNA polymerase inhibitor assumes a stem-loop conformation or a duplex conformation, as appropriate. In certain embodiments, the fourth and sixth regions of a DNA polymerase inhibitor anneal to form a double-stranded segment at the first temperature and the DNA polymerase inhibitor assumes a stem-loop conformation, a double stem-loop conformation, or a duplex conformation, as appropriate. When a DNA polymerase inhibitor in a stem-loop or a duplex conformation is combined with a DNA polymerase, the DNA polymerase inhibitor and the DNA polymerase can associate to form a complex, wherein the DNA polymerase activity is inhibited. As the reaction temperature is increased, the double-stranded segment(s) of the DNA polymerase inhibitors denature at or near the second temperature, causing the complex to dissociate and releasing the inhibition of the DNA polymerase.

The DNA polymerases of the current teachings typically include but are not limited to, DNA-dependent DNA polymerases and RNA-dependent DNA polymerases, including reverse transcriptases. Certain reverse transcriptases possess DNA-dependent DNA polymerase activity under certain reaction conditions, including AMV reverse transcriptase and MMLV reverse transcriptase. Such reverse transcriptases with DNA-dependent DNA polymerase activity may be suitable for use with the disclosed methods and are expressly within the contemplation of the current teachings. Descriptions of DNA polymerases can be found in, among other places, Lehninger Principles of Biochemistry, 3d ed., Nelson and Cox, Worth Publishing, New York, N.Y., 2000, particularly Chapters 26 and 29; Twyman, Advanced Molecular Biology: A Concise Reference, Bios Scientific Publishers, New York, N.Y., 1999; Ausubel et al.; Lin and Jaysena, J. Mol. Biol. 271:100-11, 1997; Pavlov et al., Trends in Biotechnol. 22:253-60, 2004; and Enzymatic Resource Guide: DNA polymerases, 1998, Promega, Madison, Wis.

Inhibition of DNA polymerase activity can be observed with respect to the synthesis of secondary amplicons or more generally, with respect to overall nucleic acid synthesis by the DNA polymerase. In general, one of skill in the art may choose to optimize synthesis of desired amplicons while minimizing synthesis of spurious side-products. Hence, when generating a desired amplicon, the disclosed DNA polymerase inhibitors can inhibit synthesis of secondary amplicons by about 5%, about 10%, about 15%, about 20%, about 25%, about 30%, about 35%, about 40%, about 45%, about 50%, about 55%, about 60%, about 65%, about 70%, about 75%, about 85%, about 90%, about 95%, about 96%, about 97%, about 98%, about 99%, or greater than about 99%, when compared to the amount of secondary amplicons synthesized in the absence of the selected DNA polymerase inhibitor.

Inhibition of ligase activity can be observed with respect to the synthesis of undesired side-products, including without limitation, misligation products, or more generally, with respect to overall nucleic acid amplification in the reaction composition, for example but not limited to, a reaction composition in which LCR, LDR, LDR-PCR, PCR-LDR, or FEN-LCR occurs. In general, one of skill in the art may choose to optimize synthesis of desired amplicons while minimizing synthesis of spurious side-products. Hence, when generating a desired amplicon, the disclosed ligase inhibitors can inhibit synthesis of undesired side products by about 5%, about 10%, about 15%, about 20%, about 25%, about 30%, about 35%, about 40%, about 45%, about 50%, about 55%, about 60%, about 65%, about 70%, about 75%, about 85%, about 90%, about 95%, about 96%, about 97%, about 98%, about 99%, or greater than about 99%, when compared to the amount of secondary amplicons synthesized in the absence of the selected ligase inhibitor.

Inhibition of cleaving enzyme activity can be observed with respect to the synthesis of undesired side-products or more generally, with respect to overall nucleic acid amplification in the reaction composition, for example but not limited to a reaction composition in which FEN-LCR occurs. In general, one of skill in the art may choose to optimize synthesis of desired amplicons while minimizing synthesis of spurious side-products. Hence, when generating a desired amplicon, the disclosed cleaving enzyme inhibitors can inhibit synthesis of undesired side products by about 5%, about 10%, about 15%, about 20%, about 25%, about 30%, about 35%, about 40%, about 45%, about 50%, about 55%, about 60%, about 65%, about 70%, about 75%, about 85%, about 90%, about 95%, about 96%, about 97%, about 98%, about 99%, or greater than about 99%, when compared to the amount of secondary amplicons synthesized in the absence of the selected cleaving enzyme inhibitor.

Inhibition of helicase activity can be observed with respect to the synthesis of secondary amplicons or more generally, with respect to overall nucleic acid synthesis in the reaction composition, for example but not limited to a reaction composition in which HDA occurs. In general, one of skill in the art may choose to optimize synthesis of desired target nucleic acids while minimizing synthesis of spurious side-products. Hence, when generating a desired amplicon, the disclosed helicase inhibitors can inhibit synthesis of secondary amplicons by about 5%, about 10%, about 15%, about 20%, about 25%, about 30%, about 35%, about 40%, about 45%, about 50%, about 55%, about 60%, about 65%, about 70%, about 75%, about 85%, about 90%, about 95%, about 96%, about 97%, about 98%, about 99%, or greater than about 99%, when compared to the amount of secondary amplicons synthesized in the absence of the selected helicase inhibitor.

The disclosed enzyme inhibitors can be combined with the enzymes in a variety of ratios or concentrations to form complexes. In some embodiments, the enzyme inhibitor is present at a larger molar concentration than the enzyme. In other embodiments, the enzyme inhibitor is present at about the same or a lesser molar concentration than the enzyme. One of skill in the art may choose to use a molar ratio of enzyme inhibitor to enzyme that is greater than 1:1 (inhibitor:enzyme) in order to insure that sufficient enzyme inhibitor is present so that every enzyme molecule can associate with an enzyme inhibitor to form a complex. In general, highly effective enzyme inhibitors may be used at lower concentrations than less effective enzyme inhibitors. Hence, enzyme inhibitors can be provided in a reaction composition at a variety of concentrations. Such concentrations can vary, for example, from about 1 nM to about 10 mM, or from about 5 nM to about 1 mM, or from about 10 nM to about 100 µM, or other convenient concentrations selected by one of skill in the art.

The enzyme inhibitors disclosed herein can be combined with an enzyme either before or during an amplification reaction to form a complex provided that the amplification reaction conditions comprise at least one step at the first temperature. In certain embodiments, an enzyme and an enzyme inhibitor are combined at the first temperature before the reaction composition is formed. Such a pre-incubation step may facilitate the formation of an enzyme inhibitor-enzyme complex and help decrease or eliminate the synthesis of undesired side-products such as mis-primed amplicons, misligated probes, and oligomerized primers.

Certain Exemplary Methods

The disclosed enzyme inhibitors serve at least two functions in the methods of the current teachings. First, the disclosed enzyme inhibitors serve to inhibit the enzymatic activity of a corresponding enzyme at a first temperature, decreasing secondary amplicon formation due to, among other things, mis-annealing or primers and/or probes to sequences other than target nucleic acids and primer dimer formation. Those in the art will appreciate that by decreasing the formation of secondary amplification products, the enzyme inhibitors of the current teachings can reduce the non-specific fluorescence of the reaction composition. Second, the disclosed enzyme inhibitors can also reduce the non-specific fluorescence in the reaction composition due to the self-quenching ability of the enzyme inhibitor, as the at least one quencher moiety can absorb at least some of the fluorescence emitted by the nucleic acid dye molecules associated with the double-stranded segment(s) of the enzyme inhibitor. In certain embodiments, enzyme inhibitors also increase the amplicon yield in the disclosed methods.

Methods for amplifying a target nucleic acid are provided. According to certain method embodiments, a reaction composition is formed at a first temperature, wherein the reaction composition comprises a DNA polymerase, a DNA polymerase inhibitor comprising a nucleotide sequence and a quencher, a nucleoside triphosphate (NTP), typically a mixture of deoxyribonucleotide triphosphates (dNTPs), a target nucleic acid, a primer, and a nucleic acid dye. In certain embodiments, a reaction composition further comprises a nucleotide analog. In some embodiments, the DNA polymerase, the DNA polymerase inhibitor, and optionally a NTP and/or a nucleotide analog, are combined prior to forming the reaction composition. In certain embodiments, the DNA polymerase and the DNA polymerase inhibitor are pre-incubated at the first temperature prior to forming the reaction composition. At the first temperature, the nucleotide sequence of the DNA polymerase inhibitor comprises at least one double-stranded segment and the DNA polymerase and the DNA polymerase inhibitor can associate to form a complex. The quencher absorbs at least some of the fluorescent signal emitted by the nucleic acid dye molecules associated with the double-stranded segment of the nucleotide sequence, relative to the signal that is detected in a parallel reaction composition comprising the same DNA polymerase inhibitor nucleotide sequence but lacking the quencher(s). The reaction composition is then heated to a second temperature that is near, at, or above the melting temperature of the DNA polymerase inhibitor, causing the double-stranded segment to denature and dissociating the complex. With the release of the DNA polymerase inhibitor, from the complex, the enzymatic activity of the DNA polymerase is no longer inhibited. The reaction composition is subjected to at least one cycle of amplification to generate a multiplicity of amplicons.

Methods for reducing non-specific fluorescence in a reaction composition are provided. According to certain such methods, a reaction composition is formed at a first temperature, wherein the reaction composition comprises a DNA polymerase, a DNA polymerase inhibitor comprising a nucleotide sequence and a quencher, a NTP, typically a mixture of dNTPs, a target nucleic acid, a primer, and a nucleic acid dye. In certain embodiments, a reaction composition further comprises a nucleotide analog. In some embodiments, the DNA polymerase, the DNA polymerase inhibitor, and optionally a NTP and/or nucleotide analog, are combined prior to forming the reaction composition. In certain embodiments, the DNA polymerase and the DNA polymerase inhibitor are pre-incubated at the first temperature to form a complex prior to forming the reaction composition. The quencher absorbs at least some of the fluorescent signal emitted by the nucleic acid dye molecules associated with the double-stranded segment of the nucleotide sequence, relative to the signal that is detected in a parallel reaction composition comprising the same DNA polymerase inhibitor nucleotide sequence but lacking the quencher(s). The reaction composition is then heated to a second temperature that is near, at, or above the melting temperature of the DNA polymerase inhibitor, causing the double-stranded segment to denature and dissociating the complex. With the release of the DNA polymerase, from the complex, the polymerization activity of the DNA polymerase is no longer inhibited. The reaction composition is subjected to at least one cycle of amplification to generate a multiplicity of amplicons. Under appropriate detection conditions, the fluorescence of the nucleic acid dye associated with the multiplicity of amplicons in the reaction composition can be detected, while the fluorescence of the nucleic acid dye associated with the double-stranded segment of the nucleotide sequence of the DNA polymerase inhibitor is at least reduced by the quencher.

In some embodiments, the at least one cycle of amplification comprises a multiplicity of cycles of amplification, for example but not limited to, at least 10 cycles, at least 15 cycles, at least 20 cycles, at least 25 cycles, at least 30 cycles, at least 35 cycles, at least 40 cycles, or more than 40 cycles of amplification. In some embodiments, the subjecting the reaction composition to at least one cycle of amplification comprises PCR, including variations of PCR, for example but not limited to, RT-PCR, asymmetric PCR, or quantitative or real-time PCR (see, e.g., Rapley, particularly Part VII; Protocols & Applications Guide, rev. 9/04, Promega; McPherson).

Certain embodiments of the disclosed methods comprise a multiplex amplification step, including but not limited to a multiplicity of parallel single-plex or lower plexy amplification reactions (for example 2-plex, 3-plex, 4-plex, 5-plex, or 6-plex amplification reactions), a multiplex detection step, including but not limited to a multiplicity of parallel single-plex of lower plexy detection steps (for example wherein two, three, four, five, or six different amplicons are detected in the same reaction composition), or both a multiplex amplification reaction and a multiplex detection procedure. In some embodiments, the target nucleic acid comprises a multiplicity of different target nucleic acids, the primer comprises a multiplicity of different primers or a multiplicity of different primer pairs, the multiplicity of amplicons comprises a multiplicity of different amplicons, and the detecting comprises detecting the fluorescence of the nucleic acid dye associated with the multiplicity of different amplicons.

The degree of enzymatic inhibition obtained using the disclosed DNA polymerase inhibitors can vary and may depend upon the method employed, the DNA polymerase, the structure and melting point of the selected DNA polymerase inhibitor and other factors such as the primer extension temperature. Each of these variables can be optimized by one of skill in the art to using the teachings herein and/or available procedures to obtain optimal production of the desired product with minimal production or non-target nucleic acids. Likewise, the level of non-specific fluorescence reduction can vary, depending upon, among other things, the particular quencher(s) in the nucleotide sequence, the number of quenchers employed per DNA polymerase inhibitor, the nucleic acid dye employed, the reaction conditions, and the effectiveness of the DNA polymerase inhibitor at decreasing the amount on secondary amplification products. Those in the art will appreciate that the number and placement of a particular quencher or quenchers in a particular DNA polymerase inhibitor, the pairing of a particular DNA polymerase with a particular DNA polymerase inhibitor, and the pairing of a particular quencher with a particular nucleic acid dye, can be evaluated empirically using routine methods known in the art and without undue experimentation to optimize the reduction of non-specific fluorescence in a particular reaction composition and amplification technique.

According to certain method embodiments, a ligase forms a complex with a ligase inhibitor at a first temperature in a reaction composition comprising a target nucleic acid and a ligation probe pair. In certain embodiments, the ligase and the ligase inhibitor are combined and pre-incubated prior to forming a reaction composition. At a first second temperature, the ligase-ligase inhibitor complex dissociates, releasing the ligase. The upstream and downstream ligation probes of the ligation probe pair selectively hybridize with the target nucleic acid and the ligase catalyzes the formation of a ligated probe. Some such embodiments comprise a multiplicity of cycles of amplification comprising the steps of denaturing, annealing the upstream and downstream ligation probes, and ligating the probes to generate a ligated probe. In certain embodiments, the reaction composition comprises a ligation probe pair that is designed to specifically hybridize with at least a portion of the complement of a ligated probe. In some embodiments, a ligated probe comprises a primer-binding site and the reaction composition comprises a primer and a DNA polymerase-DNA polymerase complex.

According to certain disclosed methods, a cleaving enzyme forms a complex with a cleaving enzyme inhibitor and a ligase forms a complex with a ligase inhibitor at a first temperature. In certain embodiments, at a first second temperature, the cleaving enzyme-cleaving enzyme inhibitor complex dissociates. The released cleaving enzyme can then cleave flap portions from certain overlap flap structures comprising (1) a target nucleic acid or a single-stranded amplicon, (2) a upstream cleavage probe, and (3) a corresponding downstream cleavage probe that comprises a 5'-overhang or flap sequence that overlaps the 3'-end of the upstream cleavage probe by at least one nucleotide. When the flap is cleaved by the cleaving enzyme, a hybridization structure comprising the template strand, the upstream cleavage probe, and the hybridized fragment of the downstream cleavage probe, with a ligatable nick between the 3'-end of the upstream cleavage probe and the 5'-end of the hybridized fragment of the downstream cleavage probe. In some embodiments, at a second second temperature the ligase-ligase inhibitor complex dissociates and the released ligase can ligate the nick in the hybridization structure to generate a duplex comprising a ligated probe and a template strand. In certain embodiments, a ligated probe comprises at least one primer-binding site. Those in the art will appreciate that the first second temperature and the second second temperature can be approximately the same temperatures or they can be different temperatures.

Some method embodiments further comprise a DNA polymerase-DNA polymerase inhibitor complex at a first temperature. At an appropriate third second temperature the DNA polymerase-DNA polymerase inhibitor complex dissociates. Under suitable conditions, a primer specifically hybridizes with the primer-binding portion of a ligated probe and primer extension can occur. Those in the art will appreciate that when different enzyme inhibitors are employed in a reaction composition, at least two of: the first second temperature, the second second temperature, and the third second temperature can be approximately the same temperatures or they can all be different temperatures.

Exemplary cleaving enzymes for use in the disclosed complexes, methods and kits include without limitation, *E. coli* DNA polymerase I, *Thermus aquaticus* DNA polymerase I, *Thermus thermophilus* DNA polymerase I, mammalian FEN-1, *Archaeoglobus fulgidus* FEN-1, *Methanococcus jannaschii* FEN-1, *Pyrococcus furiosus* FEN-1, *Methanobacterium thermoautotrophicum* FEN-1, *Thermus thermophilus* FEN-1, Cleavase® enzymes (Third Wave, Inc., Madison, Wis.), *Saccharomyces cerevisiae* RTH1, *S. cerevisiae* RAD27 *Schizosaccharomyces pombe* rad2, bacteriophage T5 5'-3' exonuclease, *Pyroccus horikoshii* FEN-1, human exonuclease 1, calf *thymus* 5'-3' exonuclease, including homologs thereof in eubacteria, eukaryotes, and archaea, such as members of the class II family of structure-specific enzymes. Descriptions of cleaving enzymes can be found in, among other places, Lyamichev et al., Science 260:778-83 (1993); Eis et al., Nat. Biotechnol. 19:673-76 (2001); Shen et al., Trends in Bio. Sci. 23:171-73 (1998); Kaiser et al. J. Biol. Chem. 274:21387-94 (1999); Ma et al., J. Biol. Chem. 275:24693-700 (2000); Allawi et al., J. Mol. Biol. 328:537-54 (2003); Sharma et al., J. Biol. Chem. 278:23487-96 (2003); and Feng et al., Nat. Struct. Mol. Biol. 11:450-56 (2004).

According to certain disclosed methods, a DNA polymerase is combined with a DNA polymerase inhibitor, and optionally a NTP and/or a nucleotide analog, to form a complex. In certain embodiments, the DNA polymerase comprises a reverse transcriptase, a DNA-dependent DNA polymerase, including without limitation a thermostable DNA polymerase, or a reverse transcriptase and a DNA-dependent DNA polymerase. In some embodiments, the DNA polymerase inhibitor comprises (1) a first DNA polymerase inhibitor that can form a complex with the reverse transcriptase at a suitable first temperature, (2) a second DNA polymerase inhibitor that can form a complex with the DNA-dependent DNA polymerase at a suitable first temperature, or (3) a first DNA polymerase inhibitor that can form a complex with the reverse transcriptase at a suitable first temperature and a second DNA polymerase inhibitor that can form a complex with the DNA-dependent DNA polymerase at a suitable first temperature, wherein the first DNA polymerase inhibitor and the second DNA polymerase inhibitor comprise the same nucleotide sequence or a different nucleotide sequence, and wherein the suitable first temperature for the first DNA polymerase inhibitor and the suitable first temperature for the second DNA polymerase inhibitor are the same temperature or different temperatures.

According to certain disclosed methods, amplification comprises a two phase PCR reaction comprising two different reaction compositions, a first reaction composition and a second reaction composition, each comprising a DNA polymerase and a DNA polymerase inhibitor. In certain such embodiments, a first reaction composition comprises a first DNA polymerase, a first DNA polymerase inhibitor, a NTP, typically a mixture of NTPs, and a primer, typically a multiplicity of different primer pairs. In certain embodiments, the DNA polymerase, the DNA polymerase inhibitor, and optionally a NTP and/or a nucleotide analog are combined prior to forming the first reaction composition. The first reaction composition is subjected to a limited number of cycles of amplification, for example but not limited to two, three, four, five, six, seven, eight, nine, ten, eleven, twelve, thirteen, fourteen, or fifteen cycles of amplification. The first reaction composition is diluted after the limited first stage amplification and a portion of the diluted first reaction composition is combined with a second DNA polymerase, a second DNA polymerase inhibitor, a NTP, typically a mixture of NTPs, and a primer, typically a primer pair. In certain embodiments, the DNA polymerase, the DNA polymerase inhibitor, and optionally a NTP and/or a nucleotide analog, are combined prior to forming the second reaction composition. The second reaction composition is subjected to a multiplicity of cycles of amplification, for example but not limited to, 10-45 cycles of amplification or 20-40 cycles of amplification, including any number of cycles of amplification in the listed ranges, as if each and every number of cycles was expressly recited herein. In some embodiments, there is enough residual first DNA polymerase in the diluted first reaction composition that a second DNA polymerase is not necessary. In some embodiments, there is enough residual first DNA polymerase inhibitor in the diluted first reaction composition that a second DNA polymerase inhibitor is not necessary. In certain embodiments, the first DNA polymerase and the second DNA polymerase are the same polymerase or different polymerases, including without limitation, a reverse transcriptase and a DNA-dependent DNA polymerase. In some embodiments, the first DNA polymerase inhibitor and the second DNA polymerase inhibitor are the same inhibitor ar a different inhibitor. For illustration purposes but not as a limitation of such embodiments, consider an exemplary RT-PCR reaction that comprises a first reaction comprising a reverse transcriptase, a first DNA polymerase inhibitor, and optionally, a NTP and/or a nucleotide analog and a second reaction composition comprising a thermostable DNA-dependent DNA polymerase, a second DNA polymerase inhibitor, and optionally a NTP and/or a nucleotide analog. The first DNA polymerase inhibitor can be designed to inhibit the reverse transcriptase activity at temperatures below the optimal temperature for reverse transcription (i.e., an exemplary first phase first temperature), but not at or above the optimal reverse transcription temperature (i.e., an exemplary first phase second temperature). The second DNA polymerase inhibitor can be designed to inhibit the enzymatic activity of the thermostable DNA polymerase at temperatures below the second phase first temperature, for example but not limited to, a temperature about 5° C. to about 10° C. below or about 4° C. below to about 6° C. below the Tm of at least one of the PCR primers (i.e., an exemplary second phase first temperature), but not above the Tm of the PCR primers (i.e., an exemplary first phase second temperature).

The methods of the current teachings can typically be used with any target nucleic acid. The disclosed methods are useful not only for producing large amounts of a desired amplicon, but also for producing or sequencing nucleic acids that are known to exist but are not completely sequenced or purified. One need know only the identity of a sufficient number of bases at one or two ends of the target, i.e., a target flanking sequence, in sufficient detail so that at least one primer can be prepared that can serve as a sequencing primer. After sequencing and identification of an acceptable second target flanking sequence, a second primer can be made and the target nucleic acid lying between the flanking sequences can be exponentially amplified and in some embodiments, quantified. In other embodiments, when sufficient sequence has been obtained, an appropriate ligation probe set and/or an appropriate cleavage probe set can be synthesized.

In certain embodiments of the disclosed methods, detecting comprises evaluating an internal standard or a control sequence, and may include comparing the quantity of a desired amplicon with a standard curve or an internal size standard. In some embodiments, a control sequence, a passive reference dye, or both are included in a reaction composition to account for lane-to-lane, capillary-to-capillary, and/or assay-to-assay variability.

Certain embodiments of the current methods further comprise a multi-well reaction vessel, including without limitation, a multi-well plate or a multi-chambered microfluidic device, in which a multiplicity of amplification reactions and, in some embodiments, detection are performed, typically in parallel. In certain embodiments, one or more multiplex reactions for generating amplicons are performed in the same reaction vessel, including without limitation, a multi-well plate, such as a 96-well, a 384-well, a 1536-well plate, and so forth; or a microfluidic device, for example but not limited to, a TaqMan® Low Density Array (Applied Biosystems). In some embodiments, a massively parallel amplifying step comprises a multi-well reaction vessel, including a plate comprising multiple reaction wells, for example but not limited to, a 24-well plate, a 96-well plate, a 384-well plate, or a 1536-well plate; or a multi-chamber microfluidics device, for example but not limited to a TaqMan Low Density Array wherein each chamber or well comprises an appropriate primer(s), primer set(s), and/or reporter probe(s), as appropriate. Typically such amplification steps occur in a series of parallel single-plex, two-plex, three-plex, four-plex, five-plex, or six-plex reactions, although higher levels of parallel multiplexing are also within the intended scope of the current teachings.

In certain embodiments, the reaction composition further comprises a passive reference dye. The passive reference dye is included in the reaction composition as an internal control to allow for normalization of non-PCR related variations in fluorescence, for example but not limited to, well-to-well, tube-to-tube, plate-to-plate, and assay-to-assay variation. The passive reference provides a baseline for normalization because its fluorescence does not change during the course of the amplification reaction. Typically, the passive reference does not interfere with amplification reactions. The use of a passive reference dye and normalization calculations based on the passive reference, for example but not limited to, Rn and ΔRn, are well known in the art (see, e.g., Killigore et al., J. Clin. Micro., 38:2516-19, 2000; TaqMan® PCR Reagent Kit With AmpliTaq Gold® DNA polymerase Protocol, Applied Biosystems P/N 402823 Rev. D 2003; Brilliant® SYBR® Green QRT-PCR Master Mix Kit, 1-step Instruction Manual, Rev. #75003a, Stratagene, 2005; and Essential of Real Time PCR, Applied Biosystems). In some embodiments, the passive reference dye comprises ROX™ or TAMRA™.

Certain Exemplary Kits

The instant teachings also provide kits designed to expedite performing certain of the disclosed methods. Kits may serve to expedite the performance of certain disclosed methods by assembling two or more components required for carrying out the methods. In certain embodiments, kits contain components in pre-measured unit amounts to minimize the need for measurements by end-users. In some embodiments, kits include instructions for performing one or more of the disclosed methods. Preferably, the kit components are optimized to operate in conjunction with one another.

Certain disclosed kits comprise an enzyme inhibitor comprising a nucleotide sequence and a quencher. In certain embodiments, kits comprise at least one of: a ligase inhibitor, a helicase inhibitor, a RNA polymerase inhibitor, a cleaving enzyme inhibitor, and/or a DNA polymerase inhibitor. Certain kits of the current teachings further comprise at least one of: a ligase, a helicase, an RNA polymerase, and a cleaving enzyme. Certain kits comprise an enzyme inhibitor and further comprise at least one of: a primer, including without limitation a random primer or a primer comprising oligo dT, or a primer pair; a ligation probe pair; a cleavage probe set; a ligase cofactor including without limitation, ATP or NAD; an SSB; and/or a helicase accessory protein. In some embodiments, kits comprise a primer, a DNA polymerase, a ligase, or combinations thereof. In certain embodiments, kits comprise a NTP, a nucleotide analog, or both.

Certain kit embodiments comprise a DNA polymerase inhibitor comprising a nucleotide sequence and a quencher. In certain embodiments, a kit comprises a DNA polymerase; a control sequence, for example but not limited to an internal standard sequence such as a housekeeping gene and/or a coamplification sequence (see, e.g., Siebert and Larrick, BioTechniques 14:244-49 (1993); Joyce, Quantitative RT-PCR, 83-92, in Methods in Mol Biol., vol. 193, O'Connell, ed., Humana Press; Raeymaekers, Mol. Biotechnol. 115-22 (2000)) or a polynucleotide ladder comprising molecular size or weight standards; a primer and/or a primer pair; a reporter probe; a nucleic acid dye; a passive reference dye; or combinations thereof. In certain embodiments, kits comprise a multiplicity of different primer pairs. In some embodiments, kits comprise a forward primer, a reverse primer, or a forward primer and a reverse primer, that further comprises a reporter group. In some such embodiments, the reporter group of a forward primer of a primer pair is different from the reporter group of the reverse primer of the primer pair.

The skilled artisan will appreciate that many different species of reporter groups can be used in the present teachings, either individually or in combination with one or more different reporter group. In certain embodiments, a reporter group emits a fluorescent, a chemiluminescent, a bioluminescent, a phosphorescent, or an electrochemiluminescent signal. Some non-limiting examples of reporter groups include fluorophores, radioisotopes, chromogens, enzymes, antigens including but not limited to epitope tags, semiconductor nanocrystals such as quantum dots, heavy metals, dyes, phosphorescence groups, chemiluminescent groups, electrochemical detection moieties, binding proteins, phosphors, rare earth chelates, transition metal chelates, near-infrared dyes, electrochemiluminescence labels, and mass spectrometer-compatible reporter groups, such as mass tags, charge tags, and isotopes (see, e.g., Haff and Smirnov, Nucl. Acids Res. 25:3749-50, 1997; Xu et al., Anal. Chem. 69:3595-3602, 1997; Sauer et al., Nucl. Acids Res. 31:e63, 2003). Detailed protocols for attaching reporter groups to nucleic acids can be found in, among other places, Hermanson, Bioconjugate Techniques, Academic Press, San Diego, 1996; Current Protocols in Nucleic Acid Chemistry, Beaucage et al., eds., John Wiley & Sons, New York, N.Y. (2000), including supplements through August 2005; and Haugland, Handbook of Fluorescent Probes and Research Products, 10th ed., Molecular Probes-Invitrogen, 2005.

In certain embodiments, a kit comprises two or more different enzyme inhibitors, for example but not limited to a ligase inhibitor and a cleaving enzyme inhibitor; a cleaving enzyme inhibitor, a ligase inhibitor, and a DNA polymerase inhibitor; or a helicase inhibitor and a DNA polymerase inhibitor. In some embodiments, a kit comprises two or more different DNA polymerase inhibitors. In certain embodiments, kits comprise two different enzymes, including without limitation, a DNA-dependent DNA polymerase and an RNA-dependent DNA polymerase, such as a reverse transcriptase; a ligase and a cleaving enzyme; an RNA polymerase and a DNA polymerase, for example but not limited to, a reverse transcriptase; and a helicase and a DNA polymerase. In certain embodiments, a kit comprises a thermostable DNA polymerase.

The current teachings, having been described above, may be better understood by reference to examples. The following examples are intended for illustration purposes only, and should not be construed as limiting the scope of the teachings herein in any way.

Example 1

To evaluate the effect of the quencher moiety of certain illustrative enzyme inhibitors to absorb at least some of the fluorescence emitted from nucleic acid dye molecules associated with double-stranded segments of the illustrative enzyme inhibitors, five exemplary DNA polymerase inhibitors were synthesized, as shown in Table 1 (below). The identity, location, and number of quencher moieties were varied.

TABLE 1

| Designation | Sequence (shown in 5' to 3' orientation) |
|---|---|
| "DNA polymerase inhibitor" A | TCTGGGATAATTATGGTAAATATGTTTTC ATATATTTATTATAATTATddC (SEQ ID NO: 1) |
| DNA polymerase inhibitor B | (Dabcyl) TCTGGGATAATTATGGTAAATAT ATGTTTTCATATATTTATTATAATTAT$^{dd}$C (SEQ ID NO: 1) |
| DNA polymerase inhibitor C | (ROX) TCTGGGATAATTATGGTAAATATG TTTTCATATATTTATTATAATTAT$^{dd}$C (SEQ ID NO: 1) |
| DNA polymerase inhibitor D | TCTGGGATAATTATGGTAAATATATGTTTTC ATATATTTATTATAATTATC (MGB-NFQ) (SEQ ID NO: 1) |
| DNA polymerase inhibitor E | TCTGGGATA(deazaA)TT(deazaA)TGGT A(deazaA)ATATGT(Dabcyl-T)TTC (deazaA)TATTTATTATAATTATC (MGB-NFQ) (SEQ ID NO: 3) |

A series of parallel compositions, each comprising 1×SYBR Green I nucleic acid dye (Molecular Probes) in 1× reaction buffer (50 mM Tris buffer, pH 9, 5 mM $MgCl_2$, 250 µM dATP, dCTP and dGTP, 500 µM dUTP, 60 nM ROX passive reference dye, and one of the exemplary DNA polymerase inhibitors shown in Table 1 at concentrations of 5 nM, 10 nM, 25 nM, 50 nM, 75 nM, or 100 nM, as appropriate, were formed at room temperature. As seen in Table 1, "DNA polymerase inhibitor" A, DNA polymerase inhibitor B, DNA polymerase inhibitor C, and DNA polymerase inhibitor D share the same nucleotide sequence except the nucleotide at the 3'-end of DNA polymerase inhibitor D is a C, while the nucleotide at the 3'-end of "DNA polymerase inhibitor" A, DNA polymerase inhibitor B, and DNA polymerase inhibitor C all comprise the nucleotide analog dideoxycytosine (ddC). "DNA polymerase inhibitor" A lacks a quencher moiety (thus A is not a true DNA polymerase inhibitor of the current teachings, indicated by the use of quotation marks: "DNA polymerase inhibitor"); DNA polymerase inhibitor B comprises a DAB-CYL quencher moiety at its 5'-end; DNA polymerase inhibitor C comprises a ROX quencher moiety at its 5'-end; and DNA polymerase inhibitor D comprises a minor groove binder comprising a non-fluorescent quencher (MGB-NFQ) at its 3'-end. DNA polymerase inhibitor E comprises a nucleotide sequence that includes four deaza-dA nucleotide analogs (shown as deazaA) and two G:T base pair mismatches in its first and third regions. DNA polymerase inhibitor E also comprises two quencher moieties, a DAB-CYL moiety in the second region loop and a MGB-NFQ at its 3'-end.

A dissociation curve was generated for each of the compositions using an ABI PRISM® 7900HT Real-Time Sequence Detection System instrument (Applied Biosystems) for the temperature range 30° C. to 95° C. The derivative of fluorescence versus temperature was calculated using the associated dissociation curve software. As shown in FIG. 3, the dissociation peak obtained from the composition comprising 100 nM "DNA polymerase inhibitor" A (shown as 100 nM A) at the Tm of this nucleotide sequence (approximately 56° C.) was much higher than the dissociation peaks obtained from the compositions comprising 100 nM, 75 nM, or 50 nM DNA polymerase inhibitor B (shown as 100 nM B, 75 nM B, and 50 nM B, respectively). As demonstrated in FIG. 3, the background fluorescence, presumably attributable to the fluorescent signal emitted from the nucleic acid dye molecules associated with the double-stranded segment of DNA polymerase inhibitor B, is reduced relative to "DNA polymerase inhibitor" A.

The dissociation curves obtained from the compositions comprising 100 nM "DNA polymerase inhibitor" A, 100 nM DNA polymerase inhibitor C, 75 nM DNA polymerase inhibitor C, and 50 nM DNA polymerase inhibitor C are shown in FIG. 4. As seen in FIG. 4, the dissociation peak obtained with 100 nM "DNA polymerase inhibitor" A is substantially higher that the dissociation peaks associated with 100 nM, 75 nM, or 50 nM of DNA polymerase inhibitor C.

The dissociation curves obtained from the composition comprising 50 nM "DNA polymerase inhibitor" A and the composition comprising 50 nM DNA polymerase inhibitor D are shown in FIG. 5. The dissociation peak obtained from the composition comprising 50 nM "DNA polymerase inhibitor" A (shown as A in FIG. 5) is substantially higher than the dissociation peak obtained form the composition comprising 50 nM DNA polymerase inhibitor D (shown as D).

FIG. 6 shows the dissociation curves obtained from the compositions comprising 100 nM, 75 nM, 50 nM, 25 nM, 10 nM or 5 nM "DNA polymerase inhibitor" A (shown as 100 nM/Std, 75 nM/Std, 50 nM/Std, 25 nM/Std, 10 nM/Std, and 5 nM/Std, respectively) and 100 nM, 75 nM, 50 nM, 25 nM, 10 nM or 5 nM DNA polymerase inhibitor E. As shown in FIG. 6, the dissociation peaks obtained from each of the compositions comprising "DNA polymerase inhibitor" A are detectably higher and generally substantially higher than the dissociation peak(s) obtained from the composition comprising DNA polymerase inhibitor E, which are essentially lost in the "baseline" and not readily distinguishable.

It is to be appreciated that these illustrative DNA polymerase inhibitors are intended as non-limiting examples of various DNA polymerase inhibitor designs, for example but not limited to, nucleotide sequence variations, with and without a minor groove binder, and different quencher moieties, including without limitation different numbers of quenchers per inhibitor, different quencher locations within the inhibitor (e.g., 3'-end, 5'-end and internal), and different specific quenchers (e.g., DABCYL, ROX, and NFQ). Those in the art will understand that various DNA polymerase inhibitor designs are possible and that a suitable DNA polymerase inhibitor can be obtained by routine evaluation of various designs, informed by the present teachings, for use with a particular DNA polymerase and a given set of reaction conditions.

Example 2

Inhibition of secondary amplicons during PCR amplification of an illustrative target nucleic acid in the plasminogen activator urokinase (PAU) gene of gDNA.

To evaluate the inhibitory ability of DNA polymerase inhibitor E in the amplification of a target nucleic acid in gDNA, a PCR reaction was performed. Six parallel 20 µL reaction compositions were formed at room temperature, with each reaction composition comprising: 40 ng human gDNA (Coriell); a PAU target nucleic acid-specific primer pair comprising 2.25 µM forward primer: 5'-TGTAAAAC-GACGGCCAGTTCTCATATTCTCTCATCCTCCT-GTCCC-3'(SEQ ID NO: 4) and 2.25 µM reverse primer: 5'-CAGGAAACAGCTATGACCAAGCGGCTTTAGGC-CCACCT-3' (SEQ ID NO: 5); and a final concentration of either 5, 10, 25, 50, 75 or 100 nM DNA polymerase inhibitor E; in 1×PCR buffer (50 mM Tris-HCl, pH 9, 250 µM dATP, dCTP and dGTP, 500 µM dUTP, 5 mM MgCl2, 0.6 U AmpliTaq DNA polymerase (Applied Biosystems), 60 nM ROX passive reference dye, 8% glycerol, 0.01% Tween-20, 0.01% NaN3, 1×SYBR Green I nucleic acid dye). A no template control was included in a seventh parallel reaction composition comprising the same formulation as the other six, except that there was no gDNA and the final concentration of DNA polymerase inhibitor E was 50 nM.

The reaction compositions were incubated at room temperature for approximately 15 min and then thermal cycled in an ABI PRISM® 7900HT Real-Time Sequence Detection System instrument (Applied Biosystems). The following cycles were used: 95° C. for 2 min, 40 cycles of 96° C. for 5 sec and 60° C. for 2 min. To evaluate the amplification products generated in each of the thermocycled reaction compositions, 15 µL of each reaction composition was loaded into separate lanes of a non-denaturing 4% agarose E-gel (InVitrogen, Carlsbad, Calif.), along with two lanes loaded with a molecular size ladder comprising markers of 500 base pairs, 400 base pairs, 300 base pairs, 200 base pairs, and 100 base pairs (Low Range DNA Marker, InVitrogen). The reaction compositions were loaded in lanes of the gel as follows: lane B, 5 nM inhibitor E; lane C, 10 nM inhibitor E; lane D, 25 nM inhibitor E; lane E, 50 nM inhibitor E; lane F, 75 nM inhibitor E; lane G, 100 nM inhibitor E; lane H, 50 nM inhibitor E, no template control. The samples were electrophoresed for 15 min, and visualized by ethidium bromide. As shown in FIG. 7, the amount of desired amplicon (11) increased as the concentration of DNA polymerase inhibitor increased until a concentration of about 75 nM (lane F). The intensity of the secondary amplicon bands, by contrast, decreased as the DNA polymerase inhibitor concentration increased.

Example 3

Inhibition of secondary amplicons during PCR amplification of an exemplary target nucleic acid of human cytochrome P450 in cDNA.

Seven parallel 20 µL reaction compositions were formed at room temperature, with each composition comprising: 10 ng universal reference human cDNA (Stratagene); a P450 target nucleic acid-specific primer pair comprising 200 nM forward primer: 5'-TGGGAGTCCTGGAAGCAGC-3' (SEQ ID NO: 6) and 200 nM reverse primer: 5'-TGGCT-TCTGGTCAACAAGTGC-3' (SEQ ID NO: 7); and a final concentration of either 0, 5, 10, 25, 50, 75 or 100 nM DNA polymerase inhibitor E; in 1×PCR buffer (50 mM Tris-HCl, pH 9, 250 µM dATP, dCTP and dGTP, 500 µM dUTP, 5 mM MgCl2, 1.5 U AmpliTaq DNA polymerase, 60 nM ROX passive reference dye, 8% glycerol, 0.01% Tween-20, 0.01% NaN$_3$, 1×SYBR Green I nucleic acid dye). A no template control was included in an eighth parallel reaction composition comprising the same formulation as the other seven except that there was no cDNA and the final concentration of DNA polymerase inhibitor E was 50 nM. The reaction compositions were incubated at room temperature for 15 min, then thermal cycled in an ABI PRISM® 7900HT Real-Time Sequence Detection System instrument and the amplification products were analyzed on a non-denaturing agarose gel, as described in Example 2. The reaction compositions were loaded in lanes of the gel as follows: lane B, 0 nM inhibitor E; lane C, 5 nM inhibitor E; lane d, 10 nM inhibitor E; lane E, 25 nM inhibitor E; lane F, 50 nM inhibitor E; lane G, 75 nM inhibitor E; lane H, 100 nM inhibitor E; and lane I, 50 nM inhibitor E, no template control.

As seen from the gel, shown in FIG. 8, the amount of desired amplicon (21) increased as the concentration of DNA polymerase inhibitor increased until a concentration of about 75 nM. Little to no desired amplicon was seen in the reaction composition comprising no DNA polymerase inhibitor E (lane A). The intensity of the secondary amplicon bands decreased as the DNA polymerase inhibitor concentration increased.

Example 4

Inhibiting secondary amplification products comprising primer dimers.

Five commercially available primer pairs and corresponding TaqMan reporter probes for validated gene expression assays, including assays for interleukin 1, beta (ID 8; assay ID Hs00174097_m1), TRAF family member-associated NFKB activator (TANK; assay ID Hs00370305_m1), fatty acid synthase (FASN; assay ID Hs00188012_m1), solute carrier family 2, member 1 (SLC2A1; assay ID Hs00197884_m1), and phospholipase D1, phosphatidylcholine-specific (PLD1; assay ID Hs00160118_m1) were obtained (Applied Biosystems).

To evaluate the effect of an exemplary enzyme inhibitor on the formation of primer dimer amplicons, five pairs of corresponding reaction compositions lacking target nucleic acid were prepared in parallel. Each 20 µL reaction composition pair comprised the appropriate primer pair and the corresponding TaqMan® probe at a 1× concentration; 250 µM dATP, dCTP and dGTP; 500 µM dUTP; 5 mM MgCl$_2$; 2 U AmpliTaq DNA polymerase; 60 nM ROX passive reference; 8% glycerol; 0.01% Tween-20; 0.01% NaN$_3$; 1×SYBR Green® I in 50 mM pH 9 Tris-HCl buffer; and either 50 nM polymerase inhibitor E or no inhibitor. The five sets of parallel reaction compositions were incubated at room temperature for 30 min and then transferred to an ABI PRISM® 7900HT Real-Time Sequence Detection System instrument. The reaction compositions were heated to 95° C. for 2 min, then subjected to 40 cycles of amplification comprising 96° C. for 5 sec and 60° C. for 2 min. Fifteen μL of the thermocycled reaction compositions was loaded in individual lanes of a 4% agarose E-gel (Invitrogen) as follows: IL1β assay, lanes B (no inhibitor) and C (50 nM polymerase inhibitor E); TANK assay, lanes D (no inhibitor) and E (50 nM polymerase inhibitor E); FASN assay, lanes F (no inhibitor) and G (50 nM polymerase inhibitor E); SLC2A1 assay, lanes (no inhibitor) H and I (50 nM polymerase inhibitor E); and PLD1 assay, lanes J (no inhibitor) and K (50 nM polymerase inhibitor E). A molecular weight standard comprising markers for 1200, 800, 400, 200, and 100 base pairs was added to lanes A and L. The gel was electrophoresed for 15 min, and visualized by staining with the nucleic acid dye ethidium bromide (shown in FIG. 9). The amount of undesired primer dimer product was at least reduced in reaction compositions comprising the inhibitor when compared with the corresponding reaction composition lacking the inhibitor, e.g., compare lanes B (IL1β assay, no inhibitor) and C (IL1β assay, 50 nM polymerase inhibitor E) or D (TANK assay, no inhibitor) and E (TANL assay, 50 nM polymerase inhibitor E).

Example 5

Decreasing non-specific fluorescence associated with enzyme inhibitors.

To evaluate the effect of an exemplary quencher moiety of an illustrative polymerase inhibitor using PCR amplification and melting curve analysis, two reaction compositions were prepared. Each 20 μL reaction composition comprised primers and reporter probes from the TANK assay (described in Example 4) at a 1× concentration; 10 ng universal reference human cDNA (Stratagene); 250 μM dATP, dCTP and dGTP; 500 μM dUTP; 5 mM MgCl$_2$; 2 U AmpliTaq DNA polymerase, 60 nM ROX passive reference, 8% glycerol, 0.01% Tween-20, 0.01% NaN$_3$, 1×SYBR Green I in 50 mM pH 9 Tris-HCl buffer and either 50 nM "polymerase inhibitor A" or 50 nM polymerase inhibitor E. The reaction compositions were incubated at room temperature for 15 min, then transferred to an ABI PRISM® 7900HT Real-Time Sequence Detection System instrument and thermocycled as described in Example 4. The instrument's associated software, set at default conditions, was used to generate the dissociation curves for the two thermocycled reaction compositions, shown in FIG. 10. Two dissociation peaks were observed when the thermocycled reaction composition comprised "polymerase inhibitor A", including peak A ("polymerase inhibitor A") and peak B (the TANK amplicon). The dissociation curve obtained with the thermocycled reaction composition comprising polymerase inhibitor B, by contrast, contained a peak for the TANK amplicon (shown as C in the lower panel), but no dissociation curve for polymerase inhibitor E was readily discernible.

The enzyme inhibitors, enzyme-enzyme inhibitor complexes, methods, and kits of the current teachings have been described broadly and generically herein. Each of the narrower species and sub-generic groupings falling within the generic disclosure also form part of the current teachings. This includes the generic description of the current teachings with a proviso or negative limitation removing any subject matter from the genus, regardless of whether or not the excised material is specifically recited herein.

The foregoing examples are for illustration purposes and are not intended to limit the scope of the teachings herein.

Although the disclosed teachings has been described with reference to various enzyme inhibitors, enzyme-enzyme inhibitor complexes, methods, and kits, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

We claim:

1. A complex comprising a DNA polymerase and an inhibitor of the DNA polymerase, the inhibitor comprising a contiguous nucleotide sequence configured as a stem-loop structure, and at least a first and a second quencher, wherein the contiguous nucleotide sequence comprises a first region, a second region, a third region, and optionally, a fourth region; wherein the first region and the third region anneal to form a double-stranded stem segment; wherein the first region and/or the third region comprise at least one nucleotide analog; and wherein the first region, or the fourth region if present, comprises the first quencher and the second region forms a loop and comprises the second quencher, wherein the at least one nucleotide analog is selected from the group consisting of a deaza-dA, a deaza-dG, a ddN, or any combination thereof; wherein the first and/or the second quencher is/are selected from the group consisting of a DABCYL moiety, a DABSYL moiety, a TAMRA moiety, a TET moiety, and a ROX moiety; wherein the nucleotide sequence of the DNA polymerase inhibitor comprises an aptamer; and wherein the DNA polymerase is a Taq DNA polymerase.

2. The complex of claim 1, wherein the inhibitor is not extendible by the DNA polymerase.

3. The complex of claim 1, wherein the first and/or the second quencher is DABCYL.

4. The complex of claim 1, wherein the at least one nucleotide analog is a dideoxynucleotide.

5. The complex of claim 4, wherein the dideoxynucleotide is ddC.

6. The complex of claim 1, wherein the DNA polymerase inhibitor further comprises a minor groove binder.

7. The complex of claim 1, wherein the DNA polymerase inhibitor comprises 5'-TCTGGGATA(deaza-dA)TT(deaza-dA)TGGTA(deaza-dA)ATATG(Tn)C(deaza-dA)TATTT-ATT(deaza-dA)TA(deaza-dA)TTATC-3', wherein the Tn is TT, TTT, TTTT, TTTTT, or TTTTTT.

8. The complex of claim 1, wherein the first and the second quenchers are the same.

9. The complex of claim 1, wherein the fourth region comprises a 5' overhang.

10. The complex of claim 1, wherein the first region comprises at least one mismatched base pair when annealed to the third region.

11. The complex of claim 10, wherein the at least one mismatched base pair is a G:T base pair.

* * * * *